(12) United States Patent
Cuevas et al.

(10) Patent No.: US 9,943,402 B2
(45) Date of Patent: Apr. 17, 2018

(54) MICROPATTERNED INTRAOCULAR IMPLANT

(71) Applicants: InSight Innovations, LLC, Littleton, CO (US); Sharklet Technologies, Inc., Aurora, CO (US); University of Florida Research Foundation, Inc., Gainesville, FL (US)

(72) Inventors: Kevin H. Cuevas, Littleton, CO (US); Shravanthi T. Reddy, Goleta, CA (US); Chelsea Marie Magin, Denver, CO (US); Michael R. Mettetal, Denver, CO (US); Anthony B. Brennan, Gainesville, FL (US); Rhea Marie May, Morrison, CO (US); Ethan Eugene Mann, Aurora, CO (US)

(73) Assignees: Insight Innovations, LLC, Littleton, CO (US); Sharklet Technologies, Inc., Aurora, CO (US); University of Florida Research Foundation, Inc., Gainesville, FL (US)

(*) Notice: Subject to any disclaimer, the term of this patent is extended or adjusted under 35 U.S.C. 154(b) by 20 days.

(21) Appl. No.: 14/821,645

(22) Filed: Aug. 7, 2015

(65) Prior Publication Data
US 2015/0342725 A1 Dec. 3, 2015

Related U.S. Application Data

(63) Continuation-in-part of application No. 14/298,318, filed on Jun. 6, 2014, which is a continuation of
(Continued)

(51) Int. Cl.
*A61F 2/16* (2006.01)
*A61F 2/14* (2006.01)
*A61F 2/00* (2006.01)

(52) U.S. Cl.
CPC .......... *A61F 2/16* (2013.01); *A61F 2/14* (2013.01); *A61F 2/1601* (2015.04); *A61F 2/161* (2015.04);
(Continued)

(58) Field of Classification Search
CPC .. A61F 2/16; A61F 2/16015; A61F 2002/009; A61F 2002/1689;
(Continued)

(56) References Cited

U.S. PATENT DOCUMENTS

| 3,794,414 A | 2/1974 | Wesley |
| 3,960,150 A | 6/1976 | Hussain et al. |

(Continued)

FOREIGN PATENT DOCUMENTS

| EP | 1402851 | 3/2004 |
| EP | 2305178 | 4/2011 |

(Continued)

OTHER PUBLICATIONS

Kirschner et al. Microtopographies Inhibit Human Lens Epithelial Cell Migration in Posterior Capsule Opacification Model. 2014 Annual Meeting of Biomedical Engineering Society, Oct. 2014, San Antonio, 1 page total.
(Continued)

*Primary Examiner* — Paul Prebilic
(74) *Attorney, Agent, or Firm* — Alston & Bird LLP

(57) ABSTRACT

Generally, an intraocular implant having on the external surface a plurality of pattern surface elements disposed in spaced apart relation defining a tortuous pathway adapted to control a flow of fluid, or a flow of particles suspended in a fluid, or inhibits the growth or migration of cells. In particular, an intraocular implant which implanted between an intraocular lens and the surface of the posterior capsule of the eye inhibits growth or migration of residual lens epithe-
(Continued)

lial cells after cataract surgery by providing structural barriers to reduce posterior capsule opacification of the eye.

2 Claims, 30 Drawing Sheets

Related U.S. Application Data application No. 13/944,817, filed on Jul. 17, 2013, now Pat. No. 9,204,961, which is a continuation of application No. 13/479,178, filed on May 23, 2012, now abandoned, which is a continuation-in-part of application No. 13/136,515, filed on Aug. 2, 2011, now Pat. No. 8,551,167, which is a continuation-in-part of application No. 12/998,652, filed as application No. PCT/US2009/006165 on Nov. 19, 2009, now abandoned.

(60) Provisional application No. 61/270,567, filed on Jul. 10, 2009, provisional application No. 61/199,674, filed on Nov. 20, 2008, provisional application No. 62/034,401, filed on Aug. 7, 2014.

(52) U.S. Cl.
CPC ..... *A61F 2002/009* (2013.01); *A61L 2430/16* (2013.01)

(58) Field of Classification Search
CPC ...... A61F 2002/169; A61F 2002/16901; A61F 2/1694; A61F 2002/1696; A61F 2250/0025; A61F 2250/0026; A61F 2250/0051; A61F 2250/0052; A61F 2250/0053; A61F 2250/0091
See application file for complete search history.

(56) References Cited

U.S. PATENT DOCUMENTS

| | | | |
|---|---|---|---|
| 4,014,335 A | | 3/1977 | Arnold |
| 4,179,497 A | | 12/1979 | Cohen et al. |
| 4,441,217 A | | 4/1984 | Cozean, Jr. |
| 4,624,669 A | | 11/1986 | Grendahl |
| 4,713,072 A | | 12/1987 | Bowald |
| 4,772,419 A | | 9/1988 | Meålson et al. |
| 4,808,181 A | | 2/1989 | Kelman |
| 4,865,601 A | | 9/1989 | Caldwell et al. |
| 5,098,443 A | | 3/1992 | Parel et al. |
| 5,275,624 A | | 1/1994 | Hara et al. |
| 5,282,851 A | | 2/1994 | LaBarre |
| 5,354,331 A | | 10/1994 | Schachar |
| 5,370,687 A | * | 12/1994 | Poler .................. A61F 2/16 623/6.16 |
| 5,405,285 A | | 4/1995 | Hirano et al. |
| 5,405,385 A | | 4/1995 | Heimke et al. |
| 5,443,505 A | | 8/1995 | Wong et al. |
| 5,501,856 A | | 3/1996 | Ohtori et al. |
| 5,549,670 A | | 8/1996 | Young et al. |
| 5,593,438 A | | 1/1997 | Akhavi et al. |
| 5,618,553 A | | 4/1997 | Kelleher |
| 5,626,863 A | | 5/1997 | Hubbell et al. |
| 5,628,795 A | | 5/1997 | Langerman |
| 5,800,533 A | | 9/1998 | Eggleston et al. |
| 6,063,116 A | | 5/2000 | Kelleher |
| 6,063,396 A | | 5/2000 | Kelleher |
| 6,399,693 B1 | | 6/2002 | Brennan et al. |
| 6,485,516 B2 | | 11/2002 | Boehm |
| 6,524,340 B2 | | 2/2003 | Israel |
| 6,551,354 B1 | | 4/2003 | Ghazizadeh et al. |
| 6,554,424 B1 | | 4/2003 | Miller et al. |
| 6,616,691 B1 | | 9/2003 | Tran |
| 6,667,368 B1 | | 12/2003 | Brennan et al. |
| 6,713,081 B2 | | 3/2004 | Robinson et al. |
| 6,749,634 B2 | | 6/2004 | Hanna |
| 6,797,004 B1 | | 9/2004 | Brady et al. |
| 6,884,263 B2 | | 4/2005 | Valyunin et al. |
| 6,932,839 B1 | | 8/2005 | Kamerling et al. |
| 6,972,033 B2 | | 12/2005 | McNicholas |
| 7,025,783 B2 | | 4/2006 | Brady et al. |
| 7,037,337 B2 | | 5/2006 | Carriazo |
| 7,117,807 B2 | | 10/2006 | Brennan et al. |
| 7,143,709 B2 | | 12/2006 | Brennan et al. |
| 7,169,853 B2 | | 1/2007 | Brennan et al. |
| 7,347,970 B2 | | 3/2008 | Kim et al. |
| 7,435,258 B2 | | 10/2008 | Blake |
| 7,491,350 B2 | | 2/2009 | Silvestrini |
| 7,650,848 B2 | | 1/2010 | Brennan et al. |
| 7,806,929 B2 | | 10/2010 | Brown |
| 8,012,204 B2 | | 9/2011 | Weinschenk, III et al. |
| 8,287,592 B2 | | 10/2012 | Silvestrini |
| 8,303,655 B2 | | 11/2012 | Basoglu et al. |
| 8,308,800 B2 | | 11/2012 | Chu |
| 9,622,857 B2 | | 4/2017 | Coroneo |
| 2001/0034552 A1 | | 10/2001 | Young et al. |
| 2002/0010510 A1 | | 1/2002 | Silvestrini |
| 2003/0135272 A1 | | 7/2003 | Brady et al. |
| 2003/0144733 A1 | | 7/2003 | Brady et al. |
| 2003/0149479 A1 | | 8/2003 | Snyder et al. |
| 2004/0039446 A1 | | 2/2004 | McNicholas |
| 2004/0042073 A1 | | 3/2004 | Pynson |
| 2004/0086674 A1 | | 5/2004 | Holman |
| 2004/0127984 A1 | | 7/2004 | Paul et al. |
| 2004/0162612 A1 | | 8/2004 | Portney et al. |
| 2004/0236423 A1 | | 11/2004 | Zhang et al. |
| 2004/0243231 A1 | | 12/2004 | Koziol |
| 2005/0033420 A1 | | 2/2005 | Christie et al. |
| 2005/0119758 A1 | | 6/2005 | Alexander et al. |
| 2006/0064161 A1 | | 3/2006 | Blake |
| 2006/0235514 A1 | | 10/2006 | Silvestrini |
| 2006/0235515 A1 | | 10/2006 | Chassain |
| 2006/0265058 A1 | * | 11/2006 | Silvestrini .................. A61F 2/14 351/159.63 |
| 2007/0083260 A1 | | 4/2007 | Colvard |
| 2007/0106381 A1 | | 5/2007 | Blake |
| 2008/0077238 A1 | | 3/2008 | Deacon et al. |
| 2008/0077239 A1 | | 3/2008 | Zickler et al. |
| 2008/0241223 A1 | | 10/2008 | Nivaggioli et al. |
| 2009/0234448 A1 | | 9/2009 | Weeber et al. |
| 2010/0033818 A1 | | 2/2010 | Petcavich et al. |
| 2010/0119755 A1 | | 5/2010 | Chung et al. |
| 2010/0126404 A1 | | 5/2010 | Brennan et al. |
| 2010/0226943 A1 | | 9/2010 | Brennan et al. |
| 2011/0040376 A1 | | 2/2011 | Christie et al. |
| 2011/0098808 A1 | | 4/2011 | Kobayashi et al. |
| 2011/0230963 A1 | | 9/2011 | Cuevas |
| 2011/0295367 A1 | | 12/2011 | Cuevas |
| 2012/0058302 A1 | | 3/2012 | Eggenspieler et al. |
| 2012/0232649 A1 | | 9/2012 | Cuevas |
| 2013/0053953 A1 | | 2/2013 | Silvestrini |
| 2013/0053954 A1 | | 2/2013 | Rao et al. |
| 2013/0153612 A1 | | 6/2013 | O'Brien et al. |
| 2013/0304205 A1 | | 11/2013 | Cuevas |
| 2016/0074154 A1 | | 3/2016 | Woods |
| 2016/0081792 A1 | | 3/2016 | Cuevas |

FOREIGN PATENT DOCUMENTS

| | | | | |
|---|---|---|---|---|
| FR | 2 832 920 | | 6/2003 | |
| FR | 2 832 920 A1 | | 6/2003 | |
| WO | WO 9208422 A1 | * | 5/1992 | ........... A61F 2/1613 |
| WO | WO 93/09732 | | 5/1993 | |
| WO | WO 2008/108523 | | 9/2008 | |
| WO | WO 2010/059214 | | 5/2010 | |
| WO | WO 2013/019871 | | 2/2013 | |
| WO | WO-2016/022933 | | 2/2016 | |

OTHER PUBLICATIONS

Magin et al. Micropatterned Protective Membranes Inhibit Lens Epithelial Cell Migration in Posterior Capsule Opacification Model.

(56) References Cited

OTHER PUBLICATIONS

Translational Vision Science & Technology, Mar. 2015, 4(2): 9, 8 pages total.
PCT International Patent Application No. PCT/US2015/044357; International Search Report and Written Opinion of the International Search Authority dated Feb. 1, 2016, 8 pages total.
U.S. Appl. No. 61/199,674, filed Nov. 20, 2008.
U.S. Appl. No. 61/270,567, filed Jul. 10, 2009.
International Patent Cooperation Treaty Patent Application No. PCT/US2009/006195, filed Nov. 19, 2009.
International Patent Cooperation Treaty Patent Application No. PCT/US12/49176, filed Aug. 1, 2012.
Cleary et al.Effect of Square-edged Intraocular Lenses on Neodymium:YAG Laser Capsulotomy Rates in the United States.J. Cataract&Refractive Surgery,vol. 13,Nov. 2007,p. 1899-906.
Cortina et al. Diclofenac Sodium and Cyclosporine A Inhibit Human Lens Epithelial Cell Proliferation in Culture.Graefes Arch Clin Exp Ophthalmol,vol. 235,Mar. 1997,pp. 180-185.
Emery. Capsular Opacification After Cataract Surgery. Curr Opin in Ophthalmol, vol. 10, 1999, pp. 73-80.
Hara et al.Long-Term Study of Posterior Capsular Opacification Prevention With Endocapsular Equator Rings in Humans. Arch Ophthalmol,Jul. 2011, vol. 129(7), pp. 855-863.
Hartmann et al. Prevention of Secondary Cataract by Intracapsular Administration of the Antibiotic Daunomycin. Ophthalmol, vol. 4, Jan. 1990, pp. 102-106.
Inan et al. Effect of Diclofenac on Prevention of Posterior Capsule Opacification in Human Eyes. Can J Ophthalmol, vol. 41, Oct. 2006, pp. 624-629.
Inan et al. Prevention of Posterior Capsule Opacification by Retinoic Acid and Mitomycin. Graefes Arch Clin Exp Ophthalmol, Aug. 2001, vol. 239, pp. 693-697.
Inan et al. Prevention of Posterior Capsule Opacification by Intraoperative Single-dose Pharmacologic Agents. J Cataract Refract Surg, vol. 27, Jul. 2001, pp. 1079-1087.
Ismail et al. Prevention of Secondary Cataract by Antimitotic Drugs: Experimental Study. Ophthalmic Res, 1996, vol. 28(1), pp. 64-69.
Kavoussi, et al. Prevention of Capsular Bag Opacification with a New Hydrophilic Acrylic Disk-Shaped Intraocular Lens.J Cataract Refract Surg, Dec. 2011, 37, pp. 2194-2200.
Maloof et al. Selective and Specific Targeting of Lens Epithelial Cells During Cataract Surgery Using Sealed-Capsule Irrigation. J Cataract Refract Surg, Aug. 2003, vol. 29, pp. 1566-1568.
Oberleithner et al. Fusion of renal epithelial cells: A model of studying cellular mechanisms of ion transport. Proc. Natl. Acad. Sci. USA, May 1986, vol. 83, pp. 3547-3551.
Osnsupersite. New Accommodating IOL Offers High Rate of Spectacle Independence; Website, http://www.osnsupersite.com, originally downloaded Apr. 4, 2012, 3 total pages.
Tekia. Website, http://tekia.com, originally downloaded Apr. 4, 2012, 1 page.
U.S. Appl. No. 12/998,652; Office Action mailed Aug. 7, 2012.
U.S. Appl. No. 12/998,652; Office Action mailed Aug. 27, 2012.
U.S. Appl. No. 12/998,652; Office Action mailed Mar. 18, 2013.
U.S. Appl. No. 13/136,515; Office Action mailed Dec. 17, 2012.
U.S. Appl. No. 13/136,515; Office Action mailed Feb. 13, 2013.
Corresponding EP patent application No. 09827868.2; Office Action mailed Mar. 6, 2013, 7 total pages.
Bluestein, et al. Dimensions of the Pediatric Crystalline Lens: Implications for Intraocular Lenses in Children. J Pediatr Ophthalmol Strabismus, Jan.-Feb. 1996, 33(1), pp. 18-20.
Menlyweb. Andre "The Giant" Roussimoff. Website, http://www.manlyweb.com, Dec. 2007, 3 total pages.
Noardi. Eye Size Chart. Website, http://www.noardi.net, Aug. 2013, 4 total pages.
Roarty, et al. Normal pupil size and anisocoria in newborn infants. Arch Ophthalmol, Jan. 1990, 108(1):94-95.
Leishman et al. Prevention of capsular bag opacification with a modified hydrophilic acrylic disk-shaped intraocular lens. J Cataract Refract Surg,Sep. 2012,38:1664-1670.
Werner et al. Experimental evaluation of ophthalmic devices and solutions using rabbit models. Veterinary Ophthalmology, Sep. 2006, 9, 5, pp. 281-291.
Melki et al. An implantable intraocular pressure transducer: Initial safety outcomes. JAMA Ophthalmology, Oct. 2014, vol. 132, No. 10, pp. 1221-1225.
European Patent Application No. 12820279.3; Office Action dated Jan. 27, 2015, 10 total pages.
Corresponding Europepan Patent Application No. 09827868.2; Response to Office Action filed Feb. 24, 2014, 17 total pages.
U.S. Appl. No. 14/298,318, filed Jun. 6, 2014.
U.S. Appl. No. 62/034,401, filed Aug. 7, 2014.
Reddy et al.; "Micro-Patterned Surfaces for Reducing Bacterial Migration Associated with Catheter-Associated Urinary Tract Infection"; American Journal of Infection Control; 39(5); 2011, E37-38 (Jun. 2011).
Reddy et al.;"Micropatterned Sufaces for Reducing the Risk of Catheter-Associated Urinary Tract Infection:An In Vitro Study on the Effect of Sharklet Micropatterned Surfaces to Inhibit. . . ", Journal of Endourology, V. 25, No. 9, 2011,1547-1552 Sep. 2011.
"Sharklet." [retrieved Jul. 31, 2017]. Retrieved via the Internet Archive Wayback Machine at <URL: https://web.archive.org/web/20110716052836/http://www.sharklet.com/>. (Jul. 16, 2011) 4 pages.
Office Action for corresponding European Patent Application No. 09827868.2 dated Aug. 29, 2013, 6 pages.
Office Action for corresponding European Patent Application No. 09827868.2 dated Mar. 25, 2015, 8 pages.
International Search Report and Written Opinion of International Searching Authority for International Patent Application No. PCT/US2015/044238 dated Nov. 11, 2015, 11 pages.
Extended European Search Report for European Patent Application No. 16186404.6 dated Dec. 22, 2016, 8 pages.

\* cited by examiner

FIG. 3
FIG. 4
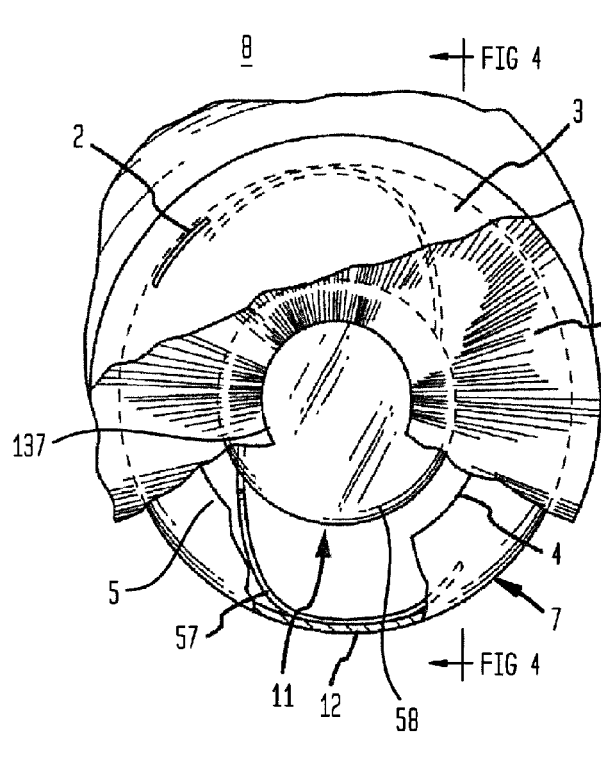
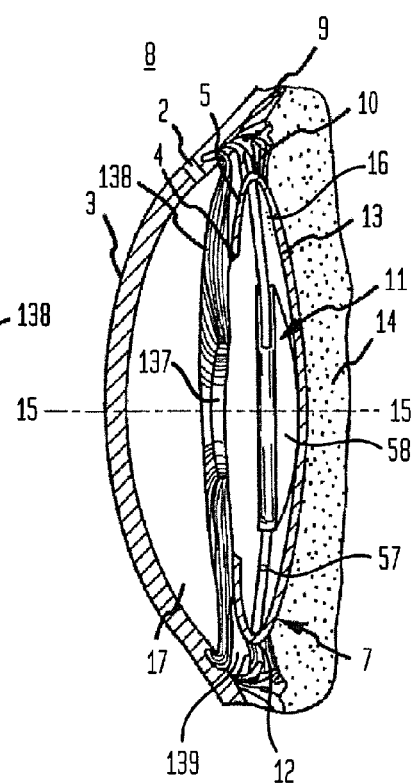

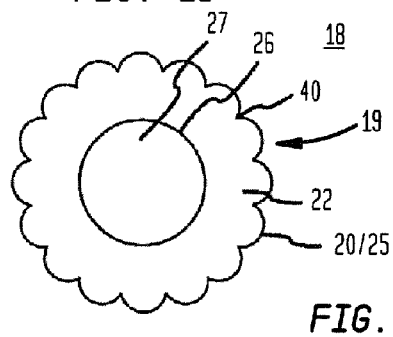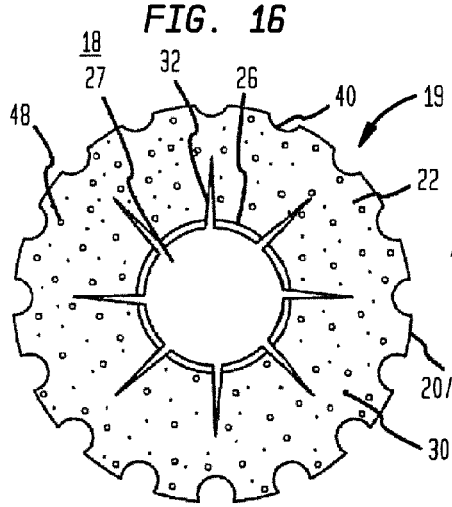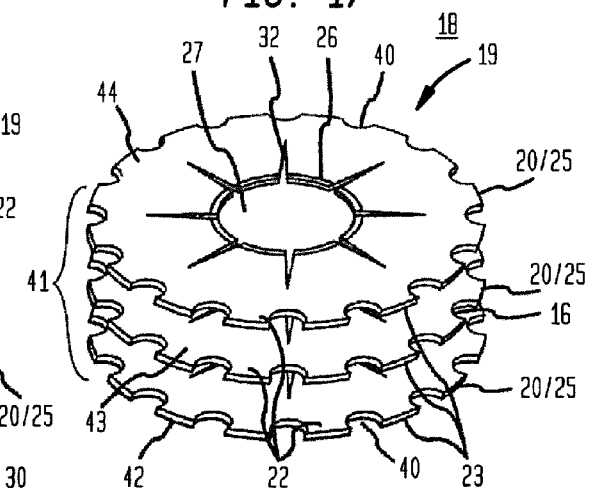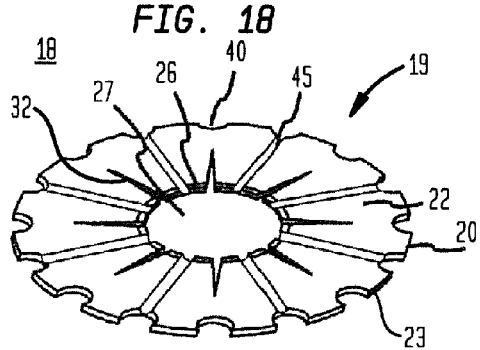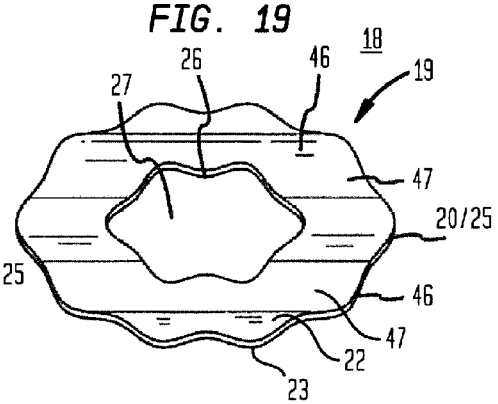

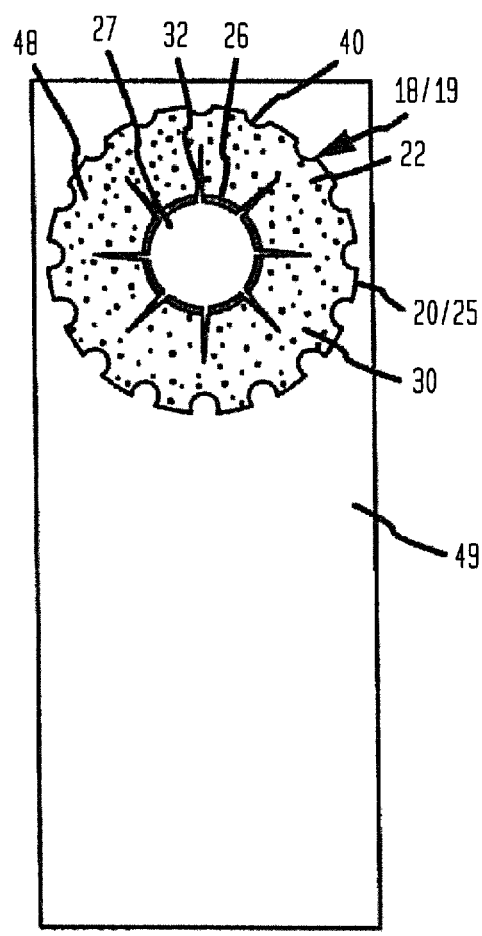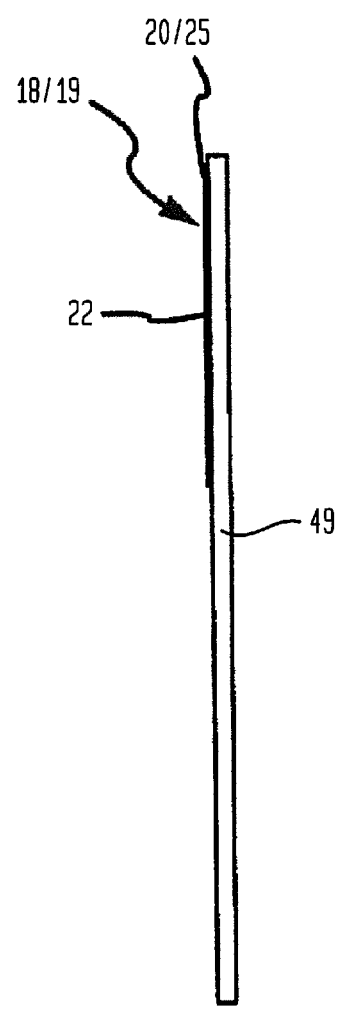

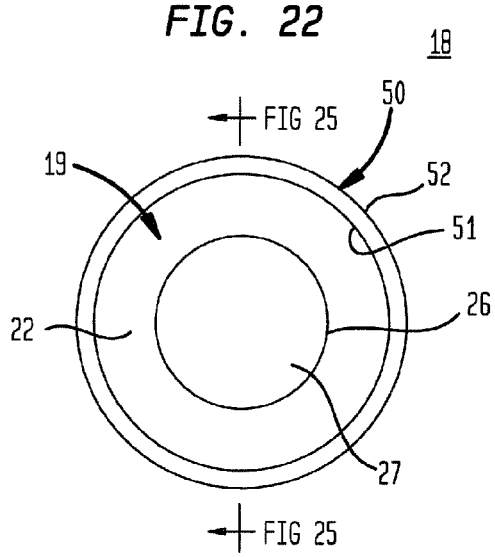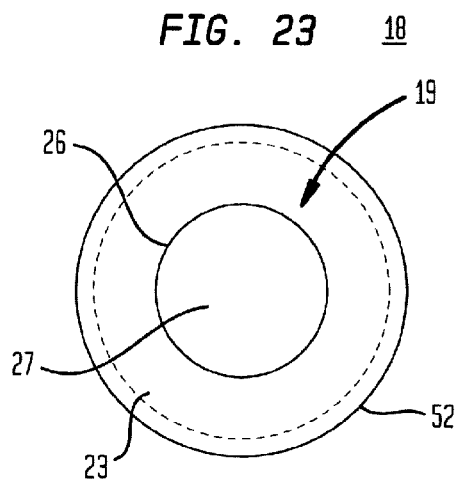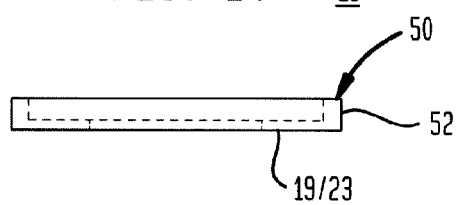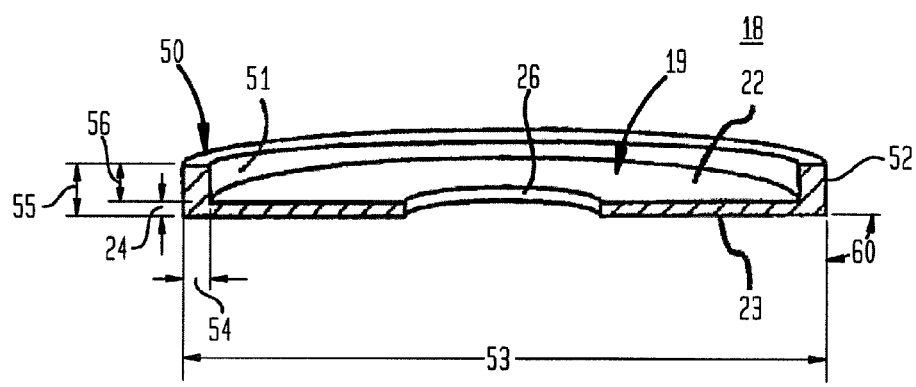

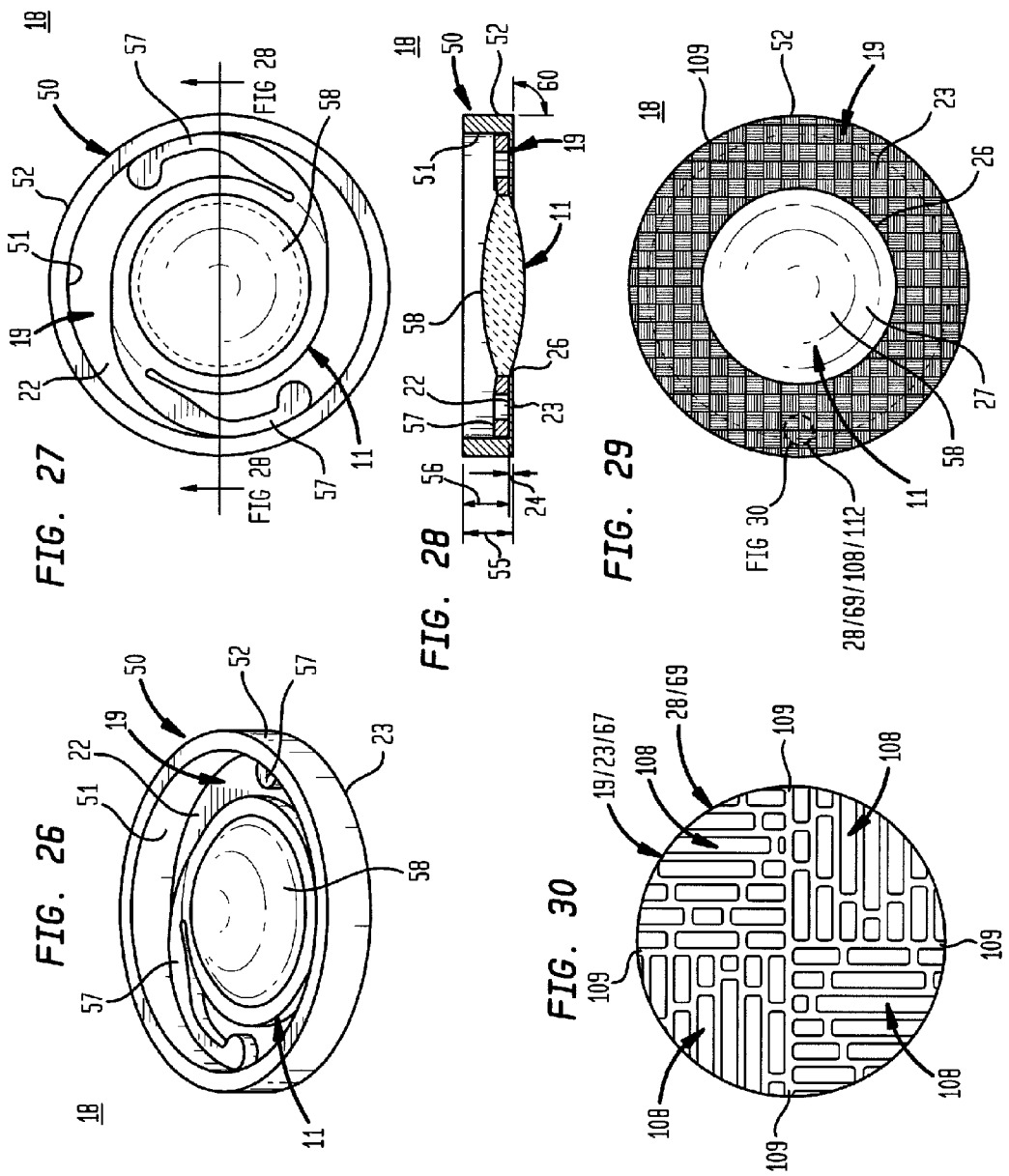

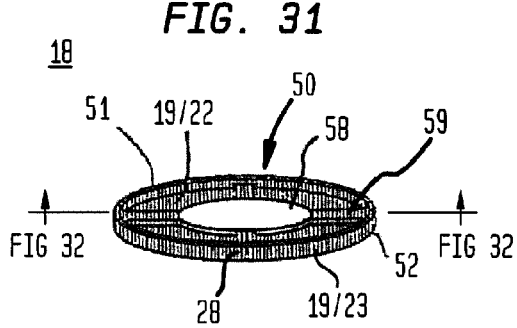
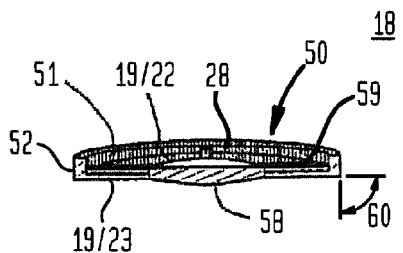
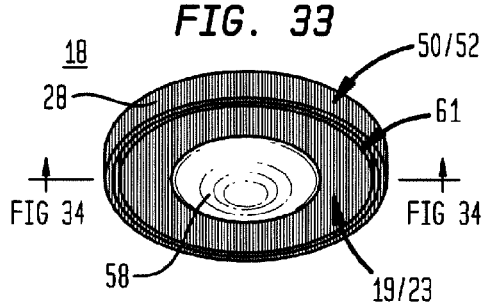
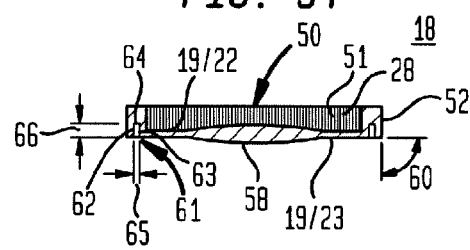
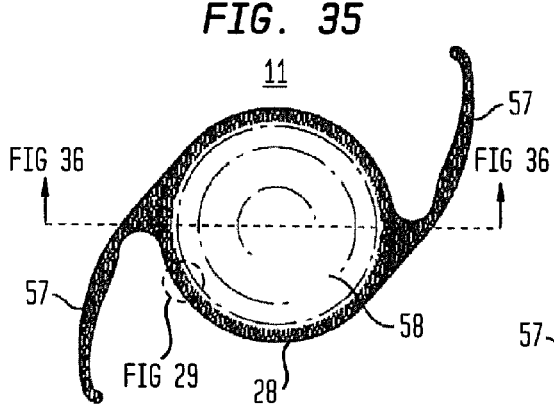
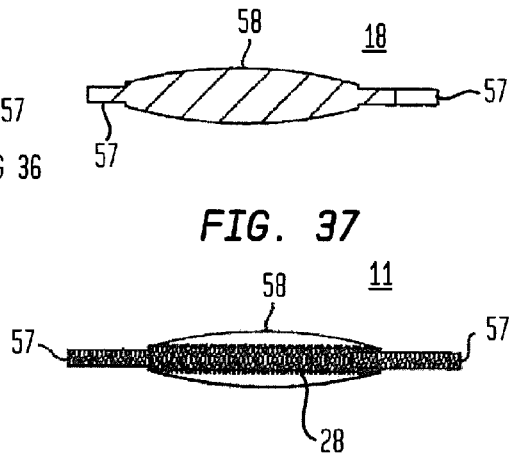
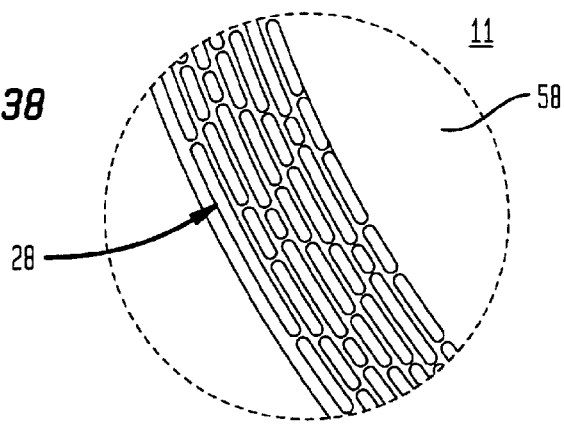

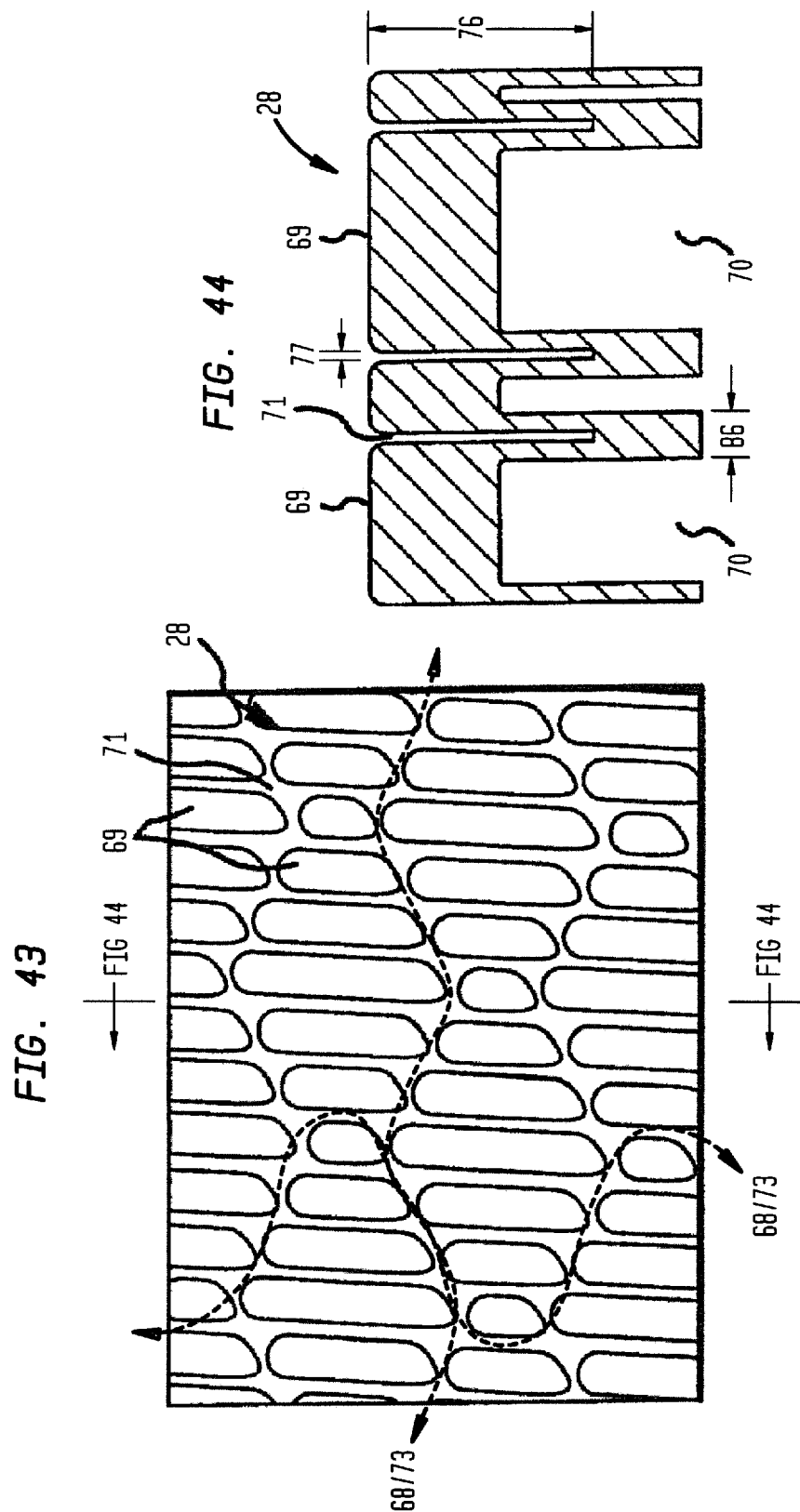

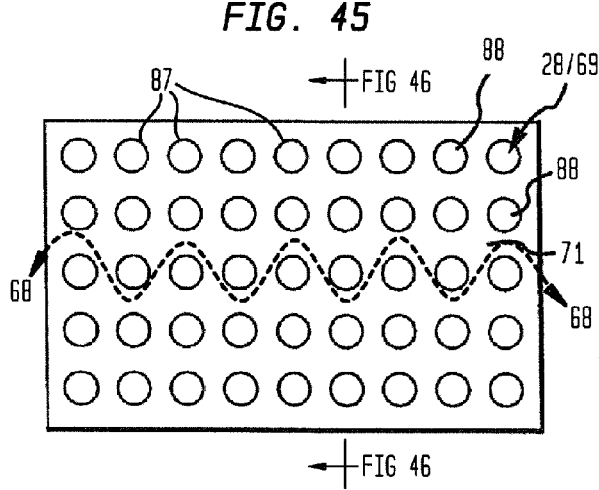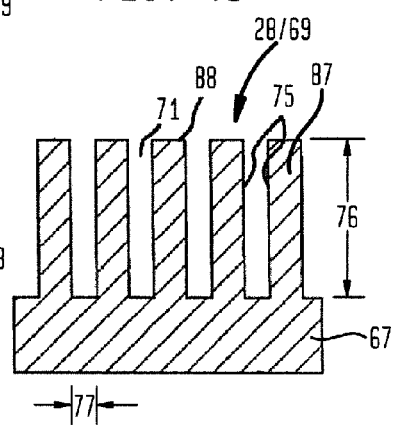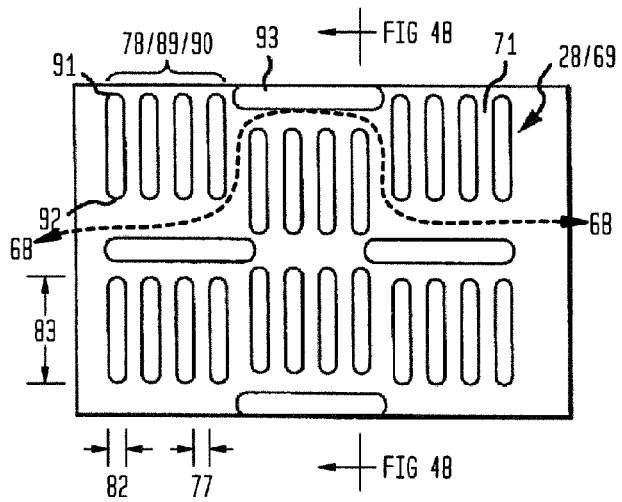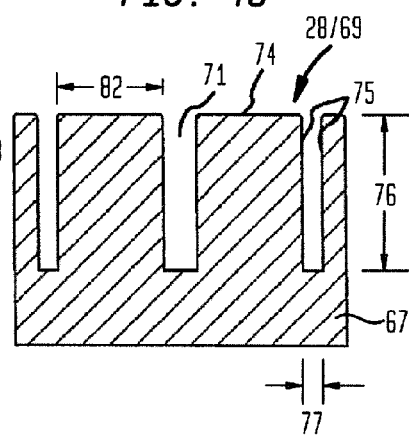

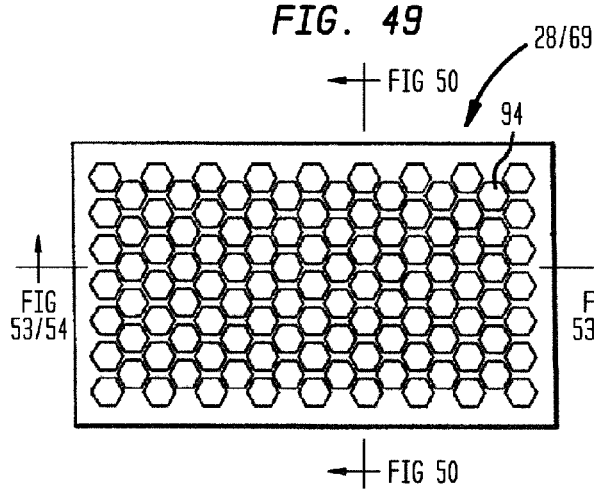
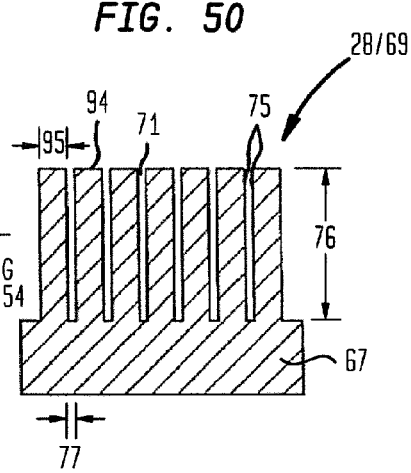
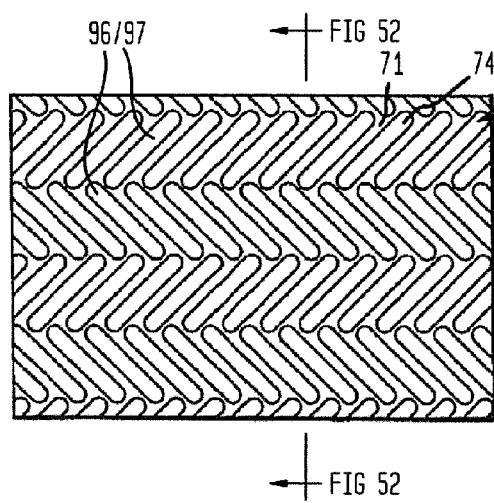
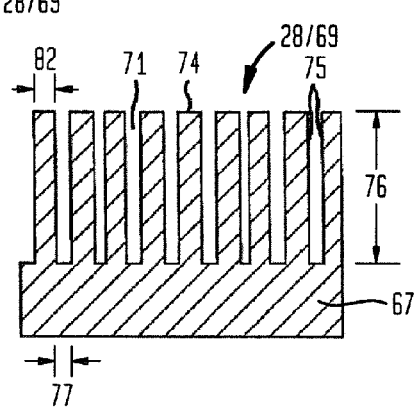

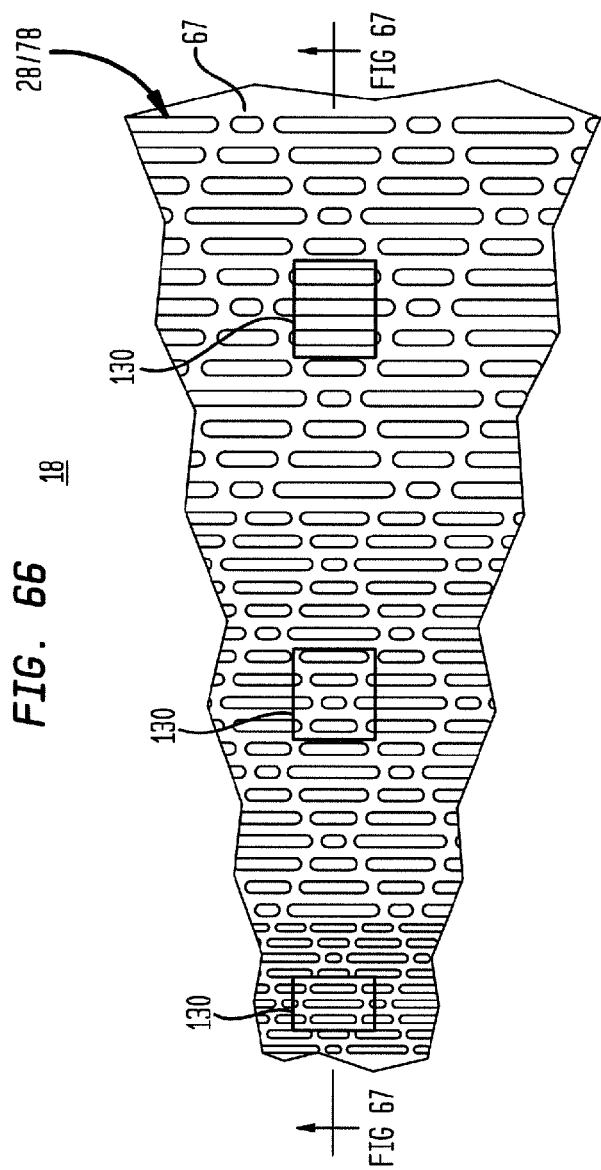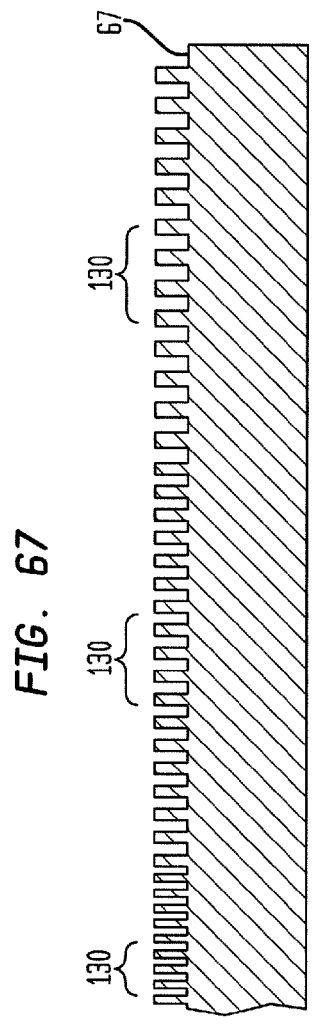

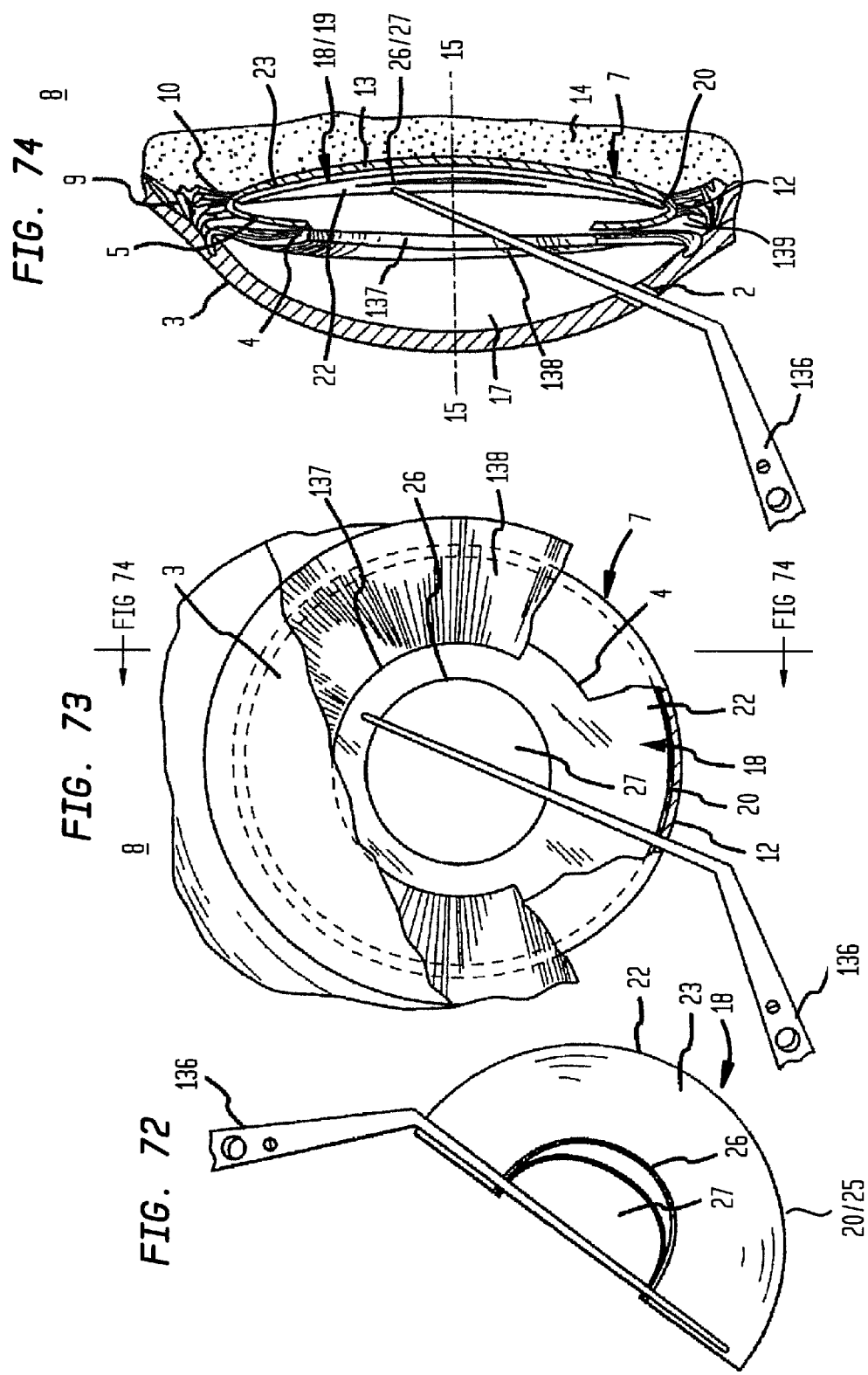

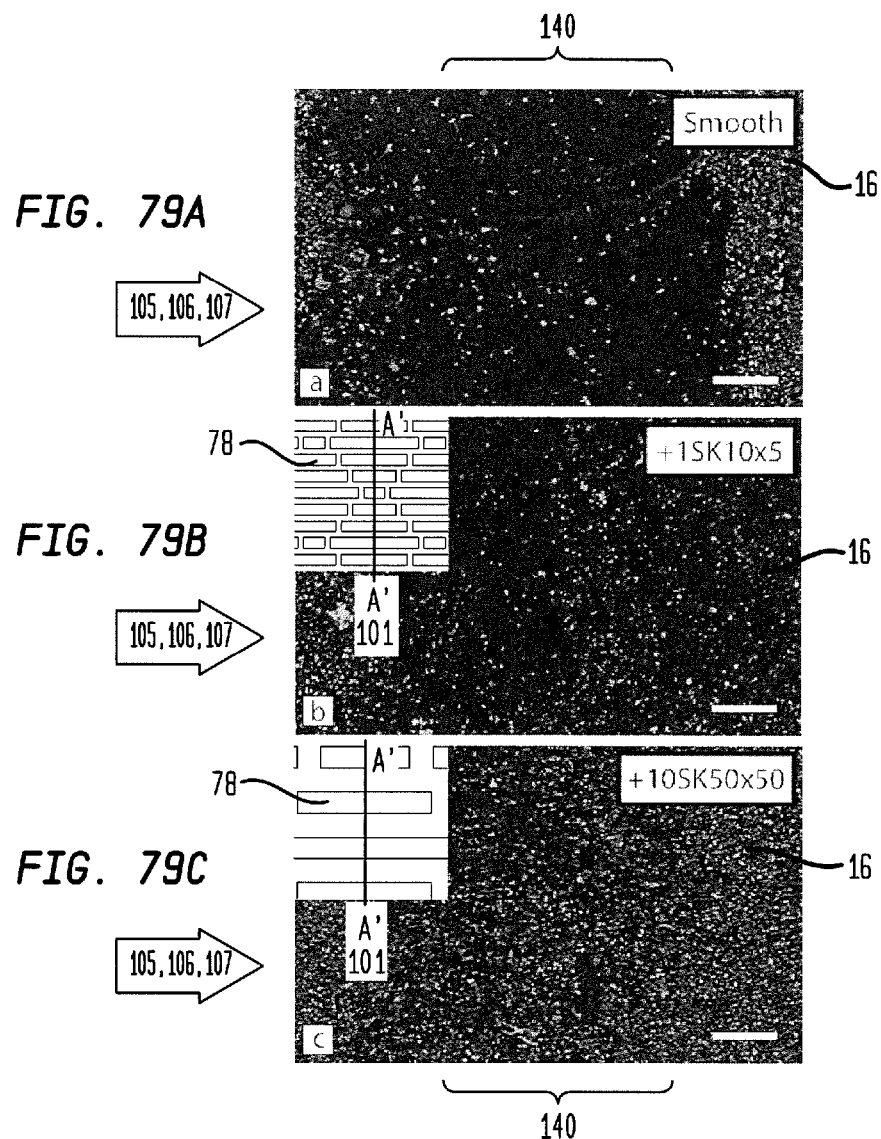
FIG. 79A
FIG. 79B
FIG. 79C
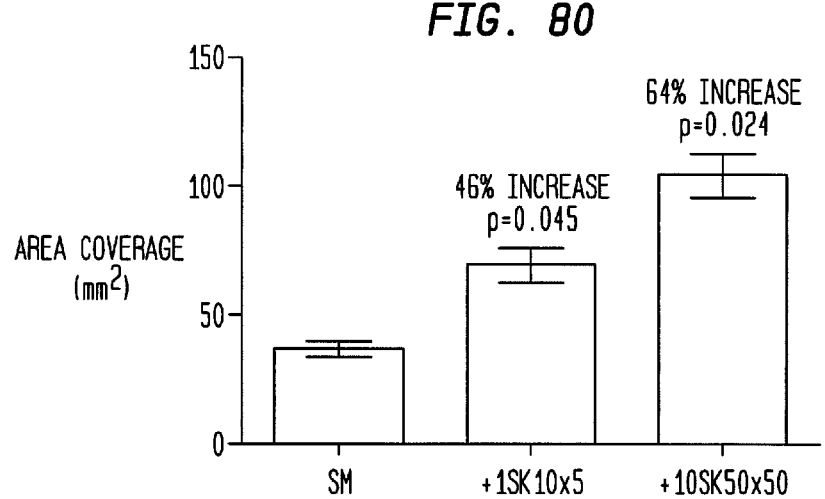
FIG. 80

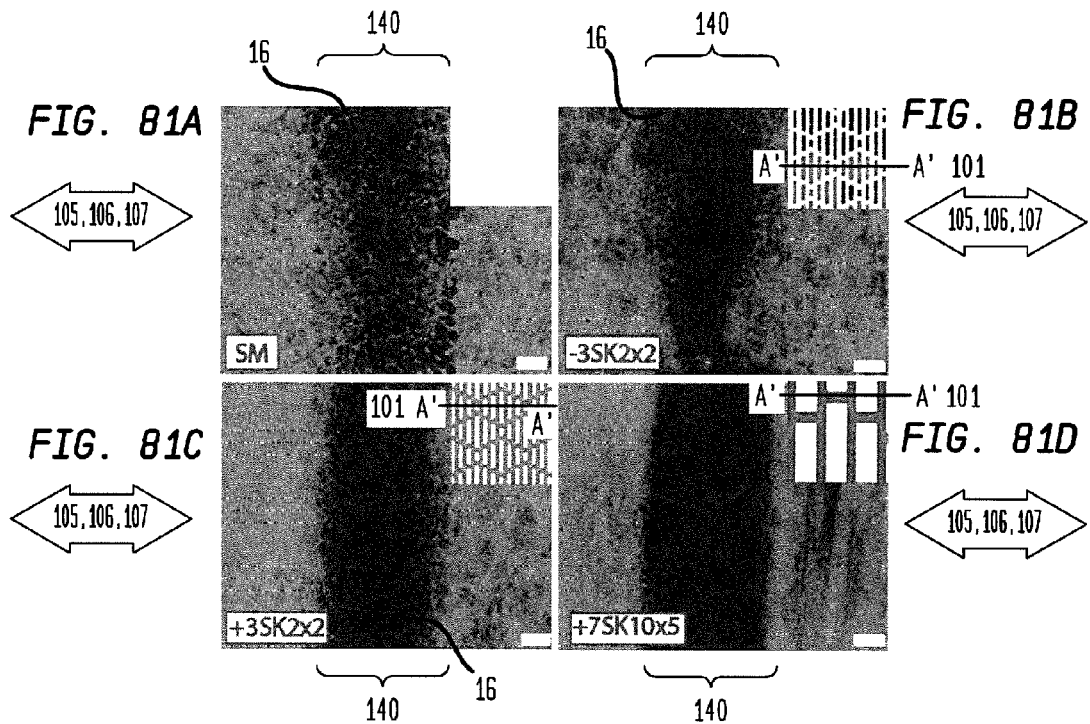
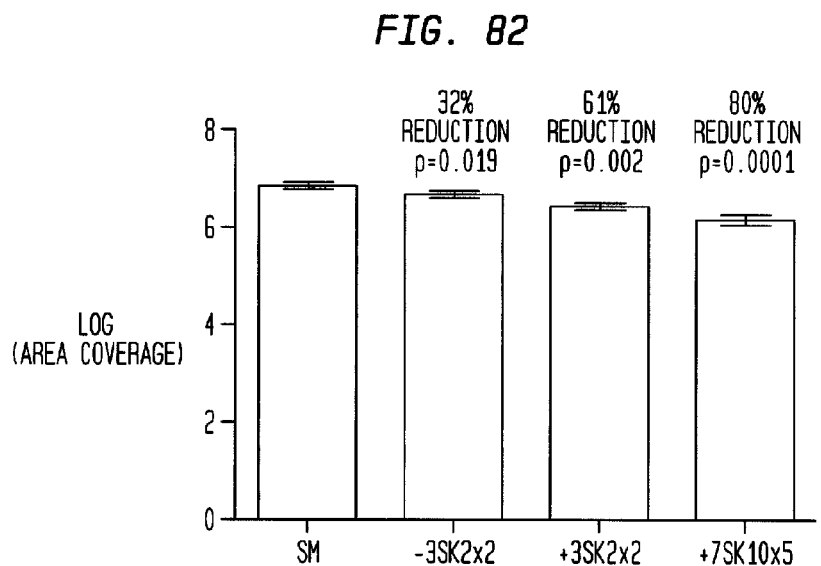

FIG. 83A  FIG. 83B  FIG. 83C
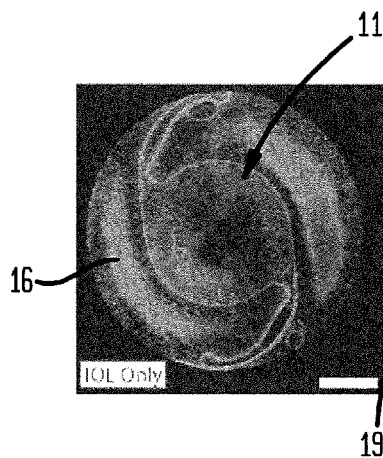 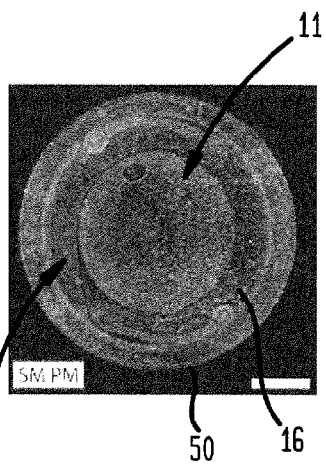 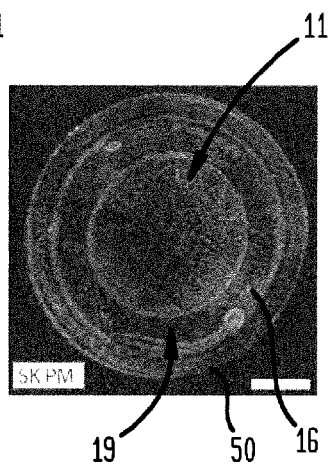
FIG. 84
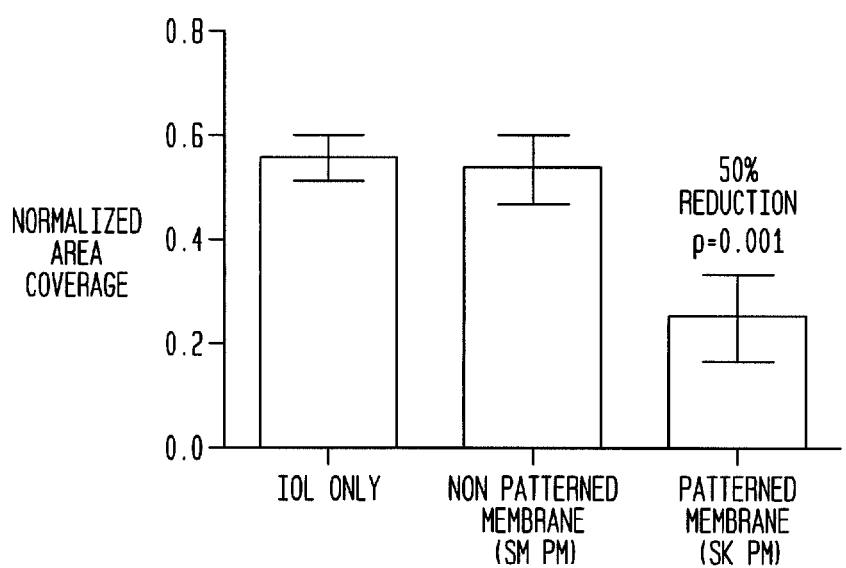

FIG. 85A   FIG. 85B   FIG. 85C
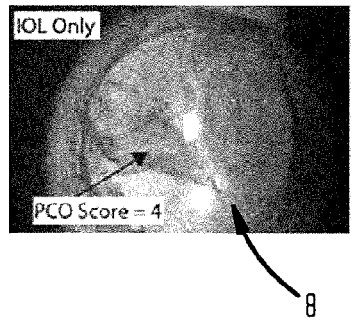 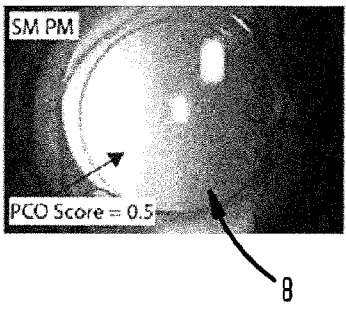 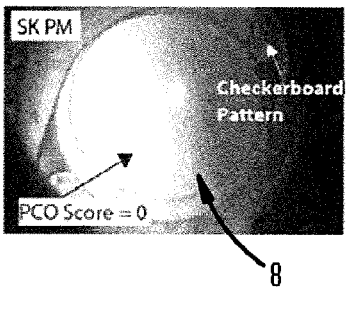
FIG. 86
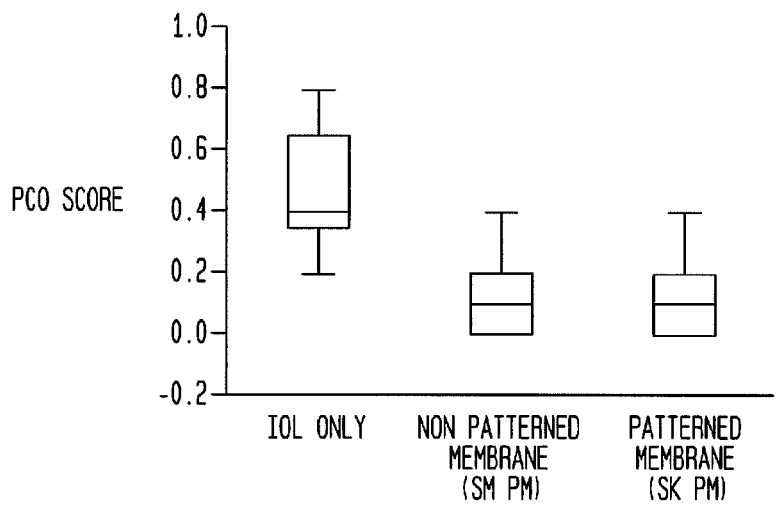
FIG. 87
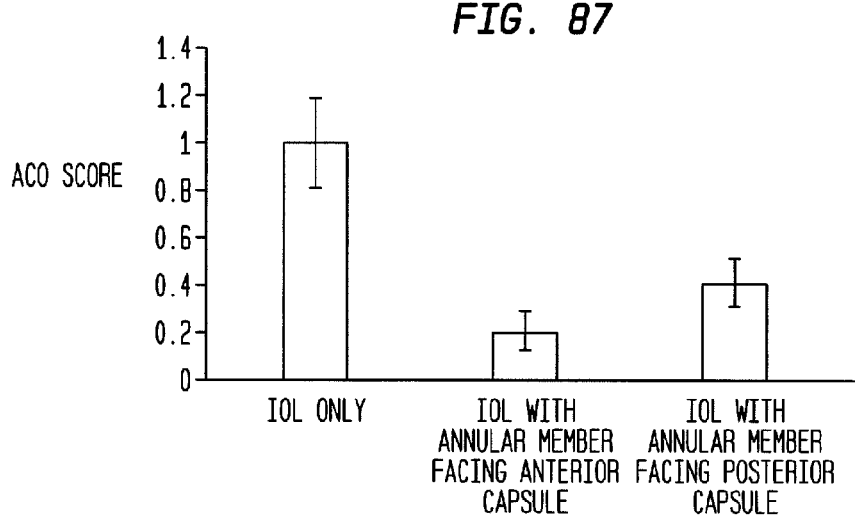

MICROPATTERNED INTRAOCULAR IMPLANT

This United States Patent Application is a continuation-in-part of U.S. patent application Ser. No. 14/298,318, filed Jun. 6, 2014, which is a continuation of U.S. patent application Ser. No. 13/944,817, filed Jul. 17, 2013, now U.S. Pat. No. 9,204,961 which is a continuation of U.S. patent application Ser. No. 13/479,178, filed May 23, 2012, which is a continuation-in-part of U.S. patent application Ser. No. 13/136,515, filed Aug. 2, 2011, now abandoned now U.S. Pat. No. 8,551,167, issued Oct. 8, 2013, which is a continuation-in-part of U.S. patent application Ser. No. 12/998,652, filed May 13, 2011, which is a United States National Stage of International Patent Cooperation Treaty Patent Application No. PCT/US2009/006195, filed Nov. 19, 2009, which claims the benefit of United States Provisional Patent Application 61/270,567, filed Jul. 10, 2009 and U.S. Provisional Patent Application No. 61/199,674, filed Nov. 20, 2008, and claims the benefit of U.S. Provisional Patent Application 62/034,401, filed Aug. 7, 2014, each hereby incorporated by reference herein.

I. FIELD OF THE INVENTION

Generally, an intraocular implant having on the external surface a plurality of pattern surface elements disposed in spaced apart relation defining a tortuous pathway adapted to control a flow of fluid, or a flow of particles suspended in a fluid, or inhibits the adhesion, growth or migration of cells. In particular, an intraocular implant which implanted between an intraocular lens and the surface of the posterior capsule of the eye inhibits growth or migration of residual lens epithelial cells after cataract surgery by providing structural barriers to reduce posterior capsule opacification of the eye.

II. BACKGROUND OF THE INVENTION

Visually impairing cataract is the leading cause of preventable blindness in the world. Presently, the only known treatment for cataract is the surgical removal of the opacified lens of the affected eye and replacement with an artificial intraocular lens, typically including an intraocular lens optic and haptics ("IOL"). Technological advances in cataract surgery with IOL implantation have made cataract surgery among the most effective surgical procedures.

Now referring primarily to FIGS. 1 and 2, which show a top view and a cross section view of a phakic eye (1). The most common technique of cataract surgery may be extracapsular cataract extraction ("ECCE") which involves the creation of an incision (2) near the outer edge of a cornea (3) and a circular opening (4)(shown in FIGS. 3 and 4) in an anterior lens capsule (5)(also referred to as the "anterior capsule") through which the opacified natural lens (6) can be removed from the lens capsule (7)(also referred to as the "capsular bag"). Now referring primarily to FIGS. 3 and 4 which show a top view and a cross section view of a pseudophakic eye (8), the lens capsule (7) anchored to the ciliary body (9) through the zonular fibers (10) can be left substantially intact. An IOL (11) can then be placed within the lens capsule (7) through the circular opening (4) in the anterior capsule (5). The IOL (11) can be acted on by zonular forces exerted on the outer circumference (12) of the lens capsule (7) which establishes the location of the IOL (11) within the lens capsule (7). The intact posterior capsule (13) acts as a barrier to the vitreous humor (14) within the posterior segment of the phakic or pseudophakic eye (1)(8).

The most frequent complication to ECCE and other methods of cataract surgery can be opacification of the posterior capsule (13). Posterior capsule (13) opacification ("PCO") results from the migration of residual lens epithelial cells ("LEC")(16) between the IOL (11) and the surface of the posterior capsule (13) subsequent to cataract surgery. The residual LECs (16) once located between the IOL (11) and the surface of the posterior capsule (13) can proliferate leading to clouding of the normally clear posterior capsule (13). Clouding of the posterior capsule (13) can decrease visual acuity, if the opacification occurs within the visual axis (15) of the pseudophakic eye (8).

Visually significant PCO requires an additional surgery to clear the visual axis (15) of the pseudophakic eye (8). Presently, the most widely utilized procedure to clear the visual axis (15) of PCO may be Neodymium: Yttrium-Aluminum-Garnet ("Nd:YAG") laser capsulotomy. However, there may be substantial problems with this procedure such as IOL (11) damage, postoperative intraocular pressure spikes, vitreous floaters, cystoid macular edema, retinal detachment, and IOL (11) subluxation, or the like. Additionally, pediatric patients can be difficult to treat and a delay in treatment can lead to irreversible amblyopia. Many underdeveloped countries do not have access to a Nd:YAG laser and the cost can be prohibitive.

Prevention or inhibition of PCO fall into two broad categories: mechanical and pharmacological. Mechanical mechanisms to inhibit PCO have primarily focused on configuration of the IOL (11). Configuring the IOL (11) to include a sharp posterior edge may provide a structural barrier to the migration of residual LECs (16) between the IOL (11) and the surface of the posterior capsule (13). Cleary et al., Effect of Square-edged Intraocular Lenses on Neodymium: YAG Laser Capsulotomy Rates in the United States, J. Cataract & Refractive Surgery, Vol. 33, p. 1899-1906 (November 2007). However, while introduction of square edged IOLs (11) appears to have reduced incidence of PCO, a review of Medicare claims data from 1993 to 2003 evidences that the number of laser capsulotomies performed in the United States to treat PCO in recipients of square edged IOL (11) remains substantial.

Pharmacological mechanisms have been proposed as a way to inhibit or prevent PCO. The effect of topical treatment with nonsteroidal anti-inflammatory drugs ("NSAIDs") such as diclofenac and indomethacin after phacoemulsification do not appear to inhibit PCO. Inan et al., Effect of Diclofenac on Prevention of Posterior Capsule Opacification in Human Eyes, Can J Ophthalmol, 41; 624-629 (2006). Additionally, the majority of pharmacological agents tested in-vitro for inhibition of migration and proliferation of LECs (16) are antimetabolites and antimitotics which have not been used clinically because of their toxic side effects. Inan U U, Ozturk F, Kaynak S, et al. Prevention of Posterior Capsule Opacification by Intraoperative Single-dose Pharmacologic Agents, J Cataract Refract Surg, 27:1079-87(2001); Inan U U, Ozturk F, Kaynak S. Ilker S S, Ozer E, Güder, Prevention of Posterior Capsule Opacification by Retinoic Acid and Mitomycin, Graefes Arch Clin Exp Ophthalmol 239: 693-7(2001); Cortina P, Gomez-Lechon M J, Navea A, Menezo J L, Terencio M C, Diaz-Llopis, M, Diclofenac Sodium and Cyclosporine A Inhibit Human Lens Epithelial Cell Proliferation in Culture, Graefes Arch Clin Exp Ophthalmol 235: 180-5(1997); Ismail M M, Alio J L, Ruiz Moreno J M, Prevention of Secondary Cataract by Antimitotic Drugs: Experimental Study, Ophthalmic Res, 28:64-9 (1996); Emery J., Capsular Opacification After Cataract Surgery, Curr Opin Ophthalmol, 10:73-80 (1999); Hartmann C, Wiedemann P, Gothe K, Weller M, Heimann K, Prevention of Secondary Cataract by Intracapsular Administration of the Antibiotic Daunomycin, Ophthalmologie, 4:102-6 (1990).

Also, available is a sealed capsule irrigation device which functions to allow selective irrigation of the lens capsule (7) with LEC (16) inhibiting pharmacologic agents. Maloof A J, Neilson G, Milverton E J, Pandy S K, Selective and specific targeting of lens epithelial cells during cataract surgery using sealed-capsule irrigation, J Cataract Refract Surg, 29:1566-68 (2003). It is not clear, however, that use of the device can be reduced to routine practice. Problems relating to incomplete seal of the lens capsule (7) resulting in leakage of potentially toxic chemicals into the anterior chamber (17) of the pseudophakic eye (8), rupture of the lens capsule (7) during manipulation of the irrigation device, difficulty in assessing kill of LECs (16) within the lens capsule (7) and an increase in the duration of routine cataract surgery limit the usefulness of the irrigation device.

Another prominent problem with routine cataract surgery and other surgical procedures such as retinal surgery, cornea transplant surgery, glaucoma surgery, or the like, can be postoperative administration of antibiotics to prevent endophthalmitis. Topical antibiotic and anti-inflammatory eye drops represent the mainstay of drug delivery for intraocular surgery. However, there has yet to be a prospective randomized study showing that topical antibiotics prevent endophthalmitis. Also, because the human cornea acts as a natural barrier to biologic and chemical insults, intraocular bioavailability usually requires frequent dosing regimens for each medication. Topical drops can be difficult for young and elderly patients and the drop schedule can be cumbersome and confusing particularly when following surgery each eye (1)(8) is on a different drop schedule. These difficulties can result in non-compliance with serious consequences such as endophthalmitis, glaucoma, and cystoid macular edema. Recent prospective studies supporting the use of intracameral antibiotic injections for prophylaxis of endophthalmitis have stirred debate regarding the risks associated with this method of antibiotic prophylaxis including the short duration of protective effect (possibly less than 24 hours), the introduction of potentially contaminated substances in the anterior chamber (17), endothelial cell toxicity, toxic anterior segment syndrome, dilutional and osmolarity errors during mixing, and the like. Also, the systemic administration of drugs for treatment of localized ocular conditions may not be preferred because of the inefficiency associated with indirect delivery of the drugs to a target organ.

Recognizing these disadvantages of conventional delivery of antibiotics and other drugs to the eye (1)(8), external ocular inserts were developed utilizing biologically inert materials to act as a reservoir for slow release of the drug. These external ocular inserts may be placed within the upper and lower conjunctival fornix of the eye (1)(8) to achieve a uniform sustained rate of release of drug in therapeutically effective amounts. However, patients can be intolerant of these devices due to difficulty in insertion and removal and mild to moderate conjunctival irritation during use which may explain why external ocular inserts have not been widely accepted in clinical practice.

III. SUMMARY OF THE INVENTION

Accordingly, a broad object of the invention can be to provide a biocompatible intraocular implant configured for implantation in a localized region of the eye having an external surface including a plurality of pattern surface elements (also referred to as "surface elements") disposed in spaced apart relation defining a tortuous pathway which traverses the plurality surface elements adapted to control the flow of fluid, the flow of particles suspended in a fluid flow, or inhibits the growth or migration of cells.

Another broad object of the invention can be to provide a biocompatible intraocular implant having a plurality of patterned surface elements which intraocularly implanted between an IOL and the surface of the posterior capsule of the eye provides a mechanical barrier which inhibits migration of residual LECs after cataract surgery for treatment of PCO.

Another broad object of the invention can be to provide a biocompatible intraocular implant and methods of treatment of an ocular condition by implantation of a biocompatible intraocular implant inside the eye with embodiments which can be intraocularly implanted in the posterior capsule of the eye to provide mechanical or pharmaceutical barriers to interrupt progression of the ocular condition, in the ciliary sulcus between the iris and the lens, or in the anterior chamber overlaying the iris.

Another broad object of the invention can be to provide a biocompatible intraocular implant locatable between the surface of the posterior capsule of the eye and an implanted IOL to provide a mechanical barrier which inhibits growth or migration of residual lens epithelial cells after cataract surgery by providing structural barriers to reduce posterior capsule opacification of the eye.

Another broad object of the invention can be to provide a biocompatible biodegradable intraocular implant locatable between the surface of the posterior capsule of the eye and an implanted IOL to provide a biodegradable mechanical barrier for treatment of an ocular condition.

Another broad object of the invention can be to provide a biocompatible biodegradable intraocular implant locatable between the surface of the posterior capsule of the eye and an implanted IOL which includes a biocompatible biodegradable material which continually, or substantially continually, releases a therapeutically effective amount of an active agent to treat an ocular condition.

Another broad object of the invention can be to provide a biocompatible biodegradable intraocular implant locatable between the surface of the posterior capsule of the eye and an implanted IOL during cataract surgery which by mechanical or pharmaceutical barriers inhibits migration of residual lens epithelial cells on the surface of the posterior capsule.

Another broad object of the invention can be to provide a biocompatible biodegradable intraocular implant locatable between the surface of the posterior capsule of the eye and an implanted IOL during cataract surgery which by mechanical or pharmaceutical barriers inhibits proliferation of residual lens epithelial cells to the surface of the posterior capsule as a prophylaxis of PCO.

Another broad object of the invention can be to provide a biocompatible or biocompatible biodegradable intraocular implant locatable anterior to the natural crystalline lens or an implanted IOL within the ciliary sulcus for administration of one or more active agents.

Another broad object of the invention can be to provide a biocompatible or biocompatible biodegradable intraocular implant locatable in the anterior chamber overlaying the iris.

Naturally, further objects of the invention are disclosed throughout other areas of the specification, drawings, photographs, and claims.

IV. BRIEF DESCRIPTION OF THE DRAWINGS

FIG. 3 is a top view of the pseudophakic eye having the natural lens replaced with an IOL.

FIG. 4 is a cross section 4-4 of the pseudophakic eye having the natural lens replaced with an IOL.

FIG. 15 is a front view of a particular embodiment of the inventive intraocular implant which further provides one or more boundary recess elements.

FIG. 16 is a front view of a particular embodiment of the inventive intraocular implant which includes both radial slit elements originating from the aperture element and boundary recess elements which periodically interrupt the outer boundary.

FIG. 17 is a perspective view of a particular embodiment of the inventive intraocular implant including a plurality of layer stacked front to back.

FIG. 18 is a perspective view of an embodiment of the inventive intraocular implant which includes radial capillary elements.

FIG. 19 is a perspective view of an embodiment of the inventive intraocular implant which includes corrugate elements.

FIG. 20 is a front view of an embodiment of the intraocular implant affixed to a packaging substrate in the form of a sterile card prior to implantation.

FIG. 21 is a side view of an embodiment of the intraocular implant affixed to a packaging substrate in the form of a sterile card prior to implantation.

FIG. 22 is a front view of a particular embodiment of the inventive intraocular implant of generally circular configuration which terminates radially in an annular member.

FIG. 23 is a back view of a particular embodiment of the inventive intraocular implant of generally circular configuration which terminates radially in an annular member.

FIG. 24 is a side view of a particular embodiment of the inventive intraocular implant of generally circular configuration which terminates radially in an annular member.

FIG. 25 is cross-section 25-25 shown in FIG. 22 of the particular embodiment of the inventive intraocular implant of generally circular configuration which terminates radially in an annular member.

FIG. 26 is a front perspective view of the particular embodiment of the inventive intraocular implant of generally circular configuration which terminates radially in an annular member having the inner annular surface of the annular member engaged with the haptics of an IOL engaged with the front surface of the intraocular implant.

FIG. 27 is front side view of the particular embodiment of the inventive intraocular implant of generally circular configuration which terminates radially in an annular member having the inner annular surface of the annular member engaged with the haptics of an IOL engaged with the front surface of the intraocular implant.

FIG. 28 is cross-section 28-28 shown in FIG. 27 of the particular embodiment of the inventive intraocular implant of generally circular configuration which terminates radially in an annular member having the inner annular surface of the annular member engaged with the haptics of an IOL engaged with the front surface of the intraocular implant.

FIG. 29 is a back side view of a the particular embodiment of the of the inventive intraocular implant shown in FIGS. 26 through 28 inclusive of patterned surface elements on the back side.

FIG. 30 is an enlarged view of a portion of FIG. 29 showing a particular embodiment of patterned surface elements on the back side of the inventive intraocular implant.

FIG. 31 is a front perspective view of a particular embodiment of the inventive intraocular implant including a flexible membrane joined about the circumference of an optical lens and extending radially outwardly to terminate in an annular member and having a plurality of radial struts extending between the circumference of the optical lens and the inner annular surface of the annular member.

FIG. 32 is a cross-section view 32-32 of the particular embodiment of the inventive intraocular implant shown in FIG. 31.

FIG. 33 is a back perspective view of a particular embodiment of the inventive intraocular implant a flexible membrane joined about the circumference of an optical lens and extending radially outwardly to terminate in an annular member and having an annular channel disposed in the back surface of the intraocular implant.

FIG. 34 is a cross section 34-34 of the particular embodiment of the inventive intraocular implant shown in FIG. 33.

FIG. 35 is a plan view of an embodiment of the inventive intraocular implant having haptics coupled to an optical lens having patterned surface elements disposed on the haptics and about the circumference of the optical lens.

FIG. 36 is a cross-section 34-34 of the embodiment of the inventive intraocular implant shown in FIG. 33.

FIG. 37 is a side view of the embodiment of the inventive intraocular implant shown in FIG. 33.

FIG. 38 is an enlarged view of a circumferential portion of the inventive intraocular implant shown in FIG. 33.

FIG. 43 is an enlarged view of a particular embodiment of a plurality of patterned surface elements in the form of a plurality of raised surface elements on the back surface and a plurality of recessed elements on the front surface which can be coupled to the external surface of embodiments of the inventive intraocular implant.

FIG. 44 is a cross section 44-44 of the plurality of patterned surface elements shown in FIG. 43.

FIG. 45 is an enlarged view of a particular embodiment of a plurality patterned surface elements in the form of a plurality of raised surface elements coupled to the external surface of embodiments of the inventive intraocular implant.

FIG. 46 is a cross section 46-46 of the plurality of patterned surface elements shown in FIG. 45.

FIG. 47 is an enlarged view of a particular embodiment of a plurality of patterned surface elements in the form of a plurality of raised surface elements coupled to the external surface of embodiments of the inventive intraocular implant.

FIG. 48 is a cross section 48-48 of the plurality of patterned surface elements shown in FIG. 47.

FIG. 49 is an enlarged view of a particular embodiment of a plurality of patterned surface elements in the form of a plurality of raised surface elements coupled to the external surface of embodiments of the inventive intraocular implant.

FIG. 50 is a cross section 50-50 of the plurality of patterned surface elements shown in FIG. 49.

FIG. 51 is an enlarged view of a particular embodiment of a plurality of patterned surface elements in the form of a plurality of raised surface elements coupled to the external surface of embodiments of the inventive intraocular implant.

FIG. 52 is a cross section 52-52 of the plurality of patterned surface elements shown in FIG. 51.

Figure 62:
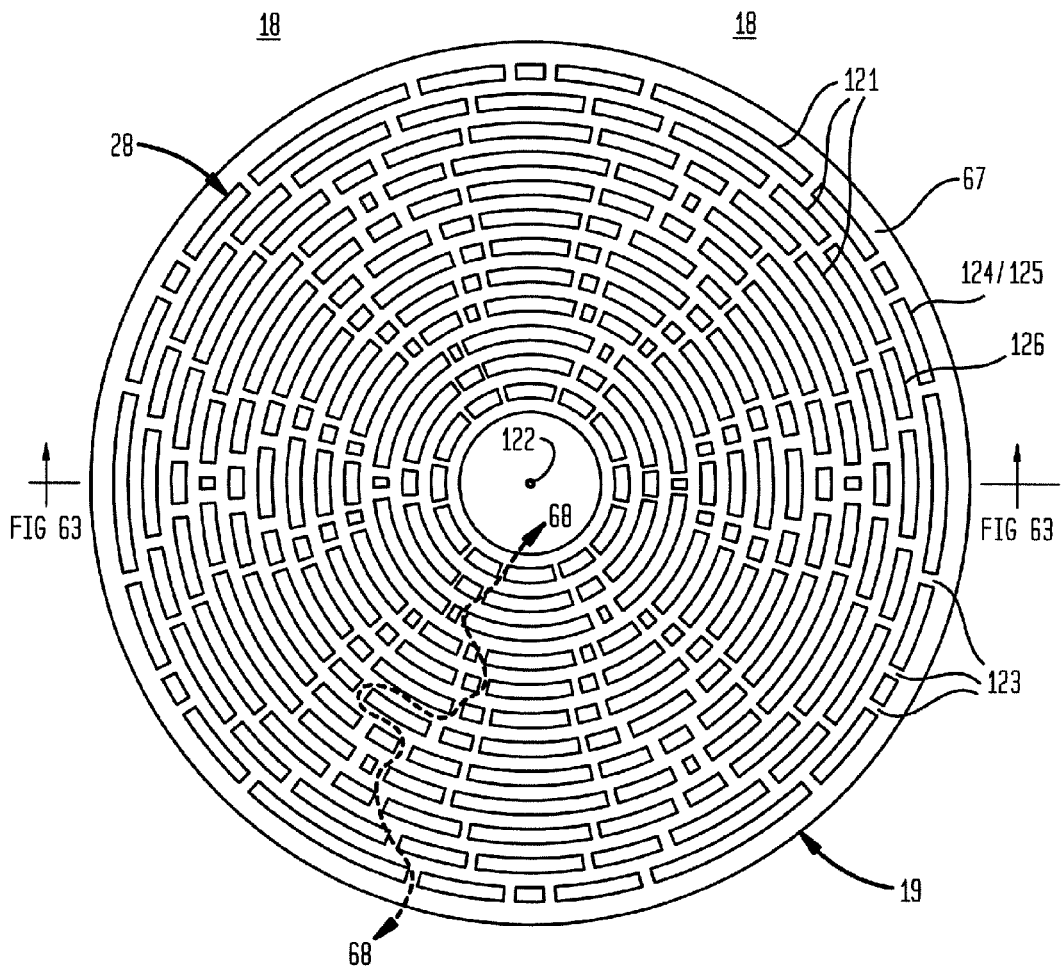

FIG. 62 is an enlarged view of an embodiment of an inventive intraocular implant including a plurality of patterned surface elements in the form of a plurality of raised concentric bands of increasing diameter radially spaced apart about a central point and periodically interrupted circumferentially by a plurality of gaps defining a tortuous pathway on said intraocular implant which traverses the plurality of patterned surface elements.

Figure 63:
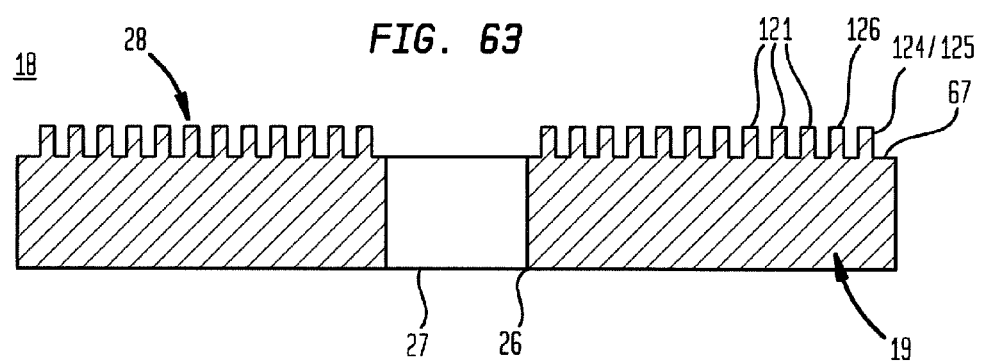

FIG. 63 is a cross-section view 63-63 of the embodiment of the inventive intraocular implant shown in FIG. 62.

Figure 64:
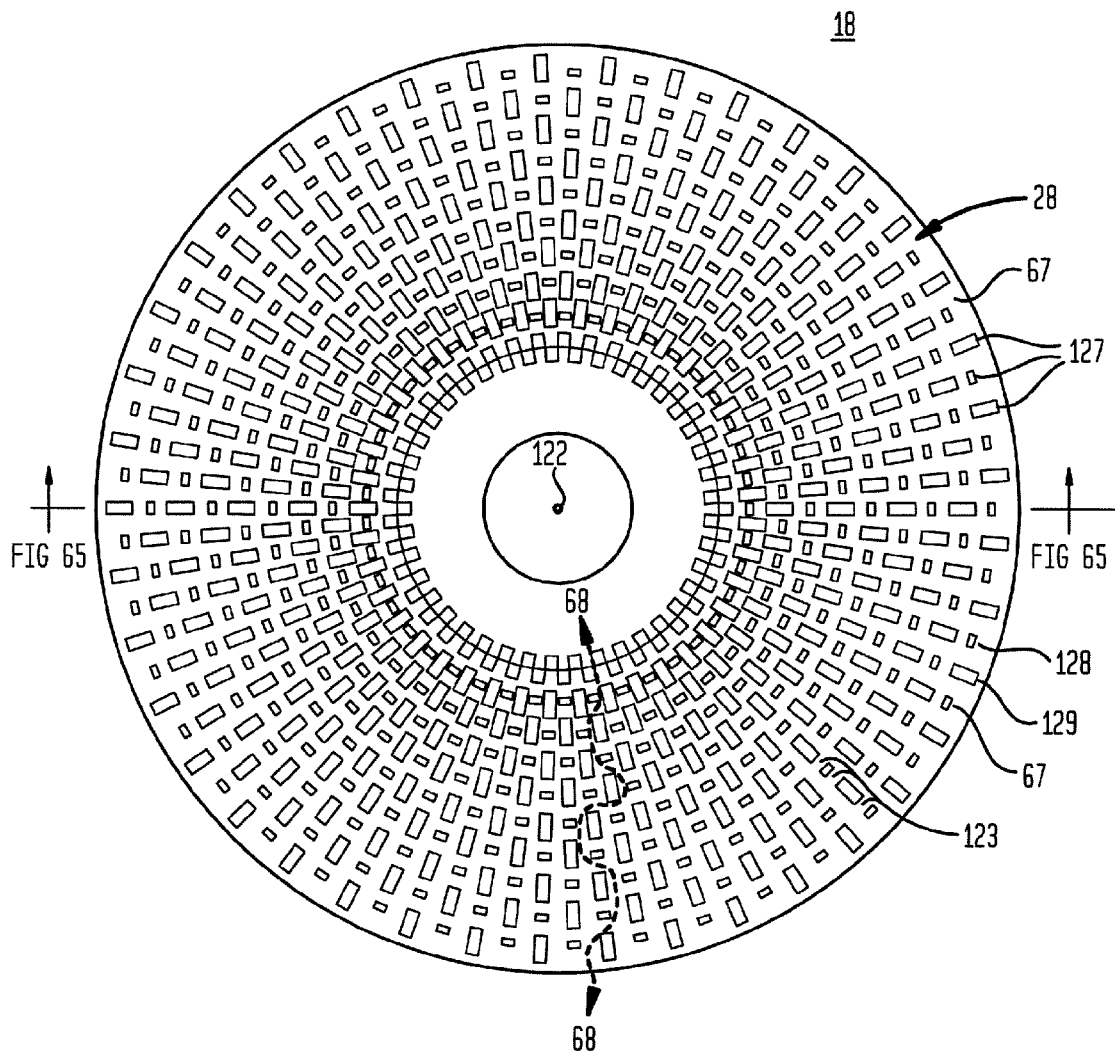

FIG. 64 is an enlarged view of an embodiment of an inventive intraocular implant including a plurality of patterned surface elements in the form of a plurality of raised concentric bands of increasing diameter radially spaced apart about a central point and periodically interrupted circumferentially by a plurality of gaps defining a tortuous pathway on the intraocular implant which traverses the plurality of patterned surface elements which increase in density approaching the central point.

Figure 65:
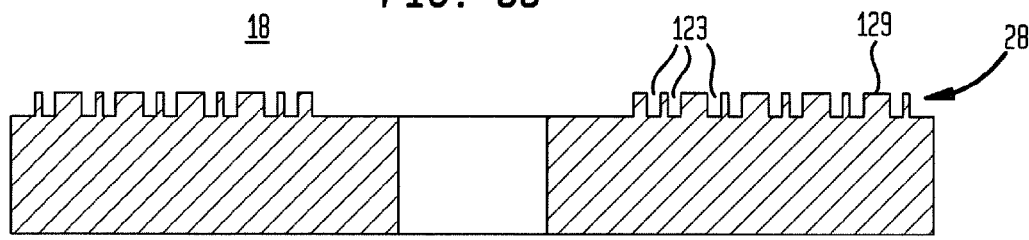

FIG. 65 is a cross-section view 65-65 of the embodiment of the inventive intraocular implant shown in FIG. 64.

FIG. 66 is an enlarged view of an embodiment of an inventive intraocular implant having a plurality of groups of patterned surface elements repeated over the external surface of the intraocular implant with increasing density approaching a central point.

FIG. 67 is a cross-section view 67-67 of the embodiment of the inventive intraocular implant shown in FIG. 66.

Figure 68:
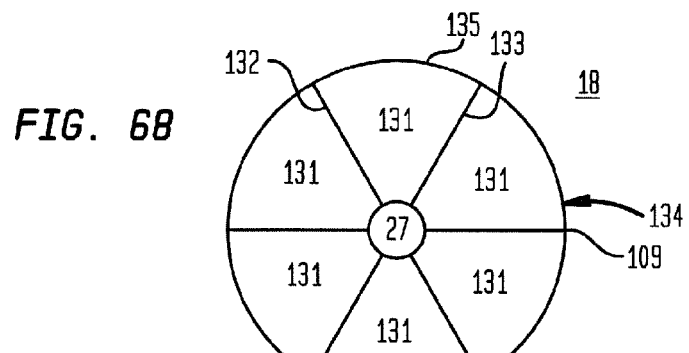

FIG. 68 is an illustration of embodiments of the inventive intraocular implant having a plurality of sectors bound by an interconnected periphery defining a plurality of patterned surface areas each including a plurality of groups of surface elements having a pattern where the pattern in adjacent sections has different angles of rotation with respect to each other.

Figure 69:
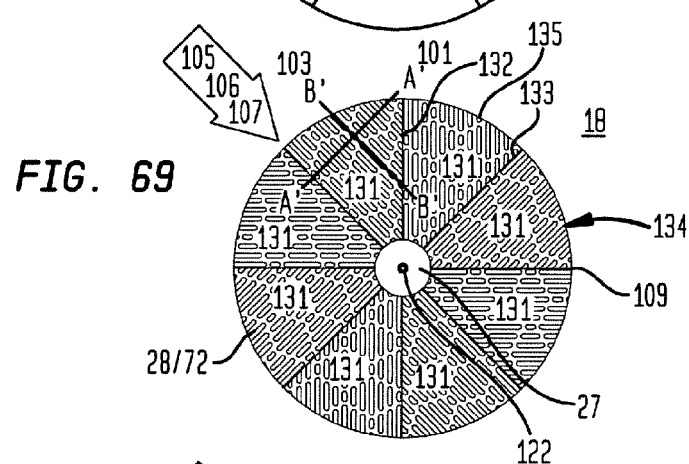

FIG. 69 is an illustration of a particular embodiment of the inventive intraocular implant having a plurality of groups of patterned surface elements having an angle of rotation in each of a plurality of sectors to direct fluid flow radially from a central point.

Figure 70:
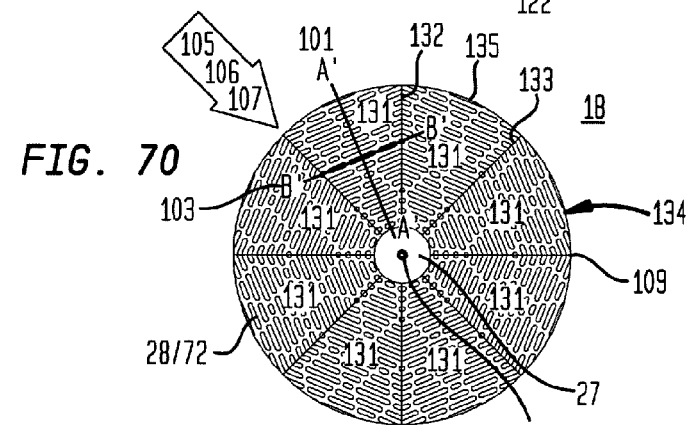

FIG. 70 is an illustration of a particular embodiment of the inventive intraocular implant having a plurality of groups of patterned surface elements having an angle of rotation in each of a plurality of sectors to direct fluid flow circumferentially from a central point.

Figure 71:
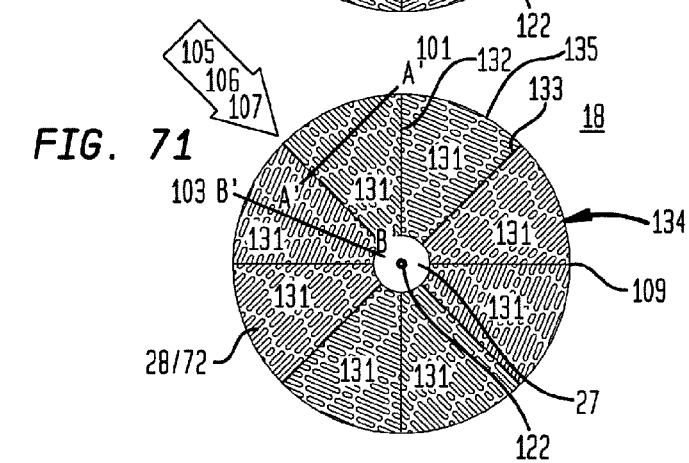

FIG. 71 is an illustration of a particular embodiment of the inventive intraocular implant having a plurality of groups of patterned surface elements having an angle of rotation in each of a plurality of sectors to direct fluid flow in particular sectors radially from a central point and to direct fluid flow in particular sectors circumferentially from a central point.

FIG. 72 shows an embodiment of the intraocular implant held by forceps for implantation into an eye having the natural lens removed.

FIG. 73 is top view of the pseudophakic eye having the natural lens removed allowing an embodiment of the intraocular implant to be positioned on the surface the posterior capsule through an opening made in the anterior capsule.

FIG. 74 is a cross section view of the pseudophakic eye having the natural lens removed allowing an embodiment of the intraocular implant to be positioned on the surface the posterior capsule through an incision made in the anterior capsule.

Figure 75:
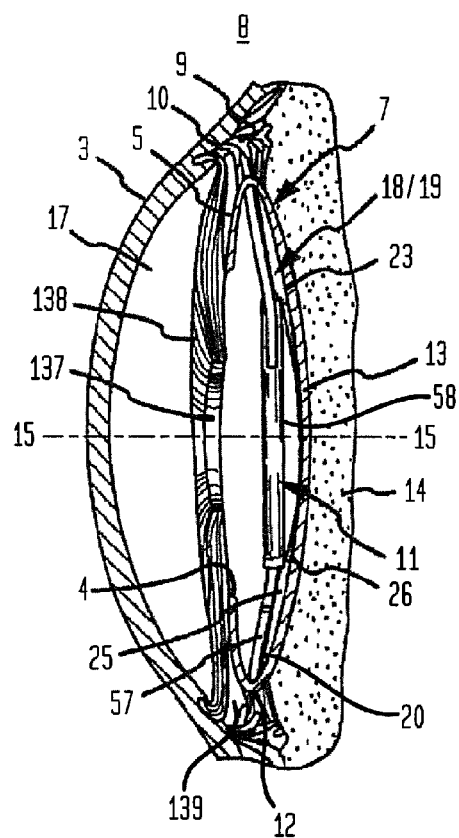

FIG. 75 is a cross section view of the pseudophakic eye having the intraocular implant of FIGS. 5 through 8 positioned between the surface the posterior capsule and the implanted IOL.

Figure 76:
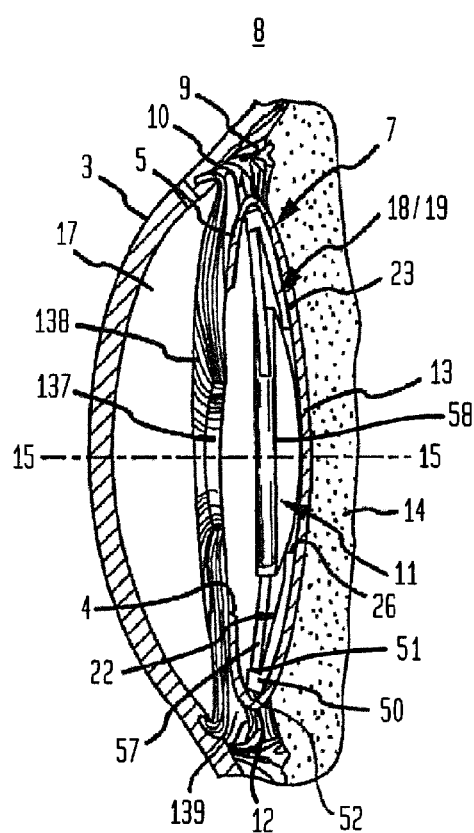

FIG. 76 is a cross section view of the pseudophakic eye having the intraocular implant of FIG. 22 through 25 or FIGS. 26 through 30 positioned between the surface of the posterior capsule and the implanted IOL.

Figure 77:
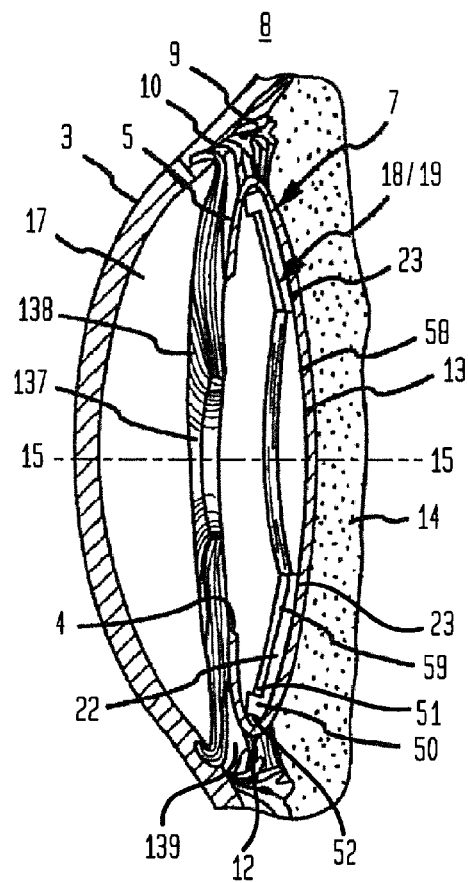

FIG. 77 is a cross section view of the pseudophakic eye having the intraocular implant of FIGS. 31 and 32 or 33 and 34 positioned on the surface of the posterior capsule.

Figure 78:
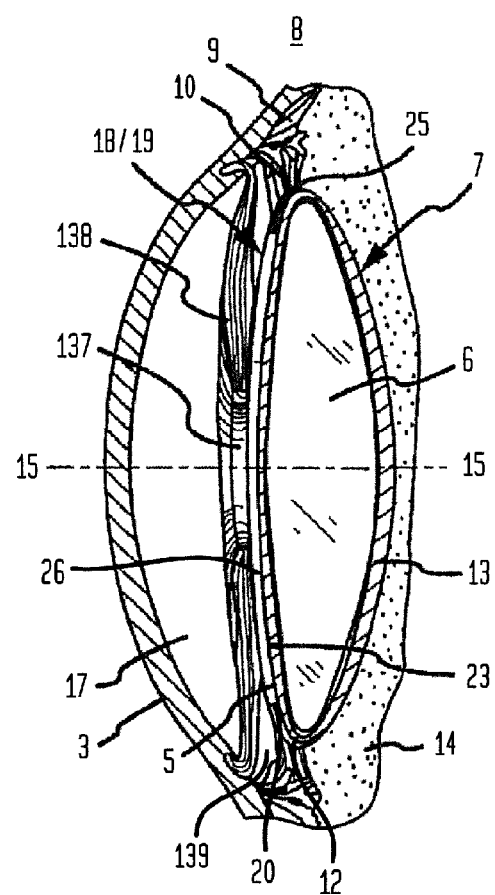

FIG. 78 is a cross section view of the phakic eye having the intraocular implant of FIG. 5 through 8 positioned between the iris and the natural crystalline lens of the eye.

FIG. 79A is a representative image of a cell migration assay showing migration of cells on a smooth surface ("SM") of a flexible membrane as shown in the examples of FIGS. 5 through 8.

Figure 39:
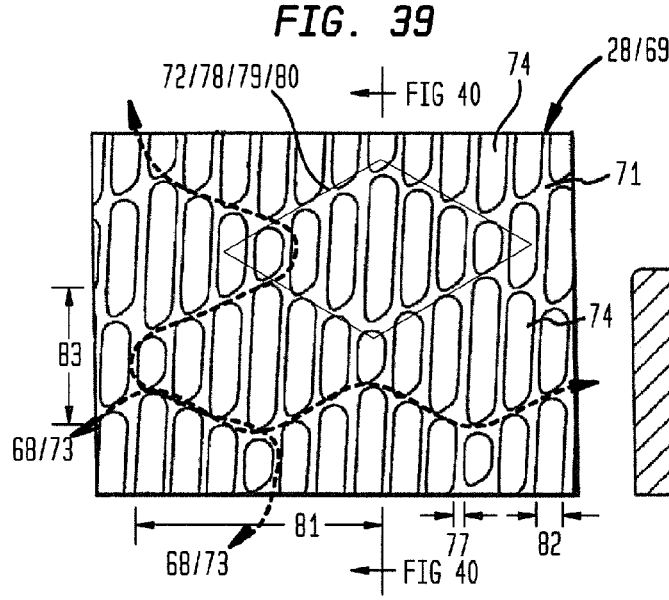
FIG. 39 is an enlarged view of a particular embodiment of a plurality patterned surface elements in the form of a plurality of raised surface elements coupled to the external surface of embodiments of the inventive intraocular implant.

FIG. 79B is a representative image of a cell migration assay showing migration of cells on a flexible membrane having patterned surface elements (+1SK10×5) as shown in the example of FIG. 39.

FIG. 79C is a representative image of a cell migration assay showing migration of cells on a flexible membrane having patterned surface elements (+10SK50×50) as shown in the example of FIG. 39.

FIG. 80 is a bar graph which compares cell migration on a flexible membrane having a smooth surface ("SM") to cell migration on flexible membrane having patterned surface elements ("+1SK10×5") or ("10SK50×50) as shown in the example of FIG. 39.

FIG. 81A is a representative image of scratch wound assay showing migration of cells on a smooth surface ("SM") of a flexible membrane as shown in the examples of FIGS. 5 through 8.

Figure 41:
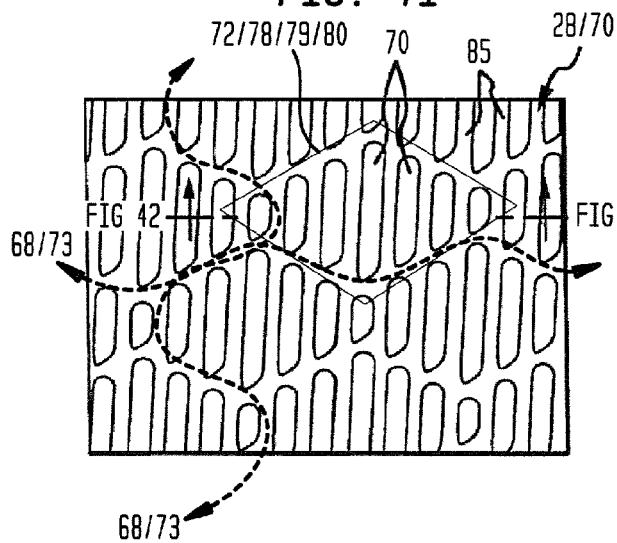
FIG. 41 is an enlarged view of a particular embodiment of a plurality of patterned surface elements in the form of a plurality of recessed elements which can be coupled to the external surface of embodiments of the inventive intraocular implant.
Figure 42:
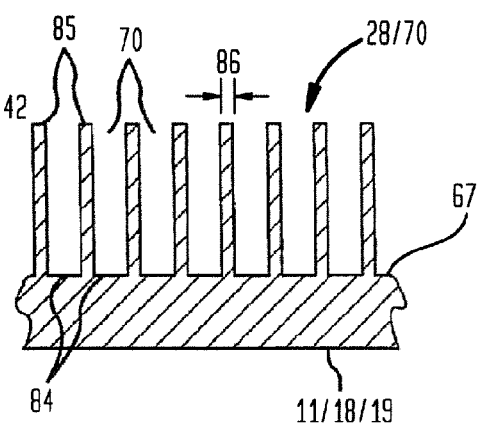
FIG. 42 is a cross section 42-42 of the plurality of patterned surface elements shown in FIG. 41.

FIG. 81B is a representative image of scratch wound assay showing migration of cells on a flexible membrane having patterned surface elements ("−3SK2×2") as shown in the examples of FIGS. 41 and 42.

Figure 40:
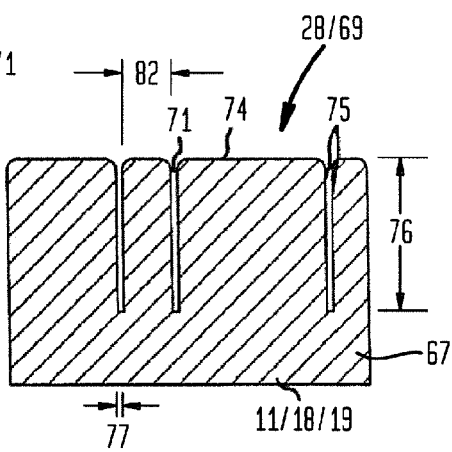
FIG. 40 is a cross section 40-40 of the plurality of patterned surface elements shown in FIG. 39.

FIG. 82C is a representative image of scratch wound assay showing migration of cells on a flexible membrane having patterned surface elements ("+3 SK2×2") as shown in the examples of FIGS. 39 and 40.

FIG. 81D is a representative image of scratch wound assay showing migration of cells on a flexible membrane having patterned surface elements ("+7SK10×5") as shown in the examples of FIGS. 39 and 40.

FIG. 82 is a bar graph which compares cell migration on a flexible membrane having a smooth surface ("SM") to cell migration on flexible membrane having patterned surface elements ("−3SK2×2"), ("+3SK2×2") or ("+7SK10×5") as shown in the examples of FIGS. 39 and 40 or FIGS. 41 and 42.

FIG. 83A is a representative image of a cell migration assay showing migration of LECs between a collagen membrane and an IOL as shown in the illustrative example of FIGS. 3 and 4.

FIG. 83B is a representative image of a cell migration assay showing migration of LECs between a collagen membrane and a smooth backside of the inventive intraocular implant of FIGS. 22 through 25 having an IOL engaged with the front side as illustrated in the example of FIGS. 26 and 27.

FIG. 83C is a representative image of a cell migration assay showing migration of LECs between a collagen membrane and the backside of inventive intraocular implant having patterned surface elements and an IOL engaged with the front side as illustrated in the example of FIGS. 26 through 30.

FIG. 84 is a bar graph comparing each of the IOL, the inventive intraocular implant having a smooth surface, and the inventive intraocular implant having patterned surface elements to normalized area covered by LEC migration.

FIG. 85A is an image of the eye of a rabbit having an IOL inserted in the capsular bag with the eye stained to show migration of LECs.

FIG. 85B is an image of the eye of rabbit having the inventive intraocular implant of FIGS. 23 through 25 with the IOL engaged with the front surface of the intraocular implant inserted in the capsular bag to engage the back surface of the intraocular implant without patterned surface elements with the posterior capsule of the eye with the eye stained to show migration of LECs.

FIG. 85C is an image of the eye of rabbit having the inventive intraocular implant of FIGS. 26 through 30 with the IOL engaged with the front surface of the intraocular implant inserted in the capsular bag to engage the back surface of the intraocular implant having patterned surface elements with the posterior capsule of the eye with the eye stained to show migration of LECs.

FIG. 86 is a bar graph comparing LEC migration of each of the IOL only and the inventive intraocular implant with or without patterned surface elements to a PCO score.

FIG. 87 is a bar graph comparing LEC migration for each of the IOL only and the inventive intraocular implant of FIGS. 26 through 30 with the IOL engaged with the front surface of the intraocular implant inserted in the capsular bag to either engage the back surface of the intraocular implant with patterned surface elements with the posterior capsule of the eye and the annular member engaged to the anterior capsule of the eye ("IOL with annular member up") or engage the back surface of the intraocular implant having patterned surface elements with the anterior capsule of the eye and the annular member engaged to the posterior capsule "IOL with annular member down").

V. DETAILED DESCRIPTION OF THE INVENTION

Generally, an intraocular implant having on the external surface a plurality of pattern surface elements disposed in spaced apart relation defining a tortuous pathway which controls a flow of fluid, a flow of particles suspended in a flow of fluid, or inhibits the growth or migration of cells. In particular, an intraocular implant which implanted between an IOL and the surface of the posterior capsule of the eye inhibits growth or migration of residual lens epithelial cells after cataract surgery by providing structural barriers to reduce PCO of the eye. In particular, an intraocular implant which implanted between an IOL and the surface of the posterior capsule of the eye inhibits migration of residual lens epithelial cells after cataract surgery by providing structural barriers to reduce PCO of the eye.

Definitions

"A" or "an" entity refers to one or more of that entity; for example, "a polymer" refers to one or more of those compositions or at least one composition. As such, the terms "a" or "an", "one or more" and "at least one" can be used interchangeably herein. Furthermore, the language "selected from the group consisting of" refers to one or more of the elements in the list that follows, including combinations of two or more of the elements.

"About" for the purposes of the present invention means that values or ranges of values may be expressed as from "about" one particular value to "about" another particular value. In the context of such a value or range of values "about" means plus or minus 10% of the value or range of values recited or claimed. When such a range of values is expressed, an embodiment includes from about one particular value to about the other particular value. Also, when such a range of values is expressed, another embodiment includes from one particular value to the other particular value and it will be understood that each particular value forms another embodiment.

"Active agent" for the purposes of this invention means any substance used to treat an ocular condition.

"Biocompatible" for the purposes of this invention means the ability of any material to perform the intended function of an embodiment of the invention without eliciting any undesirable local or systemic effects on the recipient and can include non-biodegradable materials such as: polyurethanes, polyisobutylene, polydimethylsiloxane elastomer, ethylene-alpha-olefin copolymers, acrylic polymers and copolymers, vinyl halide polymers and copolymers, polyvinyl esters, polyvinylidene chloride, polyacrylonitrile, polyvinyl ketones, polyvinyl aromatics such as polystyrene, copolymers of vinyl monomers and olefins such as ethylene-methyl methacrylate copolymers, acrylonitrile-styrene copolymers, acrylonitrile butadiene styrene resins, ethylene-vinyl acetate copolymers, polyamides such as Nylon 66 and polycaprolactone, alkyd resins, polycarbonates, polyoxyethylenes, polyimides, polyesters, epoxy resins, rayon-triacetate, cellophane, silicon rubber, silicon hydrogel, or biodegradable materials, as defined herein or combinations thereof.

"Biodegradable" for the purposes of this invention means the ability of any biocompatible material to breakdown within the physiological environment of the eye by one or more physical, chemical, or cellular processes at a rate consistent with providing structural or pharmaceutical barriers (or both) at a therapeutic level controllable by selection of a polymer or mixture of polymers (also referred to as polymeric materials), including, but not limited to: polylactide polymers (PLA), copolymers of lactic and glycolic acids (PLGA), polylactic acid-polyethylene oxide copolymers, poly(ε-caprolactone-co-L-lactic acid (PCL-LA), glycine/PLA copolymers, PLA copolymers involving polyethylene oxides (PEO), acetylated polyvinyl alcohol (PVA)/polycaprolactone copolymers, hydroxybutyrate-hydroxyvalerate copolymers, polyesters such as, but not limited to, aspartic acid and different aliphatic diols, poly (alkylene tartrates) and their copolymers with polyurethanes, polyglutamates with various ester contents and with chemically or enzymatically degradable bonds, other biodegradable nonpeptidic polyamides, amino acid polymers, polyanhydride drug carriers such as, but not limited to, poly(sebacic acid) (PSA), aliphatic-aromatic homopolymers, and poly(anhydride-co-imides), poly(phosphoesters) by matrix or pendant delivery systems, poly(phosphazenes), poly(iminocarbonate), crosslinked poly(ortho ester), hydroxylated polyester-urethanes, or the like. Hydrogels such as methylcellulose which act to release drug through polymer swelling are specifically excluded from the term.

"Intraocular" for the purposes of this invention means inside the eyeball (also referred to as an "eye") and without limitation to the forgoing the anterior chamber, the ciliary sulcus, and posterior capsule of the eye; however, specifically excluding the external surface of the eye or intracorneal or intrasclera regions of the eye.

"Localized Region" for the purposes of this invention means substantially within a localized tissue region of the eye therapeutically affected (whether structurally or pharmaceutically) by implantation of embodiments of an intraocular implant.

"Ocular condition" for the purposes of this invention means a disease, ailment or condition which affects or involves the eye or any one of the parts or regions of the eye, such as PCO. The eye includes the eyeball and the tissues and fluids which constitute the eyeball, the periocular muscles (such as the oblique and rectus muscles) and the portion of the optic nerve which is within or adjacent to the eyeball.

"Posterior ocular condition" for the purposes of this invention means a disease, ailment or condition which affects or involves a posterior ocular region or site such as the choroid or sclera (in a position posterior to a plane through the posterior wall of the lens capsule), vitreous, vitreous chamber, retina, optic nerve (i.e. the optic disc), and blood vessels and nerve which vascularize or innervate a posterior ocular region or site.

"Substantially" for the purposes of this invention means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

"Suitable for implantation" for the purposes of this invention means with regard to embodiments of the intraocular implant dimensions which allow insertion or implantation without causing excessive tissue damage.

"Therapeutic level" for the purposes of this invention means an amount or a concentration of an active agent that has been locally delivered to an ocular region that is appropriate to reduce, inhibit, or prevent a symptom of an ocular condition.

Figure 1:
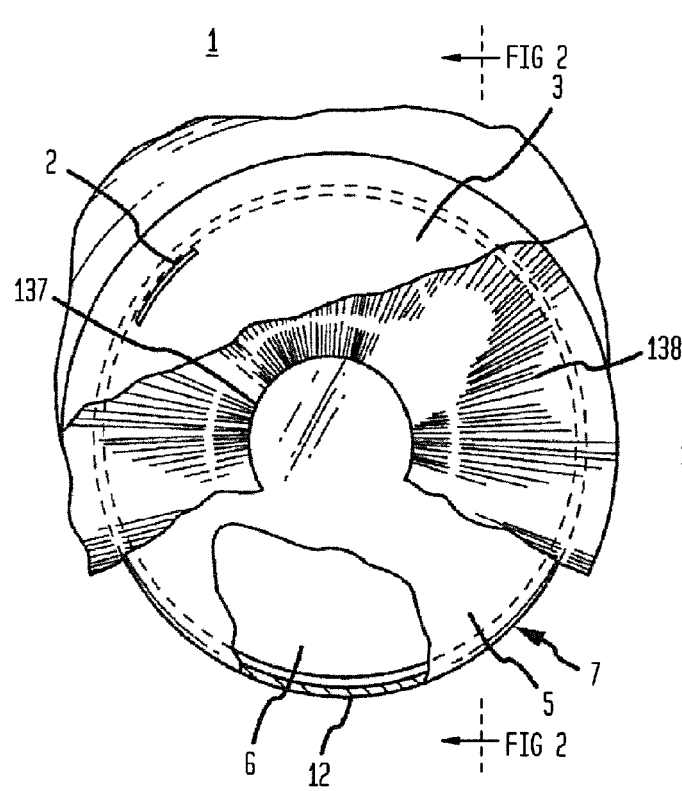
FIG. 1 is a top view of the phakic eye with the natural lens intact.
Figure 2:
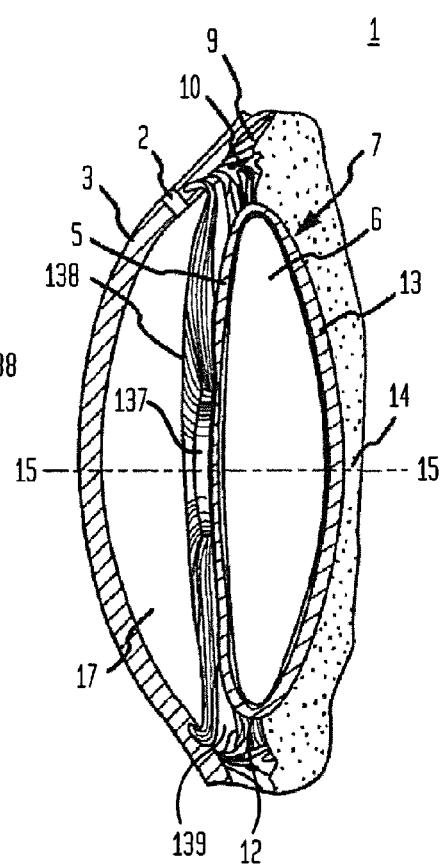
FIG. 2 is a cross section 2-2 of the phakic eye with the natural lens intact.
Figure 5:
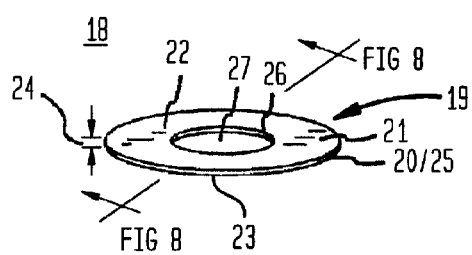
FIG. 5 is a perspective view of a particular embodiment of the inventive intraocular implant of generally circular configuration.
Figure 6:
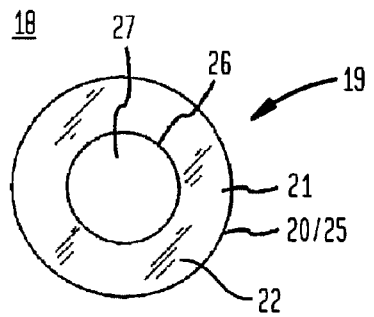
FIG. 6 is a front view of a particular embodiment of the inventive intraocular implant of generally circular configuration.
Figure 7:
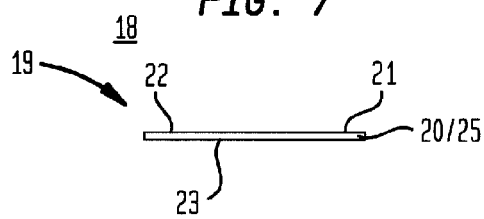
FIG. 7 is a side view of a particular embodiment of the inventive intraocular implant of generally circular configuration which terminates radially in an annular member.
Figure 8:
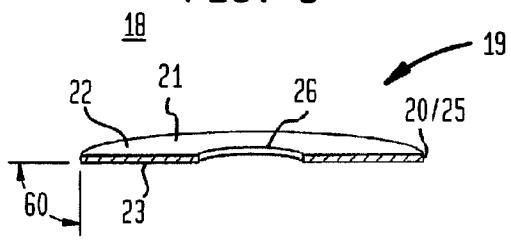
FIG. 8 is a cross-section 8-8 of the particular embodiment of the inventive intraocular implant shown in FIG. 5.

Now generally referring to FIGS. 5-72, particular embodiments of the inventive intraocular implant (18) can provide a biocompatible flexible membrane or a biocompatible biodegradable flexible membrane (also generally referred to as a "flexible membrane" (19)) having an outer boundary (13) configured to allow the intraocular implant (18) to locate in the concavity of the posterior capsule (13) of the pseudophakic eye (4), or other localized region inside the eye (1)(8) such as the ciliary sulcus (139) or anterior chamber (5) depending on the application. As an illustrative example, the intraocular implant (18) can be located in the posterior capsule (13) for the purpose of isolating the surface of the posterior capsule (13) from migration of residual LECs after cataract surgery, or reducing or preventing the migration of residual LECs between the surface of an IOL (11) implanted in the lens capsule (7) and the surface of the posterior capsule (13).

Now referring generally to FIGS. 5 through 34, embodiments of the inventive intraocular implant (18) can provide a flexible membrane (19) having an outer boundary (20) which can define a substantially circular, ovoid, or other outer boundary configuration suitable for implantation into the concavity of the posterior capsule (13) of the pseudophakic eye (8), or other localized region inside the eye (1)(8). As to particular embodiments, the outer boundary (20) of the flexible membrane (19) can define a circular area (21) having a diameter in a range of about 8 millimeters ("mm") to about 15 mm, depending on the recipient and the application. The diameter of the flexible membrane (19) can be selected from the group including or consisting of: about 8.0 mm to about 9.0 mm, about 8.5 mm to about 9.5 mm, about 9.0 mm to about 10.0 mm, about 9.5 mm to about 10.5 mm, about 10.0 mm to about 11.0 mm, about 10.5 mm to about 11.5 mm, about 11.0 mm to about 12.0 mm, about 11.5 mm to about 12.5 mm, about 12.0 mm to about 13.0 mm, about 12.5 mm to about 13.5 mm, about 13.0 mm to about 14.0 mm, about 13.5 mm to about 14.5 mm, about 14 mm to about 15.0 mm. As to particular embodiments, the diameter of the intraocular implant (18) can be pre-selected to allow the outer boundary (20) to engage the outer circumference (12) of the localized region of the eye (1)(8) to fix the position of the intraocular implant (18) in the localized region of the eye (1)(8) excluding any other attachment elements on or in the circular area (21) of the flexible membrane (19) of the intraocular implant (18).

The flexible membrane (19) can, but need not necessarily, be a thin pliable sheet of biocompatible or biodegradable material solid or continuous between a front surface (22) and a back surface (23)(also referred to as "a first side" and "a second side" respectively or "opposed sides"). As to particular embodiments of the intraocular implant (18), the front surface (22) and the back surface (23) can, need not necessarily, be disposed in substantially parallel opposed relation having a thickness (24) therebetween in a range of about 5 microns ("μm") to about 400 μm. As to particular embodiments, the thickness can be selected from the group including or consisting of: about 5 μm to about 100 μm, about 50 μm to about 150 μm, about 100 μm to about 200 μm, about 150 μm to about 250 μm, about 200 μm to about 300 μm, about 250 μm to about 300 μm, about 300 μm to about 400 μm, and about 350 μm to about 400 μm. Depending upon the thickness (24) of the intraocular implant (18), the optical power of the IOL (11) can be adjusted, if necessary.

As to particular embodiments, the flexible membrane (19) can, but need not necessarily, have a uniform thickness (24) disposed between substantially flat or flat front and back surfaces (22)(23)(as shown in the examples of FIGS. 5 through 8). However, embodiments of the intraocular implant (18) can provide a flexible membrane (19) thinner proximate the center and thicker proximate the outer boundary (20) or can provide a flexible membrane (19) thicker proximate the center and thinner proximate the outer boundary (20), depending upon the application. As to other embodiments, the thickness (24) of the flexible membrane (19) can be thinner in the center of the circular area (21) to align with the visual axis (15) of the eye (1)(8) to increase visual acuity or promote directional biodegradation of the intraocular implant (18) from the center toward the outer boundary (20).

As to particular embodiments, the outer boundary (20) of the flexible membrane (19) can have an edge (25) which intersects the front surface (22) or the back surface (23) at substantially a right angle (as shown in the examples of FIGS. 5-9).

Again referring generally to FIGS. 5 through 34, particular embodiments of the inventive intraocular implant (18) can, but need not necessarily, include an aperture element (26) defining a passage opening (27) sufficiently large to align with the visual axis (15) of the eye (1)(8) to provide a line of sight which passes through the intraocular implant (18). Embodiments of the inventive intraocular implant (18) can, but need not necessarily, include an aperture element (26) having a configuration selected from the group including or consisting of: a circle, an oval, a square, a triangle, or other configuration of passage opening (27) alignable with the visual axis (15) and having a passage opening (27) sufficient to provide a line of sight which passes through the intraocular implant (18). As to those embodiments of the intraocular implant (18) utilized in combination with an IOL (11), the passage opening (27) can be dimensioned in relation to the IOL (11) to avoid reduction in the field of vision provided by the IOL (11) or a reduction in clarity of vision within the visual field of the IOL (11). As to those embodiments of the intraocular implant (18) in which the passage opening (27) has insufficient dimension to avoid overlaying all or part of the visual field afforded by the IOL (11), the intraocular implant (18) can be configured to provide sufficient clarity of vision within the visual field afforded by the IOL (11).

As to particular embodiments of the intraocular implant (18) having an aperture element (26) of substantially circular configuration, the aperture element (26) can have a diameter in the range of about 1.5 mm and about 9.0 mm, depending upon the application and the recipient. As to particular embodiments, the aperture element (26) can have diameter selected from the group including or consisting of: about 1.5 mm to about 2.5 mm, about 2.0 mm to about 3.0, about 2.5 mm to about 3.5 mm, about 3.0 mm to about 4.0 mm, about 3.5 mm to about 4.5 mm, about 4.0 mm to about 5.0 mm, about 4.5 mm to about 5.5 mm, about 5.0 mm to about 6.0 mm, about 5.5 mm to about 6.5 mm, about 6.0 mm to about 7.0 mm, about 6.5 mm to about 7.5 mm, about 7.0 mm to about 8.0 mm, about 7.5 mm to about 8.5 mm, and about 8.0 mm to about 9.0 mm.

Figure 9:
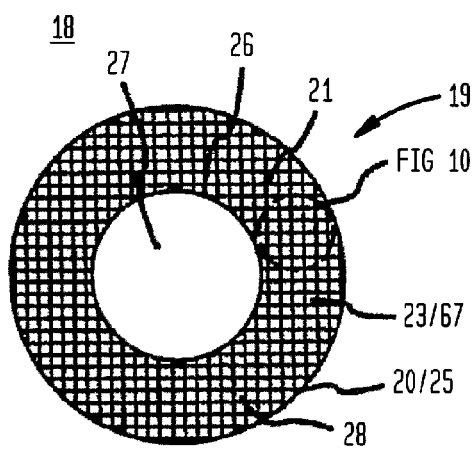
FIG. 9 is a front view or a back view of a particular embodiment of the inventive intraocular implant further providing patterned surface elements.
Figure 10:
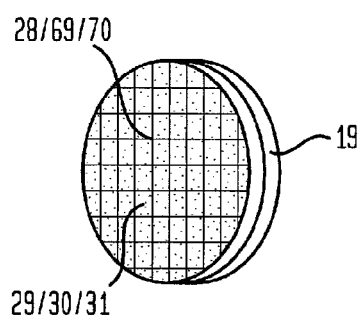
FIG. 10 is enlarged partial back view of the particular embodiment of the inventive intraocular implant shown in FIG. 9 providing patterned surface elements.

Now referring primarily to FIGS. 9 and 10, particular embodiments can, but need not necessarily, have a plurality of patterned surface elements (28) coupled to the external surface (67) of the intraocular implant (18), such as the front surface (22), whether in whole or in part, or the back surface (23) of the intraocular implant (18). As to particular embodiments, the patterned surface elements (28) can be adapted to engage the surface of the posterior capsule (13) to reduce travel of the intraocular implant (18) or maintain the alignment of the center of the intraocular implant (18) with the visual axis (15) of the eye (1)(8). The plurality of patterned surface elements (28) can, but need not necessarily, provide an irregular or uniform pattern, texture, or roughness sufficient to fix or reduce travel of the intraocular implant (18) in the posterior capsule (13). As to certain embodiments of the intraocular implant (18) the plurality of patterned surface elements (28) can, but need not necessarily, provide pockets (29) which function to provide a localized space to deliver or sequester an amount of an active agent (30). The intraocular implant (18) and the plurality of pattern surface elements (28) can be one piece or the plurality of patterned surface elements (28) can be applied to the intraocular implant (18) as a patterned surface element layer (31).

Figure 11:
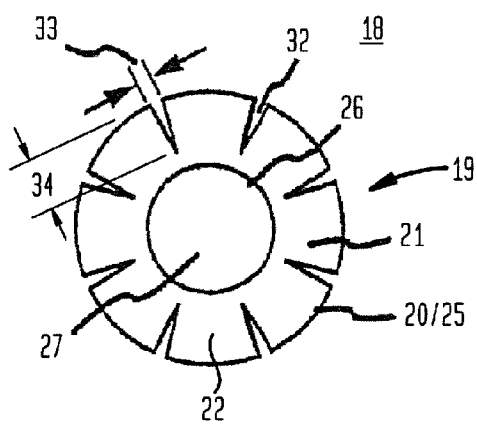
FIG. 11 is a front view of a particular embodiment of the inventive intraocular implant which further provides radial slit elements originating at the outer boundary.

Now referring primarily to FIGS. 11 through 12, and 16 through 18, particular embodiments of the flexible membrane (19) can, but need not necessarily include, one or more radial slit elements (32) cut through the thickness (24) of the flexible membrane (19). As to particular embodiments, the radial slit elements (32) originate at the outer boundary (20) cut a distance radially toward the center of the flexible membrane (19) (as shown in the examples of FIG. 11). The one or more radial slit elements (32) can have sufficient slit length (34) and slit width (33) to allow the flexible membrane (19) to conform to a greater extent with the localize region of the eye or the concavity of the posterior capsule (13) of the eye (1)(8) or other localized region inside the eye (1)(8). The radial slit elements (14) can have a greater slit width (33) at the outer boundary (20) of the flexible membrane (19) than proximate the center of the flexible membrane (19). The flexible membrane (19) when received by the concavity of the posterior capsule (13) can deform to reduce the slit width (33) at the outer boundary (20) of the flexible membrane (19). In addition, the radial slit elements (32) can provide one or more interruptions in the outer boundary (20) which can be of lesser or greater slit width (33) or slit length (34) to control the rate at which the flexible membrane (19) biodegrades within a localized region of the eye (1)(8) such as the posterior capsule (13) of the eye (1)(8).

Now referring specifically to FIGS. 12 and 16 through 18, the aperture element (26) can, but need not necessarily, include one or more radial slit elements (32) each originating at the aperture element (26) and terminating at a distance from the outer boundary (20) of the flexible membrane (19). The one or more radial slit elements (32) can have sufficient slit length (34) and slit width (33) to allow the flexible membrane (19) to conform to a greater extent to the localized region of the eye (1)(8) such as the concavity of the posterior capsule (13) and with respect to embodiments of the intraocular implant (18) which are biodegradable can function to promote directional biodegradation of the intraocular implant (18) proximate the aperture element (26) toward the outer boundary (20). Again, the radial slit elements (32) can provide one or more interruptions in the aperture element (26) which can be of lesser or greater slit width (33) or slit length (34) to control the rate at which the flexible membrane (19) biodegrades within the localized region of the eye (1)(8) such as the posterior capsule (13) of the eye (1)(8).

Figure 12:
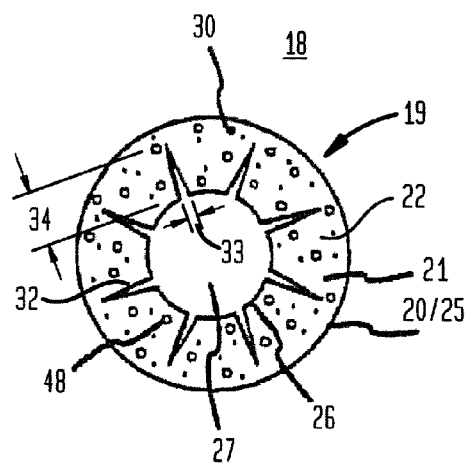
FIG. 12 is a front view of a particular embodiment of the inventive intraocular implant which further provides radial slit elements originating at the aperture element.
Figure 13:
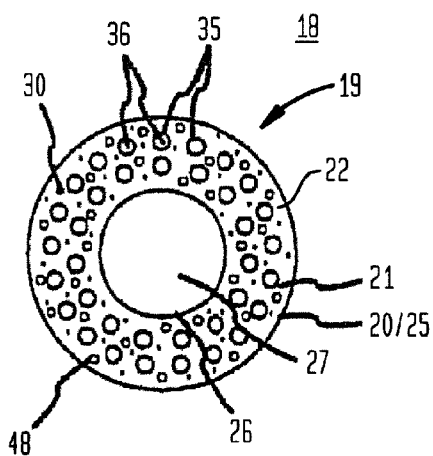
FIG. 13 is a front view of a particular embodiment of the inventive intraocular implant which further provides perforation elements.

Now referring primarily to FIG. 13, embodiments of the flexible membrane (19) can, but need not necessarily, include one or more perforation elements (35) which provide a corresponding one or more perforation openings (36) which communicate between the front surface (22) and the back surface (23) of the flexible membrane (19) for the purpose of increasing rate of biodegradation of the flexible membrane (19) or control release rate of an active agent (30). The active agent (30) shown in the example of FIGS. 12, 13 and 16 as a stipple is not intended to be limited to these particular embodiments of the intraocular implant (18) or limit the active agent (30) to any particular composition, particle size, or amount.

Figure 14:
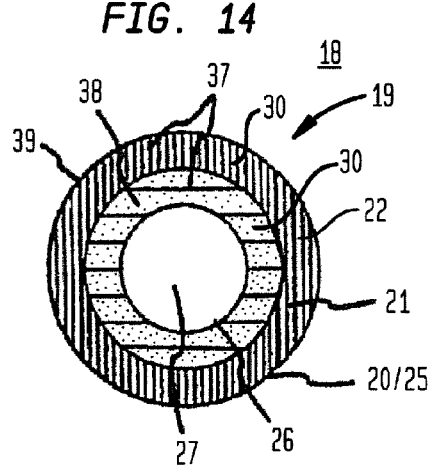
FIG. 14 is a front view of a particular embodiment of the inventive intraocular implant which further provides two more flexible membrane zones.

Now referring primarily to FIG. 14, embodiments, can but need not necessarily, include two or more flexible membrane zones (37). As to certain embodiments, the two or more flexible membrane zones (37) can be established as a first annular zone (38) surrounded by a second annular zone (39). The first annular zone (38) can be of a different biocompatible or biocompatible biodegradable material then the second annular zone (39). For example, the first annular zone (38) can provide a biocompatible biodegradable material selected for a greater rate of biodegradation or release of active agent (30) relative to the second annular zone (39) which can provide a biocompatible biodegradable material selected for a lesser rate of biodegradation or release of active agent (30) release. As to these embodiments, the prominent function of the first annular zone (38) can be to provide a pharmaceutical barrier or treatment of an ocular disorder, while the prominent function of the second annular zone (39) can be to provide a mechanical barrier or treatment of an ocular disorder. In particular embodiments of the inventive intraocular implant (18) for the inhibition of PCO, the first annular zone (38) can be made of the biocompatible biodegradable material poly(lactide-co-glycolide) having an active agent (30), such as an alkylphosphocholine, dispersed substantially uniformly throughout which can provide a pharmaceutical barrier to the proliferation of LECs (16) on the surface of the posterior capsule (13) to inhibit or prevent PCO by release of a therapeutic level of alkylphosphocholine of about 1.0 millimolar ("mM") for a period of about five days. The first annular zone (38) can substantially biodegrade in the entirety in a period of about five days to about ten days. The second annular zone (39) can be made of the same or different biocompatible biodegradable material having the same or a different active agent (30) dispersed substantially uniformly throughout to provide both a mechanical barrier to inhibit migration of LECs (16) toward to the surface of the posterior capsule (13) and can provide a pharmaceutical barrier by release of the same or different active agent (30), such as alkylphosphocholine, at a therapeutic level or provide a localized concentration of about 1.0 mM for a period of at least twenty days to inhibit or prevent PCO.

Now referring primarily to FIGS. 15 through 18, particular embodiments of the flexible membrane (19) can, but need not necessarily, include one or more boundary recess elements (40) located along the outer boundary (20). The outer boundary (20) of the flexible membrane (19) can be interrupted once or periodically to provide one or more boundary recess elements (40) which can be configured, for example, as semicircular extensions (as shown in the example of FIG. 15) or semicircular notches (as shown in the example of FIG. 16), triangular notches, indents, or the like which can function to allow added flexure or to more readily locate the flexible membrane (19) in a localized region of the eye (1)(8) such as the posterior capsule (13) of the eye (1)(8), as above described, or can function to reduce sequestration of fluids within eye (1)(8) or reduce sequestration of peripheral cortical material during the final irrigation and aspiration steps in cataract surgery.

Now referring primarily to FIG. 17, certain embodiments of the flexible membrane (19) can, but need not necessarily, include two or more flexible membrane layers (41). The two or more membrane layers (41) can take the form of a first flexible membrane layer (42) and a second flexible membrane layer (43) or additional flexible membrane layers (44) extruded as a single piece, coupled together as one unit, or stacked front to back (whether single piece, coupled or stacked the term "coupled" may be used to refer to the association of a plurality of flexible membrane layers (41)). Each of the first flexible membrane layer (42) and the second flexible membrane layer (43) or additional flexible layers (44) can be generated from the same or different biocompatible or biocompatible biodegradable materials. As a non-limiting example, in embodiments of the invention for the treatment of PCO, the first flexible membrane layer (42) can be made of a biocompatible or biocompatible biodegradable material which can have the back surface (23) disposed facing the surface of the posterior capsule (13) to provide both a mechanical barrier to the migration of LECs (16) over the surface of the posterior capsule (13) but to further function as a pharmaceutical barrier which inhibits proliferation or kills LECs (16) by the substantially continuous release of an active agent (30), such as alkylphosphocholine, at a rate which provides a therapeutic level of active agent (30), such as a localized concentration of about 1.0 mM for a period of at about five days to inhibit or prevent PCO. The front surface (22) of the first flexible membrane layer (42) can be coupled adjacent the back surface (23) of the second flexible membrane layer (43) (for example by melt co-extrusion) produced from the same or different biocompatible biodegradable material and the front surface (22) of the second flexible membrane layer (43) can be disposed facing an IOL (11) implanted into the lens capsule (7) to provide a mechanical barrier to migration of LECs (16) toward or over the surface of the posterior capsule (13) and can further function as a pharmaceutical barrier which inhibits proliferation or kills LECs (16) by the substantially continuous release of the same active agent (30) (such as an alkylphosphocholine) or a different active agent (30) (such as mitomycin-C) at a therapeutic level, such as a localized concentration of about 0.04 milligrams per milliliter ("mg/mL"), for a period of about five days to inhibit or prevent PCO. Thus, by configuring the layers in different combinations the rate of release of various active agents (30) can be adjusted depending on the application.

Now referring primarily to FIG. 18, particular embodiments of the intraocular implant (18) can, but need not necessarily, include radial capillaries (45) which communicate between the outer boundary (20) and the aperture element (26) of the flexible membrane (19) configured to allow or facilitate circulation of fluid within a localized region of the eye (1)(8), for example, between the flexible membrane (19) and the posterior capsule (13) of the eye (1)(8).

Now referring primarily to FIG. 19, particular embodiments of the intraocular implant (18) can further provide one or more corrugate elements (46) which can, but need not necessarily, be disposed in substantially linear parallel relation to generate undulations in the flexible membrane (19) sufficient when the flexible membrane (19) locates against a surface of a localized region of the eye (1)(8), such as the posterior capsule (13), to provide corrugate channels (47) in which fluids of the eye (1)(8) can circulate.

Again referring in general to FIGS. 5-39, as to those embodiments of the intraocular implant (18) which include an active agent (30), the active agent (30) can, but need not necessarily, be mixed with or dispersed in the biodegradable polymer of the flexible membrane (19). The composition of the biodegradable polymers of the flexible membrane (19) of the intraocular implant (18) can be varied to provide a continuous or substantially continuous release of a therapeutic level of a particular active agent (30) or a particular mixture of active agents (30) effective to treat or alleviate symptoms of an ocular condition. One or more active agents (30) can be selected from the group including or consisting of: ace-inhibitors, endogenous cytokines, agents that influence the basement membrane, agents that influence the growth of endothelial or epithelial cells, adrenergic agonists or blockers, cholinergic agonists or blockers, aldose reductase inhibitors, analgesics, anesthetics, antiallergics, anti-inflammatory agents, antihypertensives, pressors, antibacterials, antivirals, antifungals, antiprotozoals, anti-infectives, antitumor agents, antimetabolites such as daunomycin, anti-angiogenic agents, tyrosine kinase inhibitors, antibiotics such as aminoglycosides such as gentamicin, kanamycin, neomycin, and vancomycin; amphenicols such as chloramphenicol; cephalosporins, such as cefazolin HCl; penicillins such as ampicillin, penicillin, carbenicillin, oxycillin, methicillin; lincosamides such as lincomycin; polypeptide antibiotics such as polymixin and bacitracin; tetracyclines such as tetracycline, minocycline, and doxycycline; quinolones such as ciprofloxacin, moxifloxacin, gatifloxacin, and levofloxacin; sulfonamides such as chloramine T; sulfones such as sulfanilic acid; anti-viral drugs such as acyclovir, gancyclovir, vidarabine, azidothymidine, dideoxyinosine, dideoxycytosine; epinephrine; isoflurphate; adriamycin; bleomycin; mitomycin; ara-C; actinomycin D; scopolamine; and the like, analgesics, such as codeine, morphine, ketorolac, naproxen, an anesthetic, lidocaine; beta.-adrenergic blocker or beta.-adrenergic agonist such as ephedrine, and epinephrine; aldose reductase inhibitor such as epalrestat, ponalrestat, sorbinil, tolrestat; antiallergic such as cromolyn, beclomethasone, dexamethasone, and flunisolide; colchicine, anihelminthic agents such as ivermectin and suramin sodium; antiamebic agents such as chloroquine and chlortetracycline; and antifungal agents such as amphotericin; anti-angiogenesis compounds such as anecortave acetate; retinoids such as Tazarotene, anti-glaucoma agents such as brimonidine (Alphagan and Alphagan P), acetozolamide, bimatoprost (Lumigan), timolol, mebefunolol; memantine; alpha-2 adrenergic receptor agonists; 2-methoxyestradiol; anti-neoplastics such as vinblastine, vincristine, interferons; alpha, beta and gamma., antimetabolites such as folic acid analogs, purine analogs, and pyrimidine analogs; immunosuppressants such as azathyprine, cyclosporine and mizoribine; miotic agents, such as carbachol, mydriatic agents such as atropine, etc., protease inhibitors such as aprotinin, camostat, gabexate, vasodilators such as bradykinin, epidermal growth factor, basic fibroblast growth factor, nerve growth factors, steroidal anti-inflammatory agents such as 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide; vascular endothelial growth factor inhibitors such as bevacizumab, ranibisumab, pegatanib; transforming growth factor inhibitors; fibroblast growth factor inhibitors, and any of their derivatives, or in combinations thereof.

As to particular embodiments of the inventive intraocular implant (18), the active agent (30) can be dispersed throughout the biocompatible biodegradable polymer of the flexible membrane (18) by mixing the active agent (30) into the melted biodegradable polymer and then solidifying the resulting biodegradable polymer by cooling, having the active agent (30) substantially uniformly dispersed throughout. The biodegradable polymer or mixture of biodegradable polymers can be selected to have a melting point that is below the temperature at which the active agent (30) becomes reactive or degrades. Alternatively, the active agent (30) can be dispersed throughout the biodegradable polymer by solvent casting, in which the biodegradable polymer and the active agent (30) are dissolved in a solvent. The solvent can then be evaporated, leaving the active agent (30) in the polymeric matrix of the biodegradable material. Alternatively, the biodegradable intraocular implant (18) can be placed in a solvent having a concentration of the active agent (30) dissolved therein and in which the biodegradable intraocular implant (18) swells. Swelling of the biodegradable intraocular implant (18) draws an amount of the active agent (30) into the biocompatible or biocompatible biodegradable material. The solvent can then be evaporated leaving the active agent (30) within the intraocular implant (18). As to each method of dispersing the active agent (30) throughout the biodegradable polymer of the intraocular implant (18), therapeutic levels of active agent (30) can be achieved in biocompatible biodegradable polymer to treat a particular ocular condition. The biodegradable polymer as a weight percent ("wt. %") of the resulting intraocular implant (18) can be selected from the group including or consisting of: at least about 10 wt. %, about 10 wt. % to about 20 wt. %, about 15 wt. % to about 25 wt. %, about 20 wt. % to about 30 wt. %, about 25 wt. % to about 35 wt. %, about 30 wt. % to about 40 wt. %, about 35 wt. % to about 45 wt. %, about 40 wt. % to about 50 wt. %, about 45 wt. % to about 55 wt. %, about 50 wt. % to about 60 wt. %, about 55 wt. % to about 65 wt. %, about 60 wt. % to about 70 wt. %, about 75 wt. % to about 85 wt. %, about 80 wt. % to about 90 wt. %, or combination thereof, with the balance of the weight being the active agent (30) or other non-active agents (48) dispersed in the biocompatible biodegradable polymer (as shown in the examples of FIGS. 12 and 13).

Other non-active agents (48) can, but need not necessarily, be included in the biocompatible biodegradable polymer formulation for a variety of purposes. For example, as preservative agents, buffering agents, or electrolyte agents. Preservative agents can be selected from the group including or consisting of: sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol and phenylethyl alcohol, or the like, or combinations thereof.

Buffering agents can be selected from the group including or consisting of: sodium carbonate, sodium borate, sodium phosphate, sodium acetate, sodium bicarbonate, or the like, or combination thereof.

Electrolyte agents can be selected from the group including or consisting of: sodium chloride, potassium chloride, or the like, or combinations thereof.

An illustrative example of producing biodegradable embodiments of the inventive intraocular implant (18) for treating or alleviating symptoms of an ocular condition, such as PCO can be made by combining an amount active agent (30) and biodegradable polymer, as above described, to form an active agent polymer material. The active agent polymer material can be extruded or molded to form embodiments of the biocompatible biodegradable intraocular implant (18) having active agent release characteristics at a therapeutic level. As one example, the intraocular implant (18) can substantially continuously release active agent (30) to provide a localized concentration of alkylphosphocholine at therapeutic levels of about 0.5 mM to 1.5 mM for about 5 days or release mitomycin-C to provide a localized concentration of 0.04 mg/mL for a period of about five days to inhibit or prevent PCO.

Embodiments of the flexible membrane (19) can be made by a variety of methods, and while not particularly limited, examples of molding methods which can be used to form a film or sheet includes T-die molding, inflation molding, calendar molding, heat press molding, spin cast molding, injection molding, cast molding, or the like.

Biodegradable embodiments of the flexible membrane (19) can be molded in thinner thickness (24) in order to increase biodegradability, but its thickness (24) can be freely adjusted to satisfy strength, flexibility and release of active agents (30) to achieve therapeutically effective levels of active agent (30) in the localized region of the eye (1)(8) into which the intraocular implant (18) is implanted. Thickness of the flexible membrane (19) as above described can an elastic modulus of about 1,200 MPa or less, more preferably 600 MPa or less. Tensile strength can fall in the range of about 10 megapascal ("MPa") to 100 MPa, more preferably in a range of 15 MPa to 70 MPa, further more preferably in a range of 20 MPa to 50 MPa.

Now referring primarily to FIGS. 20 and 21, embodiments of the intraocular implant (11) may also be removably fixed to the surface of a packaging substrate (49), such as a sterile card, from which it can be lifted as further described below.

Now referring primarily to FIGS. 22 through 34, embodiments of the intraocular implant (18) can, but need not necessarily, further include an annular member (50) having substantially concentric inner and outer annular surfaces (51)(52) joined about or to the front surface (22) of the intraocular implant (18). As to these embodiments, the outer annular surface (52) defines the outer boundary (20) of the intraocular implant (18). Embodiments of the annular member (50), while typically having a substantially circular outer annular surface (52), can have an outer annular surface (52) of elliptical or other form suitable for implantation in a localized region of the eye (1)(8).

Embodiments of the inner and outer annular surfaces (51)(52) can, but need not be, substantially circular with the outer annular surface (52) having an outer annular surface diameter (53) of between about 7 mm and about 15 mm. The outer annular surface diameter (53) can be selected from the group including or consisting of: about 7.0 to about 8.0 mm, about 7.5 mm to about 8.5 mm, about 8.0 mm to about 9.0 mm, about 8.5 mm to about 9.5 mm, about 9.0 mm to about 10.0 mm, about 9.5 mm to about 10.5 mm, about 10.0 mm to about 11.0 mm, about 10.5 mm to about 11.5 mm, about 11.0 mm to about 12.0 mm, about 11.5 mm to about 12.5 mm, about 12.0 mm to about 13.0 mm, about 12.5 mm to about 13.5 mm, about 13.0 mm to about 14.0 mm, about 13.5 mm to about 14.5 mm, about 14 mm to about 15.0 mm.

As to particular embodiments, the outer annular surface diameter (53) of the annular member (50) can be preselected to allow the outer boundary (20) to engage the outer circumference (12) of the localized region of the eye (1)(8) to position of the intraocular implant (18) in the localized region of the eye (1)(8) excluding any other attachment elements on or in the circular area (21) of the flexible membrane (19) of the intraocular implant (18).

The annular member (50) can have an annular member width (54) between the inner and outer annular surfaces (51)(52) of between about 500 μm and about 1500 μm. As an illustrative example, the annular member width (54) of the embodiment shown in FIGS. 22 through 30 can be about 900 µm to about 1100 µm with particular embodiments having a annular member width (54) of about 1000 µm.

Now referring primarily to FIGS. 25, 28, and 34, the outer annular surface height (55) of the outer annular surface (52) can be greater or substantially greater than the thickness (24) of the flexible membrane (19). The outer annular surface height (55) can be between about 10 µm to about 1500 µm, depending upon the application. As an illustrative example, the thickness (24) of the flexible membrane (19) can be between of about 5 µm and about 400 µm while the outer annular surface height (55) can be between about 300 µm to about 1500 µm.

In regard to the particular example shown in FIGS. 26 through 30, the thickness (24) of the flexible membrane (19) can be about 100 µm and the outer annular surface height (55) can be about 1300 µm and the inner annular surface height (56) can be about 1200 µm. The inner annular surface height (56) of the inner annular surface (51) can, but need not necessarily, be sufficiently greater than the thickness (24) of the flexible membrane (19) to provide an inner annular surface (51) having sufficient inner annular surface height (56) to engage the haptics (57) of an IOL (11) overlaying or engaged with the front surface (22) of the flexible membrane (19) to align the optical lens (58) of the IOL (11) with the aperture element (26) of the flexible membrane (19) to provide a line of sight which passes through the aperture opening (27) and the optical lens (58) of the IOL (11).

Now referring primarily to FIGS. 31 and 32, embodiments of the above described intraocular implants (18) can, but need not necessarily, include a plurality of radial struts (59) coupled to the front surface (22) of the flexible membrane (19) between the circumference of the optical lens (58) of the implanted IOL (11), and depending upon the embodiment, the outer boundary (20) of the flexible membrane (10) or the inner annular surface (56) of the annular member (50). The plurality of radial struts (59) can have dimensional relations which maintain the front surface (22) and the back surface (23) of the flexible membrane (19) and the annular member (50) in proper relation to the pseudophakic eye (8) upon implantation as shown in the example of FIGS. 73 through 75.

As to particular embodiments, the outer annular surface (52) can intersect the back surface (23) of the flexible membrane (19) at an angle (60) which upon contact with the surface of the posterior capsule (13) provides a mechanical barrier which impedes migration of LECs (16) toward the center of the intraocular implant (18). While the angle (60) of the intersection of the outer annular surface (52) with the back surface (23) of the flexible membrane (19) can be substantially orthogonal, the angle (60) of intersection can be between about 90 degrees to about 120 degrees. The angle (60) at which the outer annular surface (52) joins the back surface (23) can provide a sharp edge that is not blunt or rounded.

Now referring primarily to FIGS. 33 and 34, embodiments of the intraocular implant (18) can, but need not necessarily, include an annular channel (61) disposed in the back surface (23) of the intraocular implant (18). The annular channel (61) including outer and inner channel walls (62)(63) joined by a channel base (64). The outer and inner channel walls (62)(63) can be disposed in the back surface (23) of the intraocular implant (18) to define an annular channel width (65) of between about 5 µm and about 500 µm. The annular channel depth (66) can be between about 2.5 µm to about 750 µm.

As to particular embodiments, the annular channel (61) can comprise substantially concentric or concentric inner and outer channel walls (62)(63). As to particular embodiments, the annular channel (61) can, but need necessarily, be disposed in the back surface (23) of the intraocular implant (18) between the outer annular surface (52) and the inner annular surface (51) of the annular member (50). As to these particular embodiments the annular channel depth (66) can, but need not necessarily, exceed the thickness of the flexible membrane (19) (as shown in the example of FIG. 34). As to particular embodiments, the annular channel (61) can comprise a plurality of concentric annular channels (61).

FIGS. 5 through 34, provide exemplary embodiments of the inventive intraocular implant (18) which can be used in certain applications without any IOL (11), or as to certain applications in combination with an IOL (11). Now referring in general to FIGS. 5 through 30 and primarily to FIGS. 31 through 34, the intraocular implant (18) can, but need not necessarily, include an optical lens (58) joined to the flexible membrane (19). The optical lens (58) can be aligned with the aperture element (26) of the intraocular implant (18) to provide a line of sight which passes through the optical lens (58). The intraocular implant (18) including the optical lens (58) provides in one piece one or more of the above described features of the intraocular implant (18) along with an optical lens (58) which can obviate the use of a discrete IOL (11) in combination with discrete embodiments of the intraocular implant (18).

The particular embodiment shown in FIGS. 31 through 34, shows the optical lens (58), the flexible membrane (19) and the annular member (50) formed as one piece (any haptics (57) being omitted from the embodiment). The flexible membrane (19) can be joined about the circumference of the optical lens (58). The flexible membrane (19) can extend radially outward to terminate in an outer annular surface (52) of the annular member (50). The dimensional relations of the flexible member (19) and the annular member (50) can be as above-described. A plurality of radial struts (59) can be radially coupled to the front surface (22) of the flexible member (19) between the circumference of the optical lens (58) and the inner annular surface (51) of the annular member (50). The plurality of radial struts (59) having dimensional relations sufficient to maintain the front surface (22) and the back surface (23) of the flexible membrane (19) and the annular member (50) in proper relation to the pseudophakic eye (8) upon implantation as shown in the non-limiting example of FIGS. 73 through 75. Accordingly, the surgical method described below can include the steps of implanting the one piece intraocular implant (18) including the optical lens (58) into the lens capsule (7).

Now referring primarily to FIGS. 39 through 72, embodiments of the intraocular implant (18) in the form of the examples shown in FIGS. 5 through 34, or IOLs (11), can but need not necessarily, include inventive patterned surface elements (28) which provide an irregular or uniform pattern, texture, roughness, or dimensional relations on the external surface (67) of intraocular implants or IOLs (11) which can control the flow of fluids, or the flow of particles or cells suspended in fluids or the adhesion, growth or migration of cells whether driven by cytoplasmic displacement or extension of membrane blebs or by alteration of cytoskeletal structures and adhesions, as in the movement of fibroblasts and epithelial cells with translocation occurring as individual cells or in groups, including chains of cells and sheet-like layers, and particularly the adhesion, growth, and migration of residual LECs (16). The patterned surface elements (28) can be configured to provide a mechanical barrier to the flow of fluids, the flow of suspended cells, or the adhesion, growth or migration of residual LECs (16) to eliminate, substantially eliminate or reduce posterior capsule (13) opacification of the pseudophakic eye (8) after cataract surgery.

Now referring primarily to FIGS. 35 through 38, an IOL (11) can include patterned surface elements (28) coupled to the optical lens (58) or haptics (57) while maintaining a line of sight through the optical lens (58). The patterned surface elements (28) can be adapted to inhibit migration of LECs (16) between the IOL (11) and the surface of the posterior capsule (13) of the eye (8).

Now referring primarily to 39 through 72, patterned surface elements (28) (also referred to as "surface elements") can be coupled to the external surface (67) of the intraocular implant (18) in spaced apart relation defining a tortuous pathway (68) which traverses the plurality surface elements (28). The plurality of surface elements (28) can include a plurality of raised surface elements (69) or a plurality of recessed surface elements (70) which project outwardly or recess inwardly respectively in relation to the external surface (67) of an intraocular implant (18) or IOL (11). The plurality of raised surface elements (69) or recessed elements (70) can be bounded by a corresponding plurality of channels (71) or spacer elements (85) respectively to form a pattern (72) over the entirety or over a portion of the external surface (67) of the intraocular implant (18) or IOL (11). The plurality of raised elements (69) or recessed elements (70) can be disposed in spaced apart relation on the external surface (67) of the intraocular implant (18) or IOL (11) to dispose the plurality of channels (71) in a non-linear or tortuous pathway (68). Referring to FIGS. 39 through 44, as to particular embodiments the plurality of surface elements (28) include a pattern (72) in the form of a sinusoid or a sinusoidal curve (73) and certain patterns (72) of the plurality of surface elements (28) can, but need not necessarily, include a pattern (72) in which the sinusoidal curve (73) has periodicity in mutually perpendicular directions (as shown in the examples of FIGS. 39 through 44).

The plurality of raised or recessed surface elements (69)(70) can be produced from one or more of the biocompatible or biodegradable materials, as above described, which as to certain embodiments can be a material different than used to form the biocompatible or biocompatible biodegradable flexible membrane (19). The top surface (74) of each of the plurality of raised surface elements (69) can be generally flat or planar having a surface area sufficiently small to reduce or prevent adhesion or migration of residual LECs (16) across the plurality of raised surface elements (69) and each of the plurality of channels (71) can be sufficiently small to reduce or prevent migration or adhesion between the plurality of raised surface elements (69).

Embodiments of the top surface (74) of each of the plurality of raised surface elements can have a lesser dimension between two sidewalls (75)(as shown in the example FIG. 40) in the range of about 500 nanometers to about 4 micrometers. Depending upon the application, the lesser dimension can be selected from the group including: about 400 nanometers to about 1 micrometer, about 500 nanometers to about 1.5 micrometers, 1 micrometer to about 2.0 micrometers, 1.5 micrometers to about 2.5 micrometers, 2.0 micrometers to about 3.0 micrometers, 2.5 micrometers to about 3.5 micrometers, 3.0 micrometers to about 4.0 micrometers, and 3.5 micrometers to about 4.0 micrometers, or combinations thereof.

Understandably, the top surface (74) as between two or more of the plurality of raised surface elements (69) can be configured in substantially similar configuration and similar in dimensional relations or as between two or more of the plurality of raised surface elements (69) can be substantially different in configuration or irregular in dimensional relations. The lesser dimension can as to particular embodiments relate to the width of one of the plurality of raised elements (69) and the greater dimension as to particular embodiments can relate to a length of one of the plurality of raised elements (69). However, numerous and varied embodiments can be produced in which the top surface (74) has an irregular surface area, or may be substantially circular or can be a regular polygon, or the like, which do not afford a distinction between width and length. Accordingly, the above dimensions afford guidance sufficient for the person of ordinary skill in the art to provide a plurality of raised surface elements (69) in spaced apart relation having a wide variety of configurations useful in inhibiting adhesion, growth or migration of cells toward the center of the intraocular implant (18) or IOL (11).

The sidewalls (75) of each of the plurality of raised surface elements (69) can be generally vertical to the external surface (67) of the intraocular implant (18) when the flexible membrane (19) is disposed in a generally flat condition. The sidewalls (75) can have a sidewall height (76) in the range of about 400 nanometers to about 6 micrometers. Depending upon the application, the sidewall height (51) can be selected from the group including or consisting of: about 400 nanometers to about 1 micrometer, about 500 nanometers to about 1.5 micrometers, 1 micrometer to about 2.0 micrometers, 1.5 micrometers to about 2.5 micrometers, 2.0 micrometers to about 3.0 micrometers, 2.5 micrometers to about 3.5 micrometers, 3.0 micrometers to about 4.0 micrometers, 3.5 micrometers to about 4.5 micrometers, 4.0 micrometers to about 5.0 micrometers, about 4.5 micrometers to about 5.5 micrometers, and about 5.0 micrometers to about 6.0 micrometers, or combinations thereof.

Each of the plurality of channels (71) defined by opposed sidewalls (75) can have a channel width (77) in the range of about 100 nanometers and about 2.5 micrometers. Depending upon the application, a suitable channel width (77)(as shown in the example FIG. 40) can be selected from the group including: 100 nanometers to about 300 nanometers, about 200 nanometers to about 400 nanometers, about 300 nanometers to about 500 nanometers, about 400 nanometers to about 600 nanometers, about 500 nanometers to about 700 nanometers, about 600 nanometers to about 800 nanometers, about 700 nanometers to about 900 nanometers, about 800 nanometers to about 1 micrometer, about 900 nanometers to about 1.1 micrometer, 1 micrometer to about 1.2 micrometer, 1.1 micrometer to about 1.3 micrometer, 1.2 micrometer to about 1.4 micrometer, 1.3 micrometer to about 1.5 micrometers, 1.4 micrometer to about 1.6 micrometer, 1.5 micrometer to about 1.7 micrometer, 1.6 micrometer to about 1.8 micrometer, 1.7 micrometer to about 1.9 micrometer, and about 1.8 micrometer to about 2 micrometer, or combinations thereof.

Now referring primarily to FIGS. 39 through 54, which provide examples of raised surface elements (69) or recessed surface elements (70) which can be useful in controlling the flow of fluids, the flow of particles suspended in fluids, or inhibiting the adhesion, growth or migration of cells (and particularly LECs (16)) between the back surface (23) of a flexible membrane (19) and the surface of the posterior capsule (13) of the a eye (1)(8) or can be useful in inhibiting the migration of cells between the front surface (22) of the intraocular implant (18) and an engaged IOL (11).

As to the example of FIGS. 39 through 44, the patterned surface elements (28) can have the topography (or reverse topography) of a shark's skin as described in U.S. Pat. No. 7,650,848, hereby incorporated by reference herein to the extent the description does not conflict with the express description of embodiments of the patterned surface elements (28) described herein. The topography of the patterned surface elements (28) can be scaled to inhibit adhesion and migration of residual LECs (16) between the back surface (23) of the intraocular implant (18) and the surface of the posterior capsule (13) of the pseudophakic eye (8). As one illustrative example, the topography of the patterned surface elements (28) can be characterized as a plurality of patterned surface elements (28) organized in a repeating pattern (72) each pattern (72) including a group surface elements (78). Each group of surface elements having seven bar elements (79) in spaced apart parallel relation with the plurality of bars decreasing in length approaching the ends of the pattern (72) to form a diamond pattern (80). The diamond pattern (80) can have an overall diamond length (81) in the range of about 15 micrometers and about 25 micrometers. Each of the seven bar elements (79) can have a bar width (82) in the range of about 1 micrometer and about 2.5 micrometers and a plurality of channels (71) each having channel width (77) of about 400 nanometers and about 2 micrometer. The seven bar elements (79) can have a bar length (83) in the range of about 4 micrometers and about 20 micrometers. The side wall height (76) for each of the seven bar elements (79) can be in the range of about 1 micrometer and about 5 micrometers. The group of surface elements (78) in the diamond pattern (80) can be disposed on the external surface (67) of an intraocular device (18) a shown in the example of FIGS. 39 and 44 to provide, as above described, a tortuous pathway (68) which defines a sinusoidal curve (73) have periodicity in mutually perpendicular directions.

Now referring primarily to FIGS. 41 and 42, particular non-limiting examples of the patterned surface elements (20) can take the form of the topography of a shark's skin as above described; however, the plurality of raised surface elements (69) and plurality of channels (71) can be replaced by a corresponding plurality of recessed surface elements (70) having corresponding plurality of bottom surfaces (84) and a plurality of spacer elements (85) having a corresponding spacer width (86) to form substantially the same diamond pattern (80) having substantially the same dimensional relations as above described. Any of the patterns (72) formed from a plurality of patterned surface elements (28) described herein as a plurality of raised elements (69) and a corresponding plurality of channel elements (71) can take the constructional form of a plurality of recessed surface elements (70) and a plurality of spacer elements (85) having substantially the same or similar pattern or dimensional relations in the ranges above described.

Now referring primarily to FIGS. 43 and 44, particular embodiments of the patterned surface elements (28) can take the form of a plurality of raised surface elements (69) on one side of the flexible membrane (19) and a plurality of recessed elements (70) on the opposed side of the flexible membrane (19). While FIGS. 43 and 44 show a plurality of raised surface elements (69) on the back side (23) of the flexible membrane (19) and a plurality of recessed surface elements (70) on the front side (22) of the flexible membrane (19); it is not intended to preclude other embodiments in which the plurality of recessed surface elements (70) can occur on the back side (23) while the plurality of raised surface elements (69) can occur on the front side (22) of the flexible membrane (19).

Now referring primarily to FIGS. 45 and 46, particular embodiments of the patterned surface elements (28) can take the form of a plurality of raised surface elements (69) each in the form of a cylindrical element (87) in spaced apart relation of columns and rows. Each of the plurality of cylindrical elements (87) having substantially circular top surface (88) having a diameter in the range of about 400 nanometers and about 600 nanometers and side wall height (76) of about 400 nanometers to about 600 nanometers. The plurality of cylindrical elements (87) can be established on centers in the range of about 600 nanometers and about 1 micrometer affording a distance between the sidewalls (77) of between about 200 nanometers and about 400 nanometers.

Now referring primarily to FIGS. 47 and 48, particular embodiments of the plurality of patterned surface elements (28) can take the form of group of surface elements (78) in the form of a repeating bar pattern (89) each characterized by four bar elements (90) of substantially equal length in parallel spaced apart relation having corresponding aligned bar first ends (91) and aligned bar second ends (92) with a cross bar (93) disposed in generally perpendicular relation a distance from the aligned first ends (91) or aligned second ends (92) of the four bar elements (90). Each of the four bar elements (90) can have a bar width (82) in the range of about 2 micrometers and about 5 micrometers and having a corresponding one of a plurality of channels (71) each having channel width (77) of about 400 nanometers and about 1 micrometer. The four bar elements (90) can each have a bar length (83) in the range of about 4 micrometers and about 20 micrometers. The side wall height (76) of each of the four bar elements (90) can be in the range of about 1 micrometer and about 3 micrometers. The cross bar (93) can be disposed a distance from the aligned bar first ends (91) or aligned bar second ends (92) of the four bar elements (90) (or may alternate between the aligned bar first ends (91) and aligned bar second ends (92) as the pattern repeats) in the range of about 400 nanometers and about 1 micrometer. The length of the cross bar (93) can be sufficient to perpendicularly span the distance of the spaced apart relation of the four bar elements (90). The cross bar (93) having dimensional relations otherwise similar to the four bar elements (90).

Now referring primarily to FIGS. 49 and 50, embodiments of the patterned surface elements (28) can take the form of a plurality of raised surface elements (69) each having a hexagonal top surface (94) of generally hexagonal configuration in regular spaced apart tessellation. Each of the hexagonal top surfaces (94) can have a face width (95) in the range of about 400 nanometers and about 600 nanometers and side wall height (76) of about 400 nanometers and about 600 nanometers. The corresponding plurality of channels (71) can have a channel width (77) of about 100 nanometers and about 200 nanometers between each of the plurality of raised elements (69).

Now referring primarily to FIGS. 51 and 52, embodiments of the patterned surface elements (28) can include a plurality of raised elements (69) in the form of a plurality of bar elements (96) in a herringbone pattern (97). Each of the plurality of bar elements (96) can be of substantially equal length in the range of about 4 micrometers and about 20 micrometers and having a bar width (82) in the range of about 2 micrometers and about 5 micrometers. The side wall height (76) of each of the plurality of bar elements (96) can be in the range of about 1 micrometer and about 3 micrometers. The corresponding plurality of channels (71) between the plurality of bar elements (96) can have a channel width (77) of about 400 nanometers and about 1 micrometer.

Figure 53:
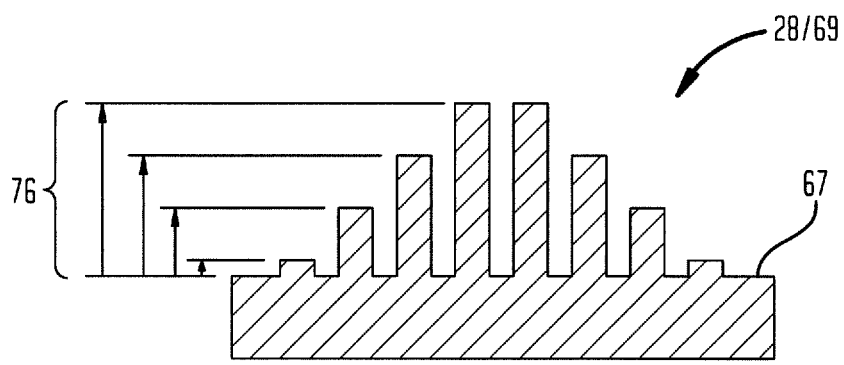
FIG. 53 is a cross section view 53-53 shown in FIG. 39 of a group of surface elements having a pattern in which the height of the plurality of surface elements increases approaching the middle of the pattern.
Figure 54:
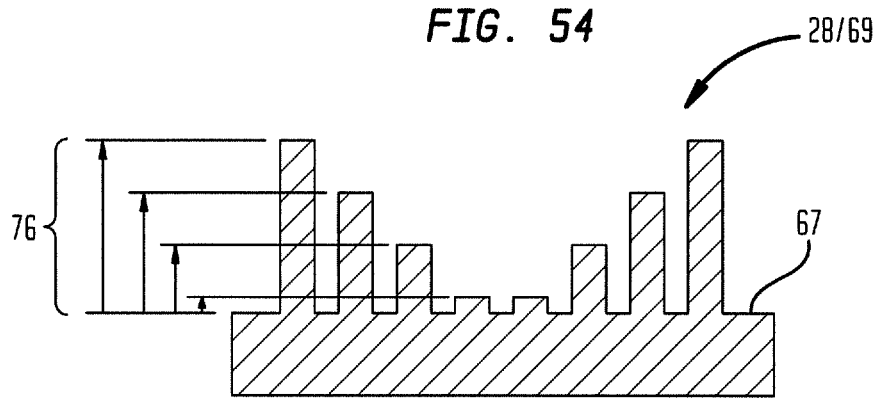
FIG. 54 is a cross section view 54-54 shown in FIG. 39 of a group of surface elements having a pattern in which the height of the plurality of surface elements decreases approaching the ends of the pattern.

Now referring primarily to FIGS. 53 and 54, embodiments of the plurality of surface elements (28) coupled to said external surface (67) of an intraocular implant (18) can, but need not necessarily, vary in side wall height (76) between adjacent surface elements (28). As to particular embodiments in which a plurality of surface elements (28) form a pattern (72) the side wall height (76) can, but need not necessarily, vary within the pattern (72) either increasing in side wall height (76) approaching the center of the pattern (72) (as shown in the example of FIG. 53) or decreasing in sidewall height (76) approaching the middle of the pattern (as shown in the example of FIG. 54).

Figure 55:
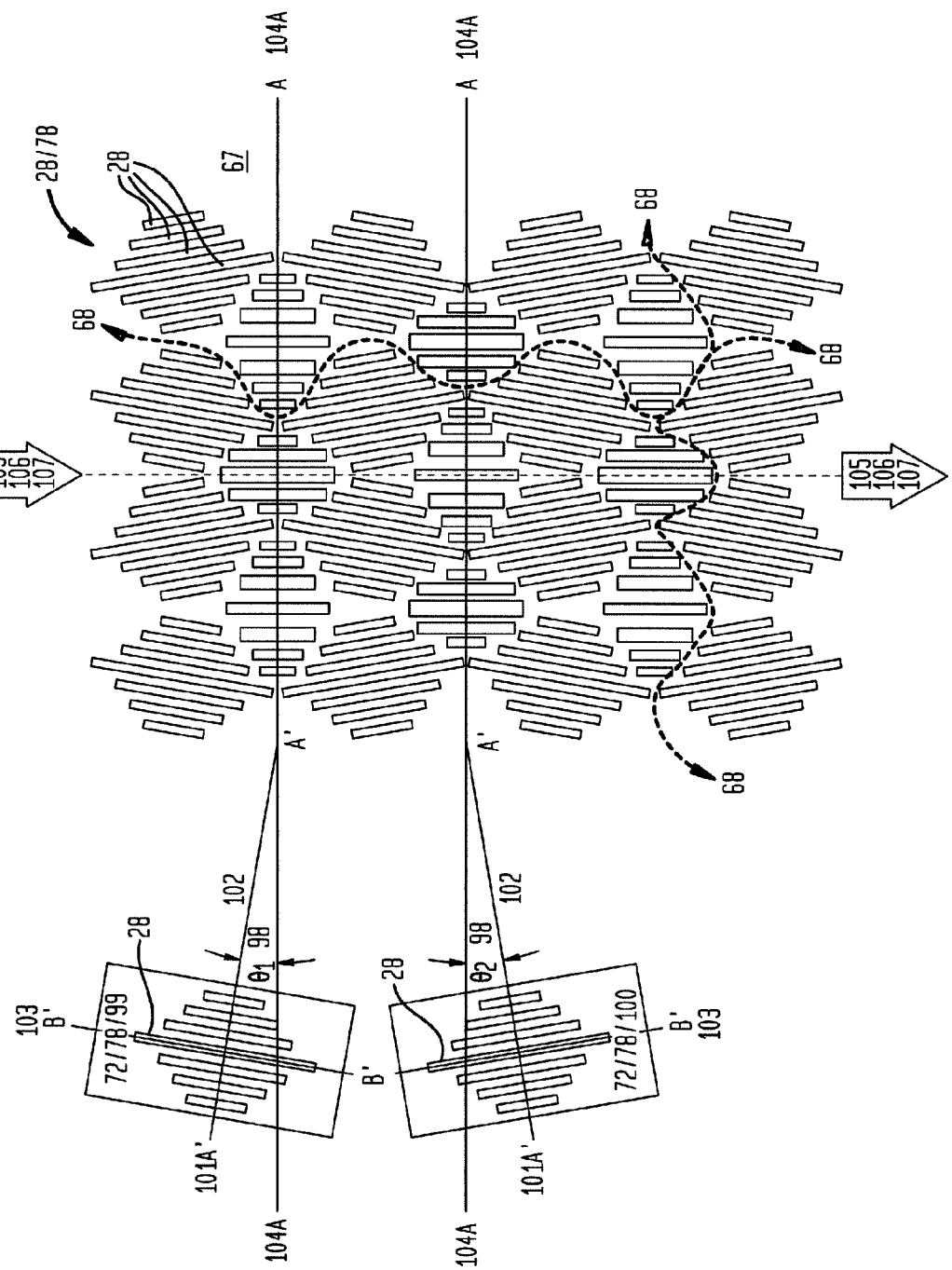
FIG. 55 is an enlarged plan view of a plurality of groups of surface elements with each group of surface elements having a pattern and each group of surface elements having an angle of rotation on the external surface of an intraocular implant different from the angle of rotation of adjacent groups of surface elements on the intraocular implant.

Now referring primarily to FIG. 55, embodiments of the plurality of surface elements (28) on an intraocular implant (18) can, but need not necessarily, include a plurality of groups of surface elements (78). Each of the plurality of groups of surface elements (78) can have a pattern (72) of surface elements (28). The plurality of groups of surface elements (78) can have the same pattern (72) or different patterns (72). The plurality of groups of surface elements (78) can, but need not be, repeated continuously or discontinuously over a part or the entirety of the external surface (67) of the intraocular implant (18) to define a tortuous pathway (68) which traverses the plurality surface elements (28). A first group of surface elements (99) and a second group of surface elements (100) can be disposed at different angles of rotation (98) on the external surface (67) of the intraocular device (18) effective to produce a tortuous pathway (68) between the groups of surface elements (78) as well as between a plurality of surface elements (28) within each one of the groups of surface elements (78).

The example of FIG. 55 illustrates a first group of surface elements (99) and a second group of surface elements (100). In an embodiment, at least one of the first or second group of surface elements (99)(100) can include a pattern (72) characterized by an axis A'-A' (101) passing through a center of mass (102) of the first or second group of surface elements (99)(100) substantially orthogonal to an axis B'-B' (103) of at least one surface element (28) within the pattern (72). In another embodiment, the axis A'-A' (101) passing through the center of mass (102) of the pattern can be substantially orthogonal to the axis B'-B' (103) of at least two surface elements (28) of the pattern (72). In another embodiment, the axis A'-A' (101) passing through the center of mass (102) of the pattern (72) can be substantially orthogonal to the axis B'-B' of at least three surface elements (28) of the pattern (72). In another embodiment, the axis A'-A' (101) passing through the center of mass (102) of the pattern (72) can be substantially orthogonal to the axis B'-B' of at least four of the surface elements (28) of the pattern (72). In yet another embodiment, the axis A'-A' (101) passing through the center of mass (102) of the pattern (72) can be substantially orthogonal to the axis B'-B' of all surface elements (28) of the pattern (72).

The first group of surface elements (99) or the second group of surface elements (100) can have the axis A'-A' (101) disposed at the same or different angles of rotation (98) ($\theta_1$ and $\theta_2$) with respect to an axis A-A (104) disposed orthogonal to a direction of a fluid flow (105), a flow of particles suspended in a fluid flow (106), or an adhesion, a growth or a migration of cells (107) over the external surface (67) of an intraocular implant (18). The angle of rotation (98) ($\theta_1$ and $\theta_2$) of the axis A'-A' of the first or second groups of surface elements (99)(100) from orthogonal or normal to axis A-A (104) can vary from about 0 degrees to about 50 degrees to the axis A-A (104) disposed orthogonal to the direction of fluid flow (105), flow of particles suspended in that fluid flow (106), or the growth or migration of cells (107). The angle of rotation (98) ($\theta_1$ and $\theta_2$) of the first or second group of surface elements (99)(100)(or any of a plurality of groups of surface elements (78)) in relation to the axis A-A (101) can be selected from the group including or consisting of: about 5 degrees, about 5 degrees to about 15 degrees, about 10 degrees to about 20 degrees about 15 degrees to about 25 degrees, about 20 degrees to about 30 degrees, about 25 degrees to about 35 degrees, about 30 degrees to about 40 degrees, about 35 degrees to about 45 degrees, about 40 degrees to about 50 degrees, or combinations thereof.

Now referring primarily to FIGS. 56 through 60, embodiments can, but need not necessarily, include a plurality of sections (108) bounded by an interconnected periphery (109) extending over an entirety or a part of the external surface (67) of an intraocular implant (18) defining a plurality of patterned surface areas (110) each including a plurality of surface elements (28) or a plurality of groups of surface elements (78) defining a tortuous pathway (68). As to particular embodiments, the interconnected periphery (109) can define a plurality of polygons (111) each bounding one of the plurality of patterned surface areas (110). While the examples of FIGS. 56-60, include an interconnected periphery (109) which defines a plurality of polygons (111) in the form of squares or rectangles; this is not intended to preclude an interconnected periphery (109) which defines a plurality of other polygonal forms, such as: triangles, pentagons, hexagons, heptagons, octagons, nonagons, decagons, parallelograms, diamonds, circles, ellipses, ovals, stars, crosses, or the like, or combinations thereof each bounding one of the plurality of patterned surface areas (110).

Figure 56:
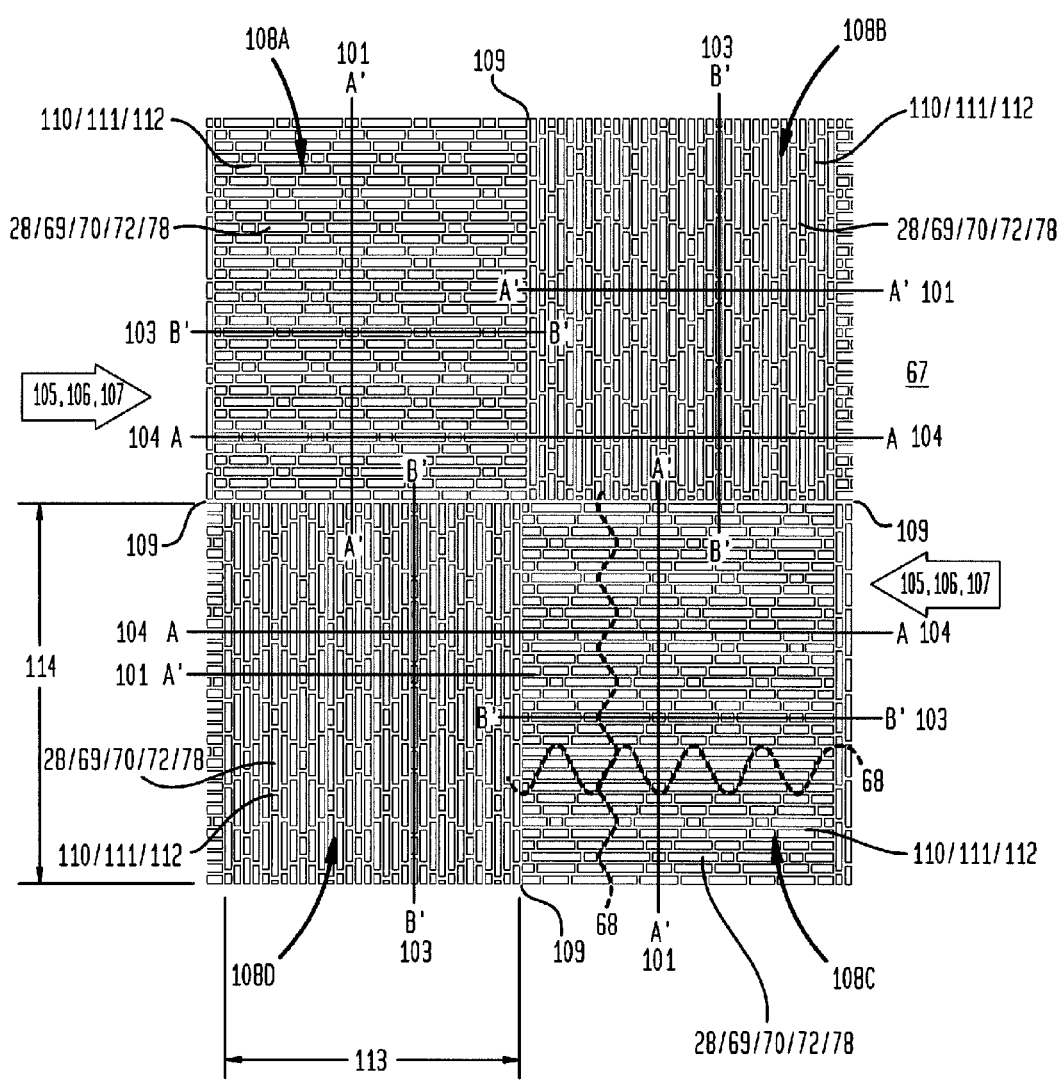
FIG. 56 is an enlarged plan view of a plurality of sections bounded by an interconnected periphery defining a plurality of polygons which bounds a plurality of patterned surface areas each including a plurality of groups of surface elements having a pattern where the patterns in adjacent sections have different angles of rotation with respect to each other.

Now referring primarily to FIG. 56, an embodiment can, but need not necessarily, include a plurality of sections (108)(as an illustrative example 108A, 108B, 108C, 108D) bounded by an interconnected periphery (109) defining a plurality of squares (112) each having a section width (113) and a section length (114) of between about 20 nanometers and about 1000 μm with the section width (113) or the section length (114), with particular embodiments increasing incrementally throughout the range in increments of about 20 nanometers. In the examples of FIGS. 26 through 29, the back surface (23) of the intraocular implant (18) includes a plurality of sections (108) bounded by an interconnected periphery (109) defining a plurality of squares (112) each having a section width (113) and a section length (114) of about 500 μm defining a plurality of patterned surface areas (110) each including a plurality of groups of surface elements (78) in the form shown in the examples of FIGS. 39 and 40.

The plurality of surface elements (28) or the plurality of groups of surface elements (78) within each of the plurality of sections (108) can have an angle of rotation (98), as above described. The angle of rotation (98) of the plurality of groups of surface elements (78) in adjacent sections (108) can be the same or different in relation to the axis A-A (104) disposed orthogonal to the direction fluid flow (105), the flow of particles suspended in the fluid flow (106), or the growth or migration of cells (107) over the external surface (67) of the intraocular implant (18).

As illustrated by the example of FIG. 56, a plurality of groups of surface elements (78) in a section (108) can be parallel to the direction of flow fluid flow (105), the flow of particles suspended in the fluid flow (106), or the growth or migration of cells (107) when the axis A'-A' (101) passing through the center of mass (102) of a pattern (72) being substantially orthogonal to the axis B'-B' (103) of at least one surface elements (28) in the pattern (72) is parallel to the axis A-A (104) as shown in the example of sections (108B and 108D).

A plurality of groups of surface elements (78) in a section (108) can be orthogonal to the direction of flow fluid flow (105), the flow of particles suspended in the fluid flow (106), or the growth or migration of cells (107) when the axis A'-A' (101) passing through the center of mass (102) of a pattern (72) being substantially orthogonal to the axis B'-B' of at least one surface elements (28) in the pattern (72) is orthogonal to the axis A-A (104) as shown in the example of sections (108A and 108C).

Figure 60:
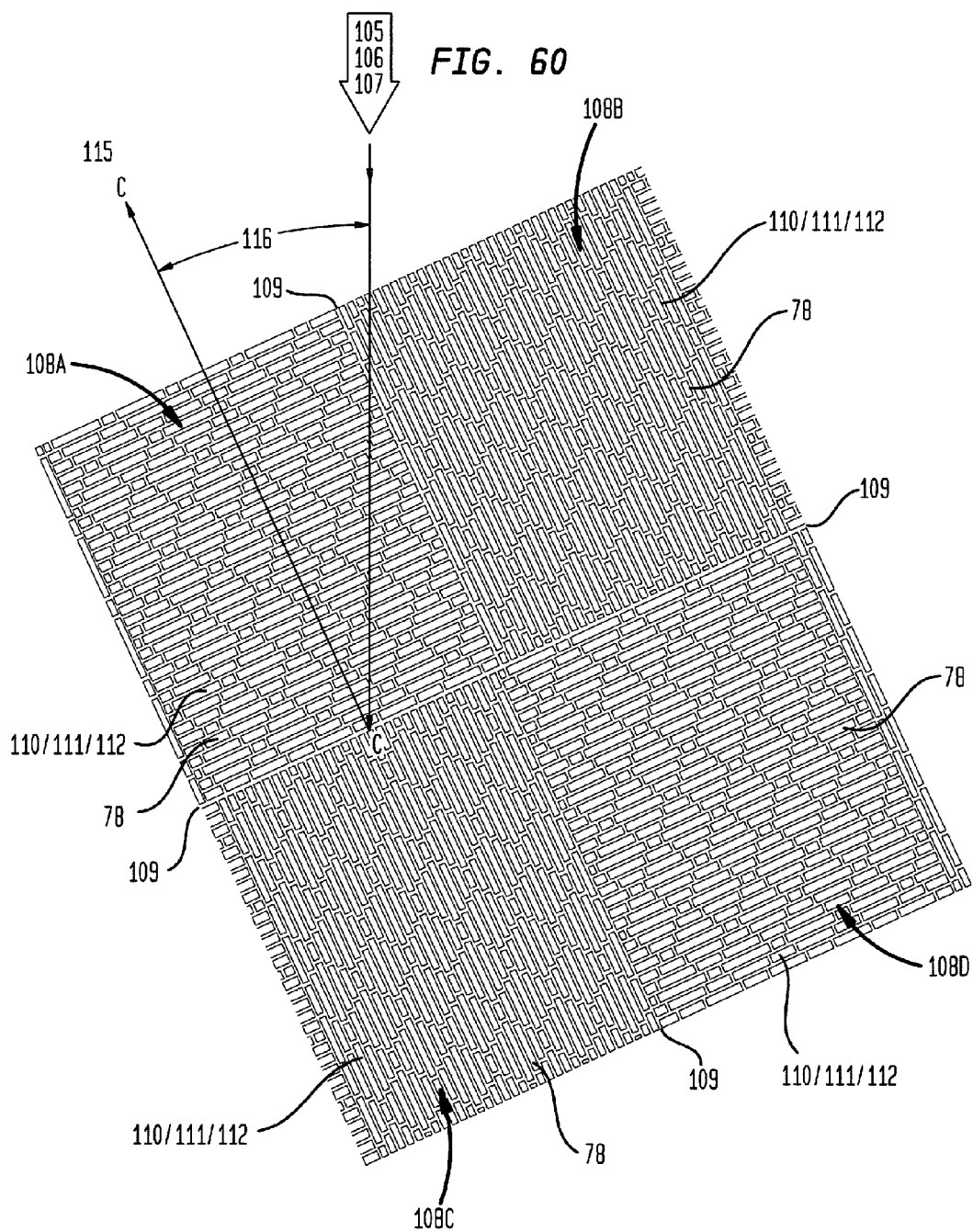
FIG. 60 is an enlarged plan view of a plurality of sections bounded by an interconnected periphery which depicts how the axis of a plurality of sections can be rotated with respect to the fluid flow, the flow of a suspension of particles in a fluid flow, or the adhesion, growth or migration of cells.

The plurality of groups of surface elements (78) in a section (108) can be oblique to the direction of flow fluid flow (105), the flow of particles suspended in the fluid flow (106), or the growth or migration of cells (107) when the axis A'-A' (101) passing through the center of mass (102) of a pattern (72) being substantially orthogonal to the axis B'-B' of at least one surface elements (28) in the pattern (72) is at an angle to the axis A-A (104) as shown in the example FIG. 60.

For the plurality of sections shown in the FIG. 56, the axis A'-A' as to some sections (108B and 108D) can be parallel to the direction of flow fluid flow (105), the flow of particles suspended in the fluid flow (106), or the growth or migration of cells (107) while the axis A'-A' of other sections (108A and 108C) can concurrently be orthogonal to the direction of flow fluid flow (105), the flow of particles suspended in the fluid flow (106), or the growth or migration of cells (107).

Figure 57:
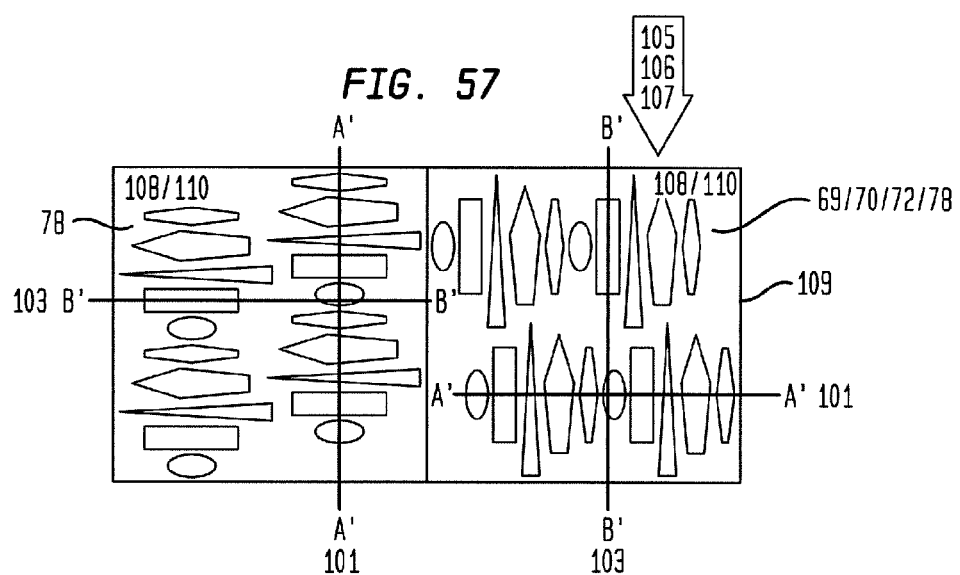
FIG. 57 is an illustration of a plurality of patterned surface elements having regular geometries with adjacent sections of patterned surface elements having different angles of rotation.
Figure 58:
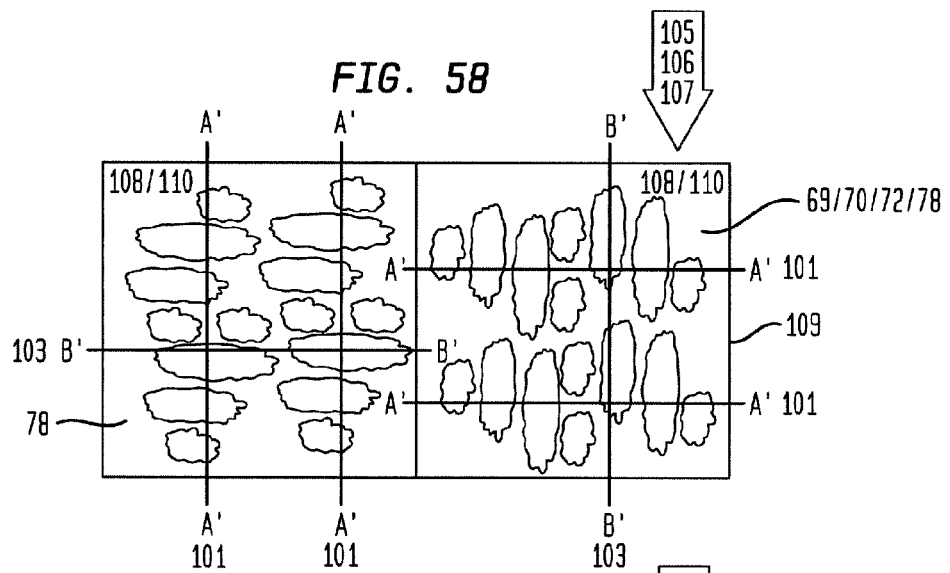
FIG. 58 is an illustration of a plurality of patterned surface elements having irregular geometries with adjacent sections of patterned surface elements having different angles of rotation.
Figure 59:
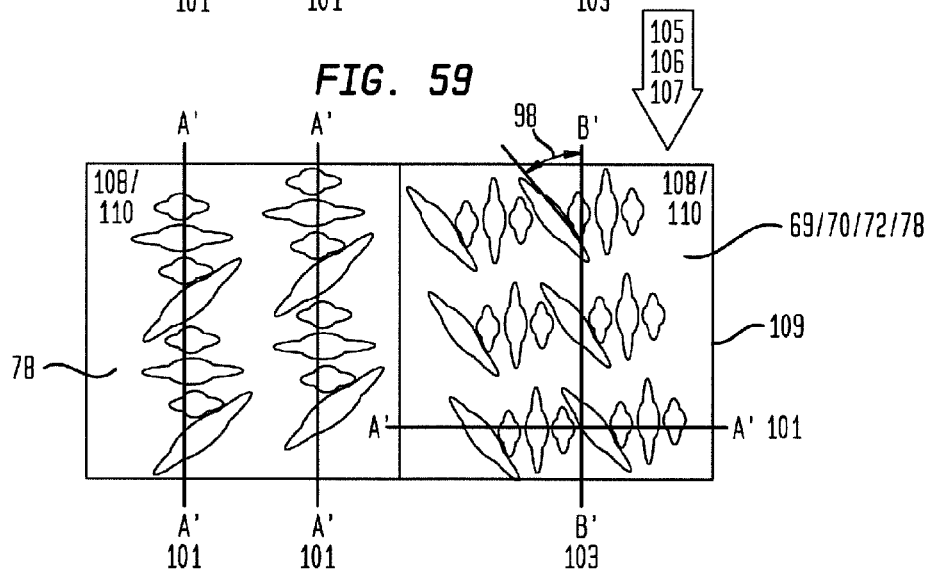
FIG. 59 is an illustration of a plurality of patterned surface elements having a combination of regular and irregular geometries with adjacent sections of patterned surface elements having different angles of rotation.

Now referring primarily to FIGS. 57 through 59, embodiments can include a plurality of sections (108) in which the plurality of groups of surface element (78) are repeated over a pattern surface area (110) to control fluid flow (105), a flow of particles suspended in the fluid flow (106), or growth or migration of cells (107). FIG. 57 illustrates that a plurality of groups of surface elements (78) can include a plurality of surface elements (28) of regular geometries with adjacent sections (108) having the plurality groups of surface elements (78) disposed a different angles of rotation (98). FIG. 58 illustrates that a plurality of groups of surface elements (8) can include a plurality surface elements (28) of irregular geometries with adjacent sections (108) having the plurality groups of surface elements (78) disposed a different angles of rotation (98). FIG. 59 illustrates that a plurality of groups of surface elements (78) can include a plurality of surface elements (78) of both regular and irregular geometries with adjacent sections (108) having the plurality of groups of surface elements (78) disposed a different angles of rotation (98). Embodiments can, but need not necessarily, include at least some of the plurality of surface elements (28) of a pattern (72) having aspect ratios greater than 1.

Now referring primarily to FIG. 60, the axis C-C (115) of a plurality of sections (108) can, but need not necessarily, be rotated with respect to the direction of fluid flow (105), a flow of particles suspended in the fluid flow (106), or growth or migration of cells (107). As to particular embodiments, rotation of a plurality of sections (108) can dispose the axis A'-A' (101) of a plurality of groups of surface elements (78) within one or more of the plurality of patterned surface areas (110) at a section angle (116) to the direction of fluid flow (105), a flow of particles suspended in the fluid flow (106), or growth or migration of cells (107) of between about 5 degrees and about 175 degrees, preferably about 15 degrees to 150 degrees, more preferably about 50 degrees to about 135 degrees and more preferably about 75 degrees to about 125 degrees to the flow direction.

Figure 61:
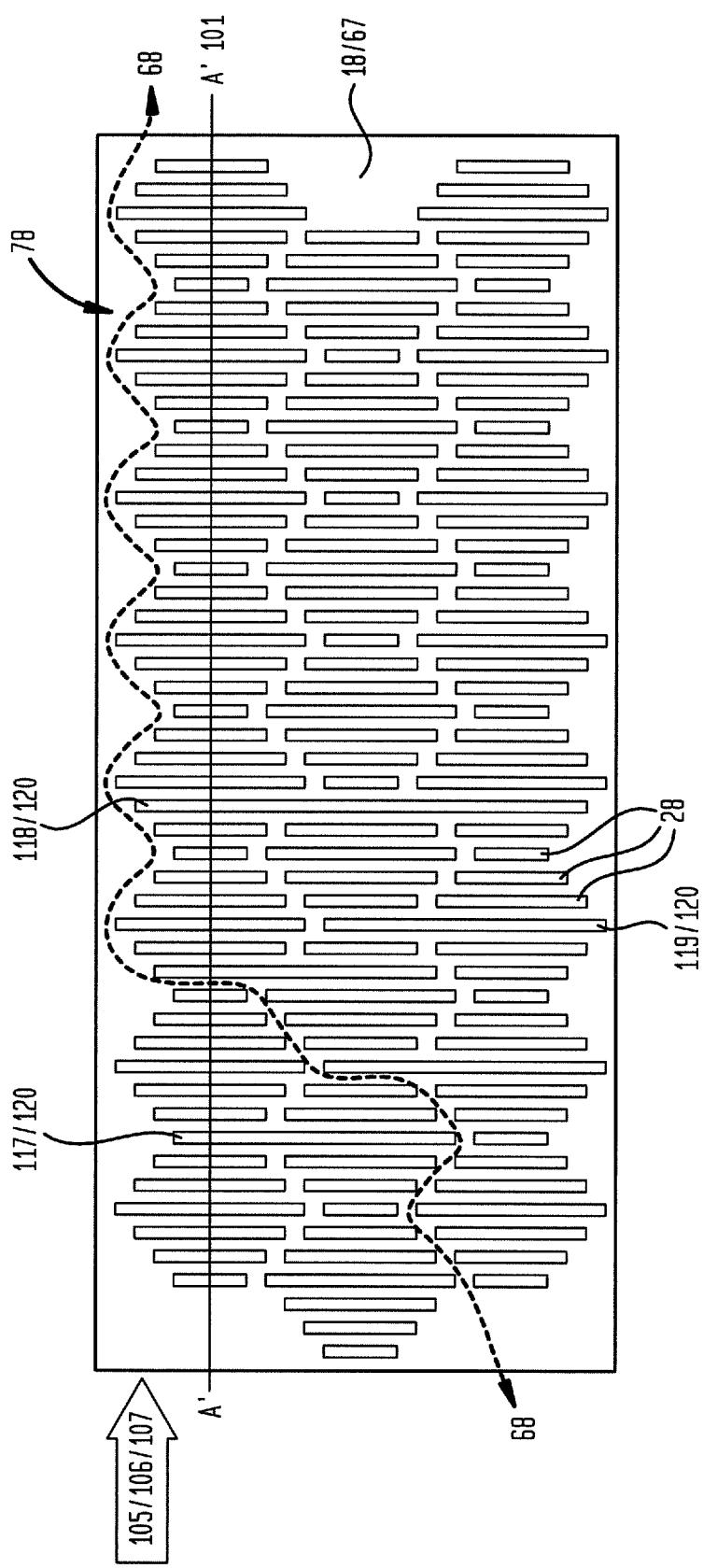
FIG. 61 is an enlarged plan view of a plurality of patterned surface elements having adjacent patterned surface elements conjoined.

Now referring primarily to FIG. 61, as to particular embodiments, one or more of a plurality of surface elements (28) included in adjacent groups of surface elements (78) can, but need not necessarily, be conjoined to increase the length of the tortuous pathway (68) traversing the plurality of surface elements (28). As illustrated in the example of FIG. 61 patterned surface elements (117, 118 and 119) are joined with a one or more patterned surface element (28) included in adjacent groups of surface elements (78) to produce one or more an elongated surface elements (120).

Now referring primarily to FIGS. 62 and 63, a plurality of surface elements (28) can, but need not necessarily, be coupled to the external surface (67) of an intraocular implant (18) in the form of a plurality of concentric bands (121) (whether raised or recessed (69)(70)) of increasing diameter disposed about a central point (122). The plurality of concentric bands (121) can be radially spaced apart and periodically interrupted circumferentially by a plurality of gaps (123) to define a tortuous pathway (68) between an outer diameter (124) of the plurality of concentric bands (121) and the central point (122). The plurality of gaps (123) in a first concentric band (125) can each be aligned with a patterned surface element (28) in an adjacent second concentric band (126) to radially extend the length of the tortuous path (68).

Now referring primarily to FIGS. 64 and 65, the plurality of surface elements (28) can, but need not necessarily, be coupled to the external surface (67) of an intraocular implant (18) in the form of a plurality of radial bands (127) extending from a central point (122). The plurality of radial bands (127) can be circumferentially spaced apart and a periodically interrupted radially by a plurality of gaps (123) to define the tortuous pathway (68) between an outer diameter (124) defined by the plurality of radial bands (127) and the central point (122). The plurality of gaps (123) in a first radial band (128) can each be aligned with a patterned surface element (28) of an adjacent second radial band (129) into circumferentially extend the length of the tortuous path (68).

Now referring primarily to FIGS. 66 and 67, the plurality of surface elements (28) can, but need not necessarily, have a surface element density (130) which varies over the external surface (67) of an intraocular implant (18). With respect to a plurality of surface elements (28) as shown in the examples of FIG. 62 or 64, the surface element density (130) can increase or decrease approaching the central point (122).

Now referring primarily to FIG. 68, the interconnected periphery (109) can, but need not necessarily, define a plurality of sectors (131) each defined by two radii (132) (133) of a circle or ellipse (134) connected by an arc (135). Each sector (131) defines a patterned surface area (110). A plurality of groups of surface elements (78) in each of the plurality of sectors (131) can have an angle of rotation (98), as above described for a plurality of sections (108), which is the same or different in relation to adjacent sectors (131) or in relation to flow of fluid (105), the flow of particles suspended in a fluid flow (106), or the growth or migration of cells (107) over the external surface (67) of an intraocular implant (18).

Now referring primarily to FIG. 69, as to particular embodiments, the plurality of channels (71) between patterned surface elements (28) of a pattern (72) within each sector (131) can be aligned to direct a fluid flow (105), a suspension of particles within a fluid flow (106) or the adhesion, growth or migration of cells (107) radially in relation to central point (122). As to particular embodiments the axis A'-A' (101) of a pattern (72) can be disposed substantially orthogonally to one radii (132)(133) of the circle or ellipse (134).

Now referring primarily to FIG. 70, as to particular embodiments, the plurality of channels (71) between patterned surface elements (28) of a pattern (72) within each sector (131) can be aligned to direct a fluid flow (105), a suspension of particles within a fluid flow (106) or the adhesion, growth or migration of cells (107) circumferentially in relation to central point (122). As to particular embodiments, the axis A'-A' (101) of a pattern (72) can be disposed substantially parallel to one radii (132)(133) of the circle or ellipse (1340.

Now referring primarily to FIG. 71, as to particular embodiments, the plurality of channels (71) between patterned surface elements (28) of a pattern (72) within some sectors (131) can be or aligned to direct a fluid flow (105), a suspension of particles within a fluid flow (106) or the adhesion, growth or migration of cells (107) circumferentially in relation to central point (122) and the plurality of channels (71) between patterned surface elements (28) of a pattern (72) within other sectors (131) can be or aligned to direct a fluid flow (105), a suspension of particles within a fluid flow (106) or the adhesion, growth or migration of cells (107) radially in relation to central point (122). As to particular embodiments, the axis A'-A' (101) of a pattern (72) in some sectors (131) can be disposed substantially parallel to one radii (132)(133) of the circle or ellipse (134) and the axis A'-A' (101) of a pattern (72) in other sectors (131) can be disposed substantially orthogonal to one radii (132)(133) of the circle or ellipse (134).

Again referring primarily to FIGS. 1-4, as above described the most common surgical technique of cataract surgery may be ECCE (although use of embodiments of the inventive intraocular implant (18) is not limited to cataract surgery or to any particular technique of cataract surgery) which involves the creation of a circular opening (4) in the anterior lens capsule (5) through which the opacified lens (6) can be removed. The remaining portion of the lens capsule (7), anchored to the ciliary body (9) through the zonular fibers (10) can be left intact. The IOL (11) can then be placed within the lens capsule (5). The IOL (11) can be acted on by zonular forces exerted on the outer circumference (12) of the lens capsule (5) to establish the location of the IOL (11) within the lens capsule (5). The intact posterior capsule (13) acts as a barrier to the vitreous humor (14).

Now referring primarily to FIGS. 72 through 74, following cataract extraction and cortex removal by ECCE or other surgical procedures to treat other ocular conditions, embodiments of the biocompatible or biocompatible biodegradable intraocular implant (18) can be held in forceps (136) as shown for example in FIG. 72. Embodiments of the intraocular implant (18) may also be removably fixed to the surface of an intraocular implant packaging substrate (49) from which it can be lifted with the forceps (136) prior to insertion into the eye (1)(8) as shown for example in FIGS. 73 and 74. The intraocular implant (18) can be folded upon itself to reduce the apparent dimension for passage through the corneal or scleral incision (2) as well as circular opening (4) in the anterior lens capsule (5) surrounded by the pupil (137) of the iris (138), as shown in FIGS. 73 and 74.

Now referring primarily to FIG. 74, the intraocular implant (18) can be positioned within the lens capsule (7) having a back surface (23)(which can further provide patterned surface elements (28) in any of the embodiments above described) proximate the surface or engaging the surface of the posterior capsule (13). The passage opening (27), of embodiments of the intraocular implant (18) which provide an aperture element (26), can be aligned with the visual axis (15) of the eye (1)(8) to provide a line of sight which passes through the passage opening (27) of the intraocular implant (18). The IOL (11) can then be located inside the lens capsule (7) by conventional methods to overlay the intraocular implant (18) placed in the cavity of the posterior capsule (13).

FIG. 75 illustrates the IOL (11) overlying the intraocular implant (18) with the passage opening (27) of the aperture element (26) centered underneath the IOL (11). If centration of the intraocular implant (18) is not adequate, it can be readily manipulated into position with a Sinskey Hook or similar instrument. As to particular embodiments, the outer boundary (20) of the intraocular implant (18) engages the outer circumference (12) of the lens capsule (7) as shown in FIG. 75 to maintain centration of the intraocular implant (18) without the use of attachment elements such as hooks extending from or passages in the circular area (21) for attaching to or through which tissue can be drawn. Once implanted into the eye, particular embodiments of the biocompatible biodegradable intraocular implant (18) can biodegrade as above described with normal turnover of the fluid of the eye.

Now referring primarily to FIG. 76, embodiments of the intraocular implant (18) having an annular member (50) can be placed in the cavity of the posterior capsule (13) with the outer annular surface (52) located proximate the outer circumference (12) of the lens capsule (7) with the back surface (23) either proximate or engaging the surface of the posterior capsule (13) or proximate or engaging the surface of the anterior capsule (5). The IOL (11) can be positioned to overlay the front surface (22) of intraocular implant (11) with the haptics (57) engaged with the inner annular surface (51) of the annular member (50) and the optical lens (58) of the IOL (11) substantially aligned with the passage opening (27) of the aperture element (26) to provide a visual axis (15) for the pseudophakic eye (8).

Now referring primarily to FIG. 77, a one-piece intraocular implant (18) as shown in the examples of FIGS. 31 and 34 can be placed in the cavity of the posterior capsule (13) with the outer annular surface (52) of the annular member (50) located proximate the outer circumference of the lens capsule (7). The one piece IOL (11) can be located in the lens capsule (7) by conventional methods to align the optical lens (58) of the one piece IOL (11) with the visual axis (15) of the eye (8).

Now referring primarily to FIG. 78, in those surgical procedures in which the natural crystalline lens (3) is not removed such as retinal surgery, cornea transplant surgery, glaucoma surgery, or the like, or in cataract surgery in which the intraocular implant (18) is not located posterior the IOL (11) (for example, due to posterior capsule tear), the intraocular implant (18) can be placed anterior to the natural lens (6) or the IOL (18) within the ciliary sulcus (139).

Example 1

Now referring primarily to FIGS. 39 through 42 smooth and patterned flexible membranes (19) were fabricated by casting biomedical grade polydimethylsiloxane elastomer ("PDMSe", SILASTIC® MDX4-4210; Dow Corning, Midland, Mich.) against negative silicon wafer molds. The flexible membranes (19) produced by this method included a plurality of patterned surface elements (28) and non-linear channel elements (71) arranged in a pattern (72) as shown in the examples of FIGS. 39 through 42 that either protruded from the surface of the PDMSe flexible membrane (19) as shown in the example of FIGS. 39 and 40 or were recessed into the PDMSe flexible membrane (19) as shown in the examples of FIGS. 41 and 42. A pattern (72) with patterned surface elements (28) protruding 3 μm from the surface of the flexible membrane (19) that were 2 μM wide and spaced by 2 μm would be called +3SK2×2. The patterns (72) replicated for testing included smooth unpatterned "SM", −3SK2×2, +3SK2×2, and +7SK10×5.

Example 2

Now referring primarily to FIGS. 79A through 79C and 80, circular flexible membranes (19)(diameter=about 20 mm) including "SM", "+1SK10×5", and +10SK50×50 samples were adhered to a 12-well plate with the axis A'-A' (101) of the plurality of groups of surface elements (78) of the "+1SK10×5", and "+10SK50×50" samples aligned orthogonal to the direction of cell adhesion, growth or migration (107) and treated with 15 μg/mL fibronectin (BD Biosciences, San Jose, Calif.) in phosphate buffered saline (Life Technologies, Carlsbad, Calif.) overnight to facilitate cell attachment. A modified scratch-wound assay was created by blocking cell attachment to the samples using SM PDMSe rectangles (3 mm×320 mm) placed along the center of the flexible member (19) to simulate wound areas (140). LECs (16)(ATCC CRL-11421; ATCC, Manassas, Va.) were seeded over the entire assembly at about 1×10$^4$ cells/cm$^2$ and maintained in growth media (Eagle's Minimum essential media; ATCC), 20% fetal bovine serum (Life Technologies), 50 U/mL penicillin/streptomyocin (Life Technologies), and 1 lg/mL Fungizoneantimycotic (Life Technologies). When LECs (16) reached approximately 70% confluence, the SM PDMSe rectangles were removed to allow LEC (16) migration across the empty patterned (72) "+1SK10×5" and "+10SK50×50" or SM unpatterned area of the simulated wound area (140). Migration was monitored via light microscopy until Day 7 when samples were stained with CellTracker Orange CMTMR® (Life Technologies) according to the manufacturer's instructions and fixed with 4% paraformaldehyde (Electron Microscopy Sciences, Hatfield, Pa.) for 15 minutes at room temperature. Fluorescent microscopy images were taken of the simulated wounded area (140) and the average area covered by LECs (16) within the simulated wound area (140) was calculated using ImageJ software (National Institutes of Health, Bethesda, Md.). Experiments were performed in triplicate with n=3 replicates. As evidenced by FIGS. 79A through 79 and presented in the bar graph of FIG. 80, each of the "+1SK10×5" and "+10SK50×50" samples significantly increased LEC (16) adhesion, growth or migration (107) compared to the SM sample. Sample "+10SK50×50" increased LEC (16) coverage by 64%, p=0.024 (ANOVA) compared to the SM sample. Sample "+1SK10×5 increased coverage by 462% as compared to the SM sample.

Example 3

Now referring primarily to FIGS. 81A through 81D and 82, circular flexible membranes (19)(diameter=about 20 mm) including "SM", −3SK2×2, +3SK2×2, and +7SK10×5 samples were adhered to a 12-well plate with the axis A'-A' (101) of the plurality of groups of surface elements (78) of the −3SK2×2, +3SK2×2, and +7SK10×5 samples aligned orthogonal to the direction of cell adhesion, growth or migration (107) and treated with 15 μg/mL fibronectin (BD Biosciences, San Jose, Calif.) in phosphate buffered saline (Life Technologies, Carlsbad, Calif.) overnight to facilitate cell attachment. A modified scratch-wound assay was created by blocking cell attachment to the samples using SM PDMSe rectangles (3 mm×320 mm) placed along the center of the flexible member (19) to simulate wound areas (140). LECs (16)(ATCC CRL-11421; ATCC, Manassas, Va.) were seeded over the entire assembly at 1×10$^4$ cells/cm$^2$ and maintained in growth media (Eagle's Minimum essential media; ATCC), 20% fetal bovine serum (Life Technologies), 50 U/mL penicillin/streptomyocin (Life Technologies), and 1 lg/mL Fungizoneantimycotic (Life Technologies). When LECs (16) reached approximately 70% confluence, the SM PDMSe rectangles were removed to allow LEC (16) migration across the empty patterned (72) or SM unpatterned area of the simulated wound area (140). Migration was monitored via light microscopy until Day 7 when samples were stained with CellTracker Orange CMTMR® (Life Technologies) according to the manufacturer's instructions and fixed with 4% paraformaldehyde (Electron Microscopy Sciences, Hatfield, Pa.) for 15 minutes at room temperature. Fluorescent microscopy images were taken of the simulated wounded area (140) and the average area covered by LECs (16) within the simulated wound area (140) was calculated using ImageJ software (National Institutes of Health, Bethesda, Md.). Experiments were performed in triplicate with n=3 replicates. As evidenced by FIGS. 81A through 81C and presented in the bar graph of FIG. 82, each of the −3SK2×2, +3SK2×2, and +7SK10×5 samples significantly reduced LEC (16) adhesion, growth or migration (107) compared to the SM sample. Sample +7SK10×5 reduced LEC (16) coverage by 80%, p=0.0001 (ANOVA) compared to the SM sample. Samples −3SK2×2 and +3SK2×2 reduced coverage by 32% and 61% respectively compared to the SM sample.

Example 4

Now referring to FIGS. 22 through 30, steel casting molds were designed and machined by 103 MicroStructures (Wheeling, Ill.) for prototype intraocular implant (18) production. Intraocular implants (18) (as shown by the examples of FIGS. 22 through 30) were replicated in PDMSe and sterilized by immersion in 70% ethanol in water (vol/vol) prior to use. Intraocular implants (18) were designed with a generally circular annular member (50) (outer annular surface (52) diameter of about 9.5 mm). A thin flexible membrane (19) (thickness (24) of about 0.1 mm) spanned the area between the annular member (50) and an aperture element (26) providing a visual axis (15) for the optical lens (58) (diameter of 5.5 mm) of an IOL (11). The inner annular surface (51) of the annular member (50) had an annular inner surface height (56) of about 1.2 mm to which the haptics (57) of the IOL (11) were engaged to retain the IOL (11) within the intraocular implant (18). The flexible membrane (19) was designed to rest against the posterior capsule (13) to inhibit LEC (16) migration from the outer circumference (12) of the lens capsule (7) as shown in the example of FIG. 77. The back surface (23) of the flexible membrane (19) was either unpatterned SM (negative control) or patterned +7SK10×5. An interconnected boundary (109) defined a plurality of sections (108) each having a square patterned surface area (11) with alternating orthogonal orientation of the pattern (72) axis A'-A' (101) in each 500 µm square section (108) to produce a surface to block adhesion, growth or migration (107) of LECs (16) from all directions.

Example 5

Now referring primarily to FIGS. 83A through 83C and 84, an IOL (11) with or without a flexible membrane (19) produced in accordance with the method of Example 4 was placed into a 6-well plate containing a collagen-coated transwell insert (Corning, Corning, N.Y.). Each assay valuated IOLs (11) (ACRYLSOF IQ®; TORIC®; Alcon, Minitab, Inc., Fort Worth, Tex.) without a flexible membrane (19), IOLs (11) combined with SM unpatterned flexible membranes (19) and IOLs (11) combined with flexible membranes (19) having patterned surface elements (28). A silicone annular member (50) was placed around the outside of the well to either engage the haptics (57) of the IOL (11) or to establish the same surface area available for cell attachment around all IOLs (11) and IOL (11)/flexible membrane (19) combinations. The entire assembly was weighted down (~5 g) to ensure that IOLs (11) maintained contact with the collagen flexible membranes (19). LECs (16) were seeded into each well at 1 3 104 cells/cm2 and maintained in growth media (Eagle's minimum essential media, 20% fetal bovine serum, 50 U/mL penicillin/streptomycin, and 1 µg/mL Fungizone antimycotic). After 7 days, LECs (16) were stained with CellTracker Orange CMTMR® (Life Technologies) according to the manufacturer's instructions and fixed with 4% paraformaldehyde (Electron Microscopy Sciences, Hatfield, Pa.) for 15 minutes at room temperature. Fluorescent microscopy was used to focus on cells attached to the collagen membrane both outside and behind each sample, images were taken of each sample type, and the average surface area coverage behind the IOL (11) was calculated using ImageJ software for n=3 replicates in three experiments. Intraocular implants (18) having a circular annular member (50) with an outer annular surface (52) orthogonally intersecting a thin membrane modified with the +7SK10×5 pattern (as shown in the example of FIG. 83C) reduced LEC (16) migration between the collagen membrane and the IOL (11) by 50% (P=0.0005; ANOVA, Tukey Test)(as presented by the bar graph in FIG. 84) compared with the IOL (11) only condition (as shown in the example of FIG. 83A and FIG. 84). Intraocular implants (18) with circular annular members (50) with an outer annular surface (52) orthogonally intersecting a thin smooth membrane SM (as shown in the example of FIG. 83B) reduced LEC (16) migration compared with the IOL (11) only condition (as shown in the example of FIG. 84A).

Example 6

Now referring primarily to FIGS. 22 through 25 and 26 through 30 and 85A through 85C and 86, an animal study evaluated the stability and opacification of the capsular bag (7)(opacification of the anterior lens capsule (5) and opacification of the posterior capsule (13)) associated with intraocular implant (18) as shown in the examples of FIGS. 22 through 25 and 26 through 30 as a secondary implant around an IOL (11) (SA60AT; single-piece hydrophobic acrylic; ACRYSOF® IOL manufactured by Alcon; all in +20.0 D). The efficacy of an intraocular implant (18) having flexible membrane (19) including patterned surface elements (28) (as shown in the examples of FIGS. 26 through 30) to prevent capsular bag (7) opacification compared to the intraocular implant (18) having an flexible membrane (19) without patterned surface elements (28) (as shown in the examples of FIGS. 22 through 25) and the commercially available IOL (11) control was assessed in a rabbit model. Four weeks after implantation of the IOL (11) control or the intraocular implants (18) with or without patterned surface elements (28), PCO was scored on a scale of 1 to 5. Results of this study evidence that the presence of a intraocular implant (18) as shown in FIGS. 22 through 25 or 26 through 30 eliminated clinically significant PCO. Clinical examination via slit lamp (as shown in the examples of FIGS. 85A through 85C) demonstrated a significant reduction in PCO in all eyes with the intraocular implant (18) as compared to eyes (8) with an IOL (11) only (0.64 vs. 2.33, p=0.0004, Table 1 and FIG. 86). Images were also evaluated for clinically significant PCO, as to whether a follow up Nd:YAG laser capsulotomy would be required; conservative estimates were that 5 of the 5 IOL only eyes and 0 of 6 eyes in each intraocular implant (18) group (whether patterned and un-patterned) would require follow up Nd:YAG laser capsulotomy. Gross examination results confinned clinical findings: the average central PCO score for eyes (8) with IOL (11) alone (no intraocular implant (18)) was 2.08±1.28, while eyes implanted with both IOL (11) and intraocular implant (18) scored 0.28±0.32 (p<0.00001; Student's T-test).

TABLE 1

| Implant Type | Total PCO Score | YAG laser treatment recommended due to clinically significant PCO |
|---|---|---|
| IOL alone | 2.33 ± 1.03 | 5/5 eyes |
| IOL + Membrane | 0.64 ± 0.69 | 0/12 eyes |

Example 7

Now referring primarily to FIGS. 33 through 34 and FIG. 87, additional experiments were conducted with intraocular implants (18) fabricated in accordance with the procedure of Example 4 and the experimental method described in Example 6 with implantation of the intraocular implant (18) retaining the IOL (11) with back surface (23) of the flexible membrane (19) engaged with the anterior capsule (5) and the top annular surface (74) of the annular member (50) engaging the posterior capsule (13). Results of this study evidence that the presence of an intraocular implant (18) as shown in FIG. 22 through 25 or 26 through 30 implanted as above described substantially reduced PCO. The average central PCO score for eyes (8) with IOL (11) alone (no intraocular implant (18)) was 2.08±1.28, while eyes implanted with both IOL (11) and intraocular implant (18) in the instant orientation scored 0.40±0.32 (p<0.00001; Student's T-test). Reduction of PCO may be due to a "dual square edge" that occurs due to the two 90° edges of the top surface (74) of the annular member (50) being engaged with the surface of the posterior capsule (13). An intraocular implant (18) as shown in the example of FIG. 33 having an annular channel (61) can be utilized to provide a similar "dual square edge" and can be combined with a plurality of patterned surface elements (28) for a combined effect in reducing PCO.

As can be easily understood from the foregoing, the basic concepts of the present invention may be embodied in a variety of ways. The invention involves numerous and varied embodiments of an intraocular implant (18) which as to particular embodiments can be used to control the flow of fluids (105), the flow of particles suspended in a flow of fluids (106), or the adhesion, growth, or migration (107) of LECs (16) between the intraocular implant (18) and a surface of a localized region of the eye (1)(8) such as the surface of the posterior capsule (13) of the eye (1)(8) to reduce opacification of the posterior capsule (13).

As such, the particular embodiments or elements of the invention disclosed by the description or shown in the figures or tables accompanying this application including the best mode are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of "an implant" should be understood to encompass disclosure of the act of "implanting"— whether explicitly discussed or not—and, conversely, were there effectively disclosure of the act of "implanting", such a disclosure should be understood to encompass disclosure of "an implant" and even a "means for implanting." Such alternative teems for each element or step are to be understood to be explicitly included in the description.

In addition, as to each term in used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

Thus, the applicant(s) should be understood to claim at least: i) each of the intraocular implants herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. An intraocular implant, comprising:
    an intraocular implant having an external surface configured for implantation in a posterior capsule of eye, said intraocular implant including:
    an optical lens;
    a biocompatible flexible membrane connected to a circumference of said optical lens, said biocompatible flexible membrane extending outward of said optical lens to terminate in an annular member; and
    a plurality of groups of surface elements, wherein each group comprises a plurality of surface elements having a pattern repeated over the external surface of the intraocular implant, the plurality of groups of surface elements defining a tortuous pathway which traverses the plurality of groups of surface elements,
    wherein said plurality of surface elements comprises a plurality of concentric bands of increasing diameter disposed about a central point, said plurality of concentric bands radially spaced apart and periodically interrupted circumferentially by a plurality of gaps defining said tortuous pathway on said intraocular implant which traverses said plurality of surface elements.

2. The intraocular implant of claim 1, wherein said plurality of bands are circumferentially spaced apart and periodically interrupted radially by a plurality of gaps defining said tortuous pathway on said intraocular implant which traverses said plurality of surface elements.

* * * * *

UNITED STATES PATENT AND TRADEMARK OFFICE
CERTIFICATE OF CORRECTION

PATENT NO. : 9,943,402 B2
APPLICATION NO. : 14/821645
DATED : April 17, 2018
INVENTOR(S) : Cuevas et al.

Page 1 of 1

It is certified that error appears in the above-identified patent and that said Letters Patent is hereby corrected as shown below:

On the Title Page

Item (63), Related U.S. Application Data, continued on second page,
"PCT/US2009/006165" should read --PCT/US2009/006195--.

In the Claims

Column 38,
Line 38, "capsule of eye" should read --capsule of an eye--.

Signed and Sealed this
Twenty-fourth Day of July, 2018

Andrei Iancu
*Director of the United States Patent and Trademark Office*